United States Patent [19]

Broderick

[11] Patent Number: 5,443,710

[45] Date of Patent: Aug. 22, 1995

[54] MICROELECTRODES AND THEIR USE IN A CATHODIC ELECTROCHEMICAL CURRENT ARRANGEMENT WITH TELEMETRIC APPLICATION

[75] Inventor: Patricia A. Broderick, Bronx, N.Y.

[73] Assignee: Research Foundation, The City University of New York, New York, N.Y.

[21] Appl. No.: 978,449

[22] Filed: Nov. 18, 1992

Related U.S. Application Data

[63] Continuation-in-part of Ser. No. 565,821, Aug. 14, 1990, abandoned, which is a continuation-in-part of Ser. No. 395,431, Aug. 17, 1989, abandoned, which is a continuation-in-part of Ser. No. 905,579, Sep. 9, 1986, Pat. No. 4,883,057, which is a continuation-in-part of Ser. No. 608,426, May 9, 1984, abandoned.

[51] Int. Cl.$^6$ .................... G01N 27/26; A61B 5/07
[52] U.S. Cl. .................... 204/403; 128/635; 128/642; 128/731; 204/412
[58] Field of Search ............. 128/631, 635, 642, 731, 128/734, 904; 204/153.1, 400, 403, 412

[56] References Cited

U.S. PATENT DOCUMENTS

| | | | |
|---|---|---|---|
| 3,850,161 | 11/1974 | Liss | 128/2.1 R |
| 3,868,578 | 2/1975 | Oldham | 328/127 |
| 3,872,252 | 3/1975 | Malchman et al. | 197/2 A |
| 4,319,241 | 3/1982 | Mount | 340/870.38 |
| 4,424,812 | 1/1984 | Lesnick | 128/419 PG |
| 4,499,552 | 2/1985 | Kanazawa | 364/802 |

FOREIGN PATENT DOCUMENTS 8505021 11/1985 WIPO .

OTHER PUBLICATIONS

"The Condensed Chemical Dictionary", Van Nostrand Reinhold Co., Jan. 1979, pp. 374, 815 and 924–925.
Life Sciences, vol. 45, pp. 2025–2039 (Nov. 14, 1989), Morgan & Vestal, "Methylxanthine Effects on Caudate Dopamine Release as Measured by In Vivo Electrochemistry".
Electroanalysis, 2, 241–251, Patricia A. Broderick, "State-of-the-Art Microelectrodes for In Vivo Voltammetry" (Apr., 1990).
Khodari, M., et al., J. Pharmaceut. "Biomed. Anal.," 7(12); 1491–1497 (1989).
Brain Research, 114(1976) 346–352, Lane et al., "Brain Catecholamines: Detection in vivo by means of differential pulse voltammetry at surface-modified platinum electrodes".
The Journal of Neuroscience, Sep. 1987, Marrocco et al., "Release of Cortical Catecholamines by Visual Stimulation Real Activity in Thalamocortical Afferents of Monkey and Cat".
Dept. of Chemistry, University of Kansas, 1966, Hawley et al. "Electrochemical Studies of the Oxidation Pathways of Catecholamines".
Brain Research Bulletin, vol. 10, pp. 861–864, 1983, Blaha et al., "Chemically Modified Electrode for In Vivo Monitoring of Brain Catecholamines".
European Journal of Pharmacology, 98(1984) 113–117, Blaha et al., "Direct In Vivo Electrochemical Monitoring of Dopamine Release in Response to Neuroleptic Drugs".
European Journal of Pharmacology, 123 (1986) 433–439, DeSimoni et al. "Differences in the Effect of the Antidepressant Amineptine on Striatal and Limbic Dopac Measured by HPLC–ECD and In Vivo Voltammetry".

(List continued on next page.)

Primary Examiner—Nam Nguyen
Attorney, Agent, or Firm—Morgan & Finnegan

[57] ABSTRACT

This invention relates to a microelectrode comprising graphite, oil and, additionally, a compound selected from the group of lipids, glycolipids, lipoproteins, fatty acids, fatty acid derivatives, any water insoluble species and perfluorosulfonated compounds and salts thereof. This invention also relates to a method for using the microelectrode, a device that may be employed with the microelectrode, a method for making the microelectrode, and a method for using the device with the microelectrode.

32 Claims, 53 Drawing Sheets

OTHER PUBLICATIONS

Neuroscience Letters, 45(1984) 39-46, O'Neill et al., "Voltammetric Carbon Paste Electrodes Monitor Uric Acid and Not 5-HIAA at the 5-Hydroxyindole Potential in the Rat Brain".

Lane et al., "Electrochemistry in Vivo: Application to CNS Pharmacology," Annals of NY Academy of Sciences, vol. 473 (Dec. 15, 1986).

Life Sciences, vol. 30, pp. 2155-2162, 1982, Yamamoto et al. "Normal Rats Trained to Circle Show Asymmetric Caudate Dopamine Release".

Analytical Chemistry, vol. 58, No. 6, May 1986, pp. 1028-1032, Gelbert et al. "Alternating Current Voltammetry of Dopamine and Ascorbic Acid at Carbon Paste and Stearic Acid Modified Carbon Paste Electrodes".

Neuropeptides (1987) 10, 369-386, P. A. Broderick, "Striatal Neuochemistry of Dynorphin-(1-13): In Vivo Electrochemical Semidifferential Analyses".

Lyne et al., "Selectivity of Stearate-Modified Carbon Paste Electrodes for Dopamine and Ascorbic Acid," Anal. Chem., 61, 2323-2324 (Sep. 11, 1989).

Chem., Biomed., & Environ. Instrumentation, 10(3), 311-330 (1980), Lindsay et al. "Microcomputer Controlled Multielectrode System for In Vivo Electrochemistry".

Analytical Chemistry, vol. 45, No. 1, Jan. 1973, pp. 39-47, K. B. Oldham, "Semi-integral Electroanalysis: Analog Implementation".

Brain Research, 55(1973), 209-213, Kissinger et al., "Voltammetry in Brain Tissue-A New Neurophysiological Measurement".

Brain Research, 267(1983), 183-186, Clemens et al., "Changes in Brain Chemistry Produced by Dopaminergic Agents: In Vivo Electrochemical Monitoring Reveals Opposite Changes in Anesthetized vs Unanesthetized Rats".

Neuroscience Letters, 95(1988) 275-280, Patricia A. Broderick, "Distinguishing in vitro electrochemical signatures for norepinephrine and dopamione".

Brain Research (Aug. 21, 1989) Patricia A. Broderick, "Characterizing stearate probes in vitro for the electrochemical detection of dopamine and serotonin".

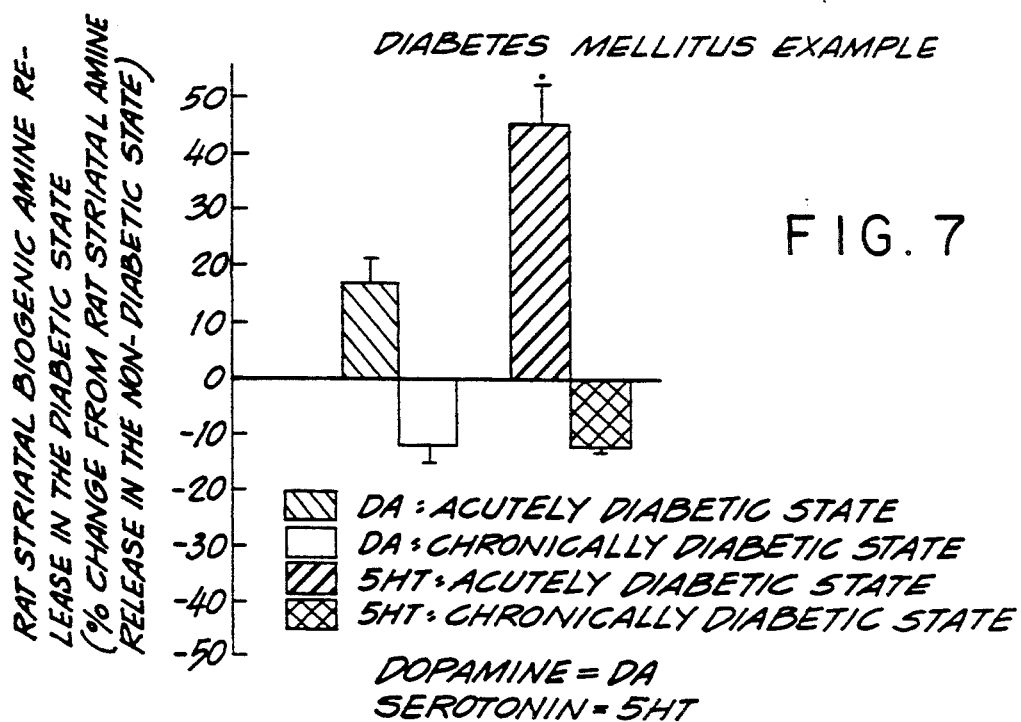
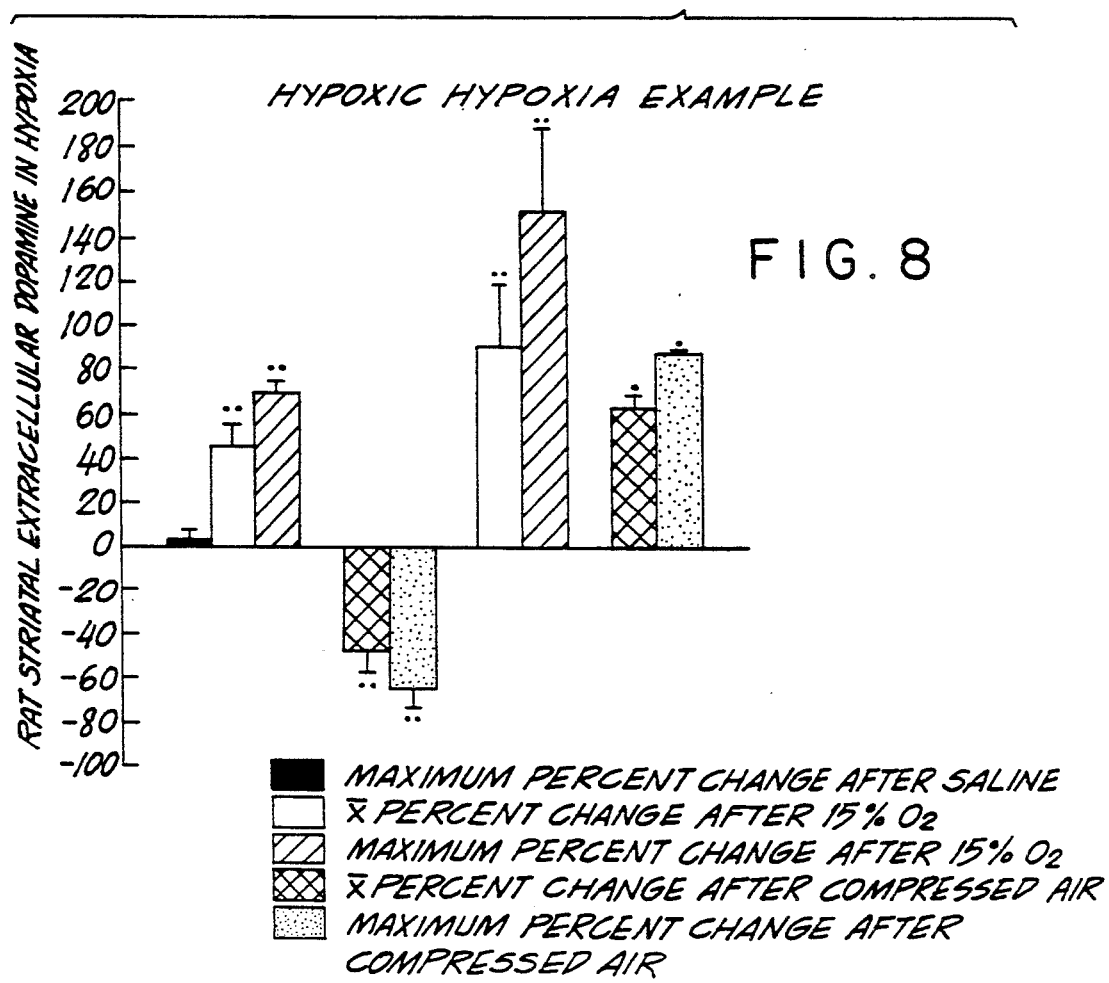

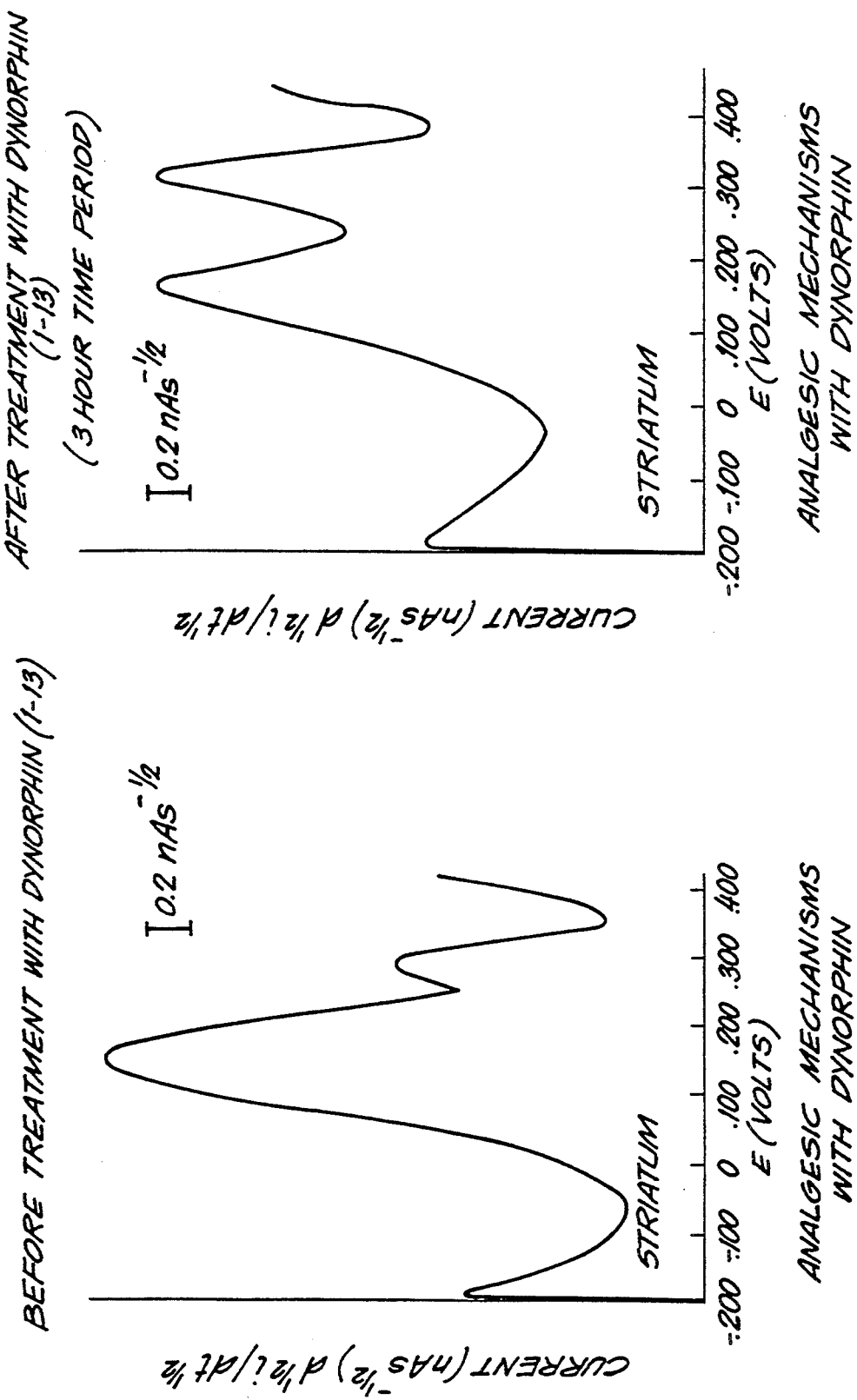

POST-MORTEM DOPAMINE RELEASE

WHERE +0.08V REPRESENTS THE OXIDIZED SPECIES OF 6OHQA AND -0.32V REPRESENTS THE REDUCED SPECIES OF 6OHQ.

METHOD FOR CHANNEL 0

1.     C H R O M A T O C H A R T  V1.07
2. RUN IDENTIFICATION/FILES OPTIONS
3. TITLE $ AUTO
4. DATE $ 9/25/85
5. TIME $ AM
6. OPERATOR$
7. CONDITIONS$           V
8. DISK FILENAME.S,D $ AUTO,  S6, D2
9. SAVE DAT.FILE (Y:N) $ Y
10. SAVE BAS.FILE (Y:N) $ Y
11. SAVE PEK.FILE (Y:N) $ Y
12. GRADIENT FILENAME.S,D$
13. STANDARD FILENAME, S,D$ _____
14.
15. DATA ACQUISITION OPTIONS
16. ADALAB SLOT (0:7) : 2
17. RAM SLOT    (0:7) : 0
18. RAM ADDRESS, K (1:255): 1
19. RUN LENGTH, K  (1:64): 1
20. FIRST RUN # (1:127): 13
21. # REPEAT RUNS (0:127): 0
22. AVERAGE # POINTS (1:8) # 4
23. SUM # POINTS    (1:8) : 2
24. CHART DELAY    (1:127) : 10
25. CHART WIDTH. 100'S (1:4) :  4
26. CHART Y SCALE    (1:255) :  20
27. CHART OFFSET (-9999:9999) : -10
28. CHART HARDCOPY (Y:N) $ Y
29.
30. INTEGRATION/REPORT OPTIONS
31. SMOOTHING WIDTH (3:15) : 9
32. INIT. SLOPE THRESH. (1:32767) : 10000
33. MINIMUM BASELINE WIDTH (1:99) : 70
34. INITIAL PEAK WIDTH (1:99) : 10
35. WIDTH % CHANGE  (1:100) : 70
36. SHOULDER % WIDTH (1:100) : 100
37. MIN. PEAK AREA (1:32767) : 100
38. REVIEW BASELINE (Y:N) $  N
39. TIME UNITS IN REPORT (SEC:MIN) $ SEC
40. REPORT PRINTER SLOT #(0:7) : 1
41. CHART HARDCOPY (Y:N) $ Y
42. CHART WIDTH, 100'S (1:4) : 2
43. CHART X SCALE    (1:20) : 1
44. CHART Y SCALE  (-255:255) : 20
45. CHART OFFSET (-9999:9999) : -10

FIG. 28(a)
SH. 1 OF 2

EVENT CONTROL SCHEDULE

| EVT | SECONDS | TYPE | BIT | ON/OFF | GOTO |
|---|---|---|---|---|---|
| 1 | 0 | STATUS | 1 | | |
| 2 | 1 | SWITCH | 2 | OFF | |
| 3 | 121 | SWITCH | 1 | OFF | |
| 4 | 136 | STATUS | 5 | | |
| 5 | 185 | STATUS | 1 | | |
| 6 | 242 | SWITCH | 1 | ON | |
| 7 | 243 | SWITCH | 2 | ON | |
| 8 | 244 | SWITCH | 3 | OFF | |
| 9 | 245 | SWITCH | 3 | ON | |
| 10 | 400 | STATUS | 1 | | |
| 11 | 401 | STATUS | 0 | | |

FIG. 28(a)
SH. 2 OF 2

METHOD FOR CHANNEL 0

1. C H R O M A T O C H A R T V1.07
2. RUN IDENTIFICATION/FILES OPTIONS
3. TITLE$ VIVO
4. DATE$ 4/8/86
5. TIME$ AM
6. OPERATOR $
7. CONDITIONS$            V
8. DISK FILENAME,S,D$ VIVO,S6,D2
9. SAVE DAT.FILE   (Y:N) $ Y
10. SAVE BAS.FILE  (Y:N) $ Y
11. SAVE PEK. FILE (Y:N) $ Y
12. GRADIENT FILENAME,S,D $
13. STANDARD FILENAME,S,D $_____
14.
15. DATA ACQUISITION OPTIONS
16. ADALAB SLOT (0:7) : 2
17. RAM SLOT         (0:7) : 0
18. RAM ADDRESS,  K(1:255) : 1
19. RUN LENGTH , K    (1:64) : 1
20. FIRST RUN #       (1:127) : 1
21. # REPEAT RUNS    (0:127) : 0
22. AVERAGE # POINTS (1:8) # 4
23. SUM # POINTS        (1:8) : 2
24. CHART DELAY       (1:127) : 10
25. CHART WIDTH, 100'S  (1:4) :  4
26. CHART Y SCALE    (1:255) : 20
27. CHART OFFSET (-9999:9999) : -10
28. CHART HARDCOPY (Y:N)$ Y
29.

FIG. 28(b)
SH. 1 OF 2

30. INTEGRATION/ REPORT OPTIONS
31. SMOOTHING WIDTH (3:15) : 5
32. INIT. SLOPE THRESH. (1:32767) : 500
33. MINIMUM BASELINE WIDTH (1:99) : 1
34. INITIAL PEAK WIDTH (1:99) : 80
35. WIDTH % CHANGE (1:100) : 70
36. SHOULDER % WIDTH (1:100) : 80
37. MIN. PEAK AREA (1:32767) : 100
38. REVIEW BASELINE (Y:N)$ N
39. TIME UNITS IN REPORT (SEC:MIN) $ SEC
40. REPORT PRINTER SLOT #(0:7) : 1
41. CHART HARDCOPY (Y:N)$ Y
42. CHART WIDTH, 100'S (1:4) : 2
43. CHART X SCALE (1:20) : 1
44. CHART Y SCALE (-255:255) : 20
45. CHART OFFSET (-9999:9999) : -10

EVENT CONTROL SCHEDULE

| EVT | SECONDS | TYPE | BIT | ON/OFF | GOTO |
|---|---|---|---|---|---|
| 1 | 0 | STATUS | 1 | | |
| 2 | 1 | SWITCH | 2 | OFF | |
| 3 | 121 | SWITCH | 1 | OFF | |
| 4 | 136 | STATUS | 5 | | |
| 5 | 185 | STATUS | 1 | | |
| 6 | 242 | SWITCH | 1 | ON | |
| 7 | 243 | SWITCH | 2 | ON | |
| 8 | 244 | SWITCH | 3 | OFF | |
| 9 | 245 | SWITCH | 3 | ON | |
| 10 | 400 | STATUS | 1 | | |
| 11 | 401 | STATUS | 0 | | |

FIG. 28(b)
SH. 2 OF 2

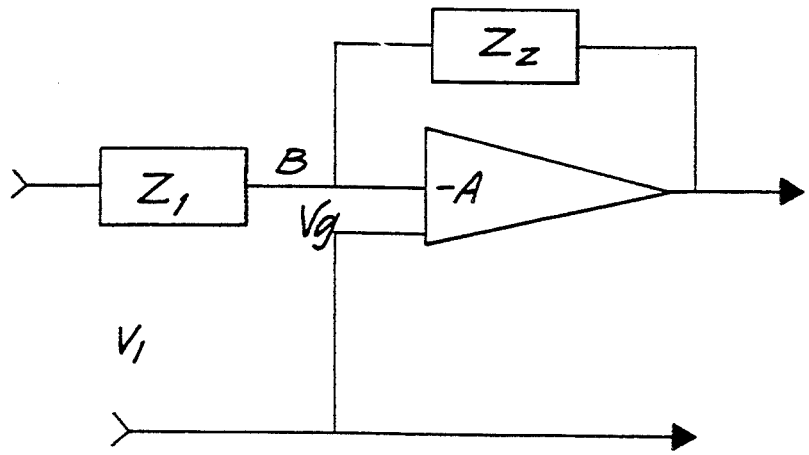
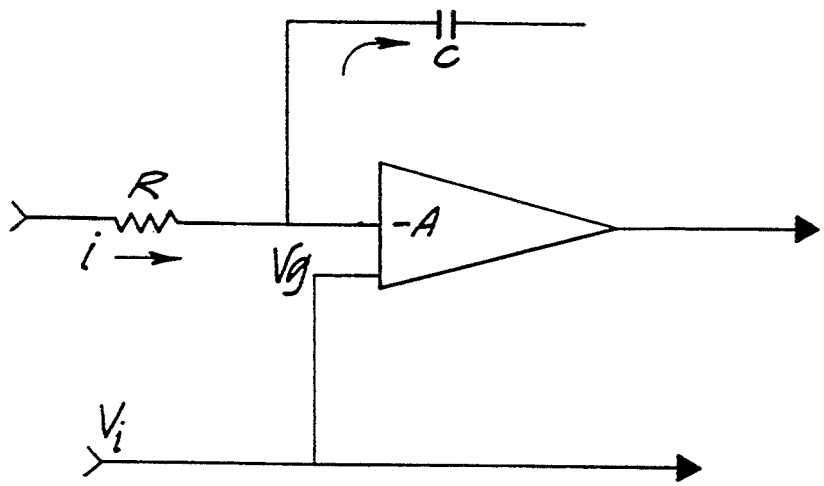
FIG. 29
(PRIOR ART)

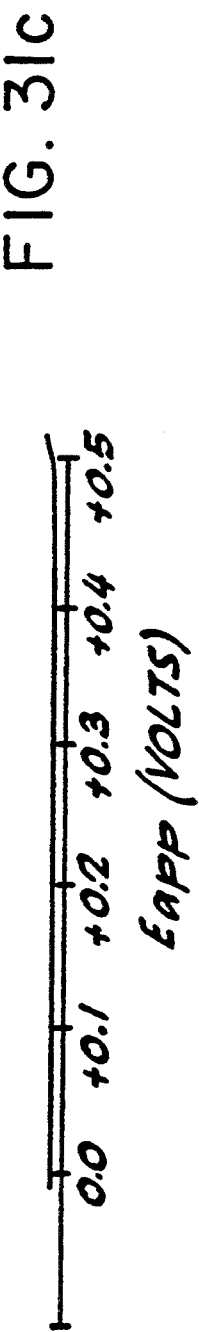
FIG. 31a — 5μM DOPAMINE
FIG. 31b — 5μM SEROTONIN
FIG. 31c — PHOSPHATE BUFFER: pH 7.4

5 µM DA, 5-HT ———
5 µM AA, UA, 5-HIAA & DOPAC. NOT DETECTED

FIG. 40
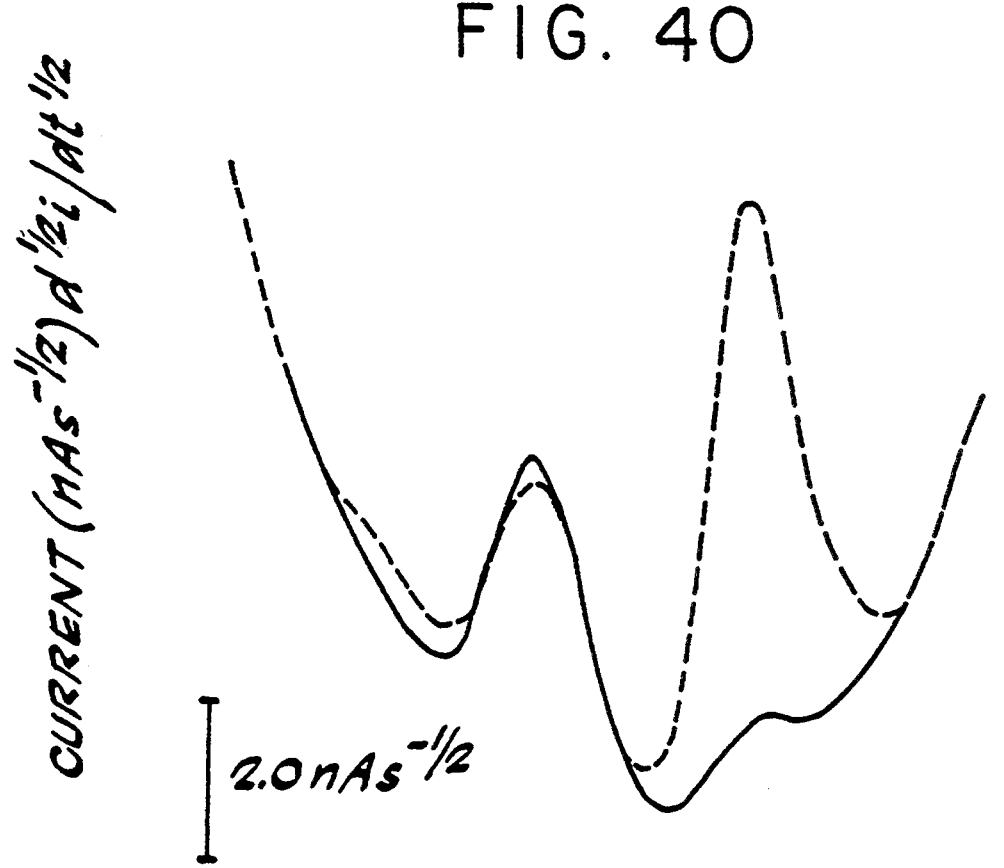
b) 5μM NE, 5μM 5-HT
a) 5μM NE, 1μM 5-HT
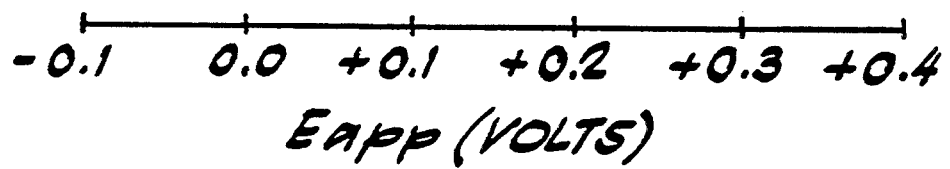
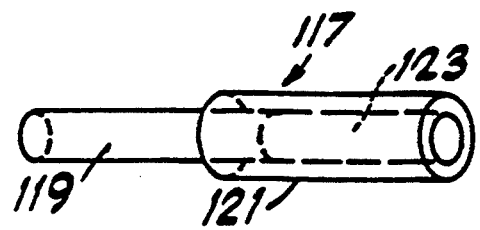
FIG. 44

MICROELECTRODES AND THEIR USE IN A CATHODIC ELECTROCHEMICAL CURRENT ARRANGEMENT WITH TELEMETRIC APPLICATION

This is a continuation-in-part of application Ser. No. 07/565,821, filed on Aug. 14, 1990, now abandoned, which is a continuation-in-part of U.S. patent application Ser. No. 07/395,431, filed Aug. 17, 1989, (now abandoned), which is a continuation-in-part of U.S. patent application Ser. No. 06/905,579, filed Sep. 9, 1986, (now U.S. Pat. No. 4,883,057) which is a continuation-in-part of U.S. patent application Ser. No. 06/608,426, filed May 9, 1984, abandoned, these predecessor applications and patent are incorporated herein by reference.

BACKGROUND OF THE INVENTION

I. Field of the Invention

This invention relates to the use of an in vivo electrochemical method (also called an in vivo voltammetric method or voltammetry) to measure the amounts of biogenic chemicals present in the body and brain of an animal or a human being. More particularly, it relates to the use of in vivo semiderivative voltammetric measurements of biogenic chemicals, particularly neurotransmitters, such as amines, amine metabolites, ascorbic acid, amino acids and neuropeptides produced in reaction to psychopharmacological agents and neuropsychopharmacological agents such as analgesics, antipsychotic drugs, antidepressants, and other modulators of brain and peripheral neurochemistry in diseased and healthy states.

II. Discussion of Background

It has been known to those possessing ordinary skill in the art that it is possible to measure certain limited types of biogenic chemicals using in vivo electrochemistry in the brains and suborgans of nonhuman primates and other animals. This measurement has been accomplished using such facets of electrochemical measurements as chronoamperometry, differential pulse voltammetry, double differential pulse voltammetry, linear scan voltammetry, and semiderivative voltammetry. In all of these methods, a working electrode, a reference electrode and an auxiliary electrode are attached to the brain or other organ of the animal to be studied. A controlled potential is applied to the working electrode and the current passing between the working electrode and the reference electrode is monitored as a signal and used to measure basal neurotransmitter release and any alterations in brain neurochemistry after pharmacological manipulation with drugs and other compounds and/or after a diseased state such as schizophrenia or Alzheimer's has been induced or mimicked. The signal is directly related to the chemical concentration of the neurotransmitter released from or through or taken up by or through the neuronal brain membrane (extracellularly) or the synaptic vesicles or other relevant organelles or cytoplasm (intracellularly). The mechanism of action can be presynaptic, or possibly postsynaptic and each signal represents an instantaneous readout of rate of neuronal mechanism. The signal may also be related to inhibition of normal reuptake of neurotransmitter at the neuronal membrane and may be a summation of release and reuptake processes, especially during treatment. The prior art teaches that this current is an anodic (oxidation) current, based on scientific principle. This signal is recorded as a graph indicating change in current with respect to time (chronoamperogram) or voltage (voltammogram).

It is known that voltametric measurements can be used to detect certain biogenic substances in the brain of rats [Kissinger, P. T.; Hart, J. B.; Adams, R. N.; "Voltammetry in Brain Tissue—A New Neurophysiological Measurement", Brain Research, 55 (1973), p. 209.]. Other researchers have also detected signals in the brains of living rats, as follows: McCreery, et al., Brain Res. Vol. 73 (1974), p. 23; Gonon, et al., Brain Res. Vol. 223 (1981), p. 69; Lane, et al., J. Electroanal. Chem., Vol. 95(1979), p. 117; Clemens and Phebus, Brain Res., Vol 267(1983), p. 183 and Millar, et al., Eur. J. Pharmacol. Vol. 109(1985), p. 341.

There has been, however, little or no description of circuitry for in vivo electrochemical circuits. However, certain improvements have been made for in vitro voltametric measurements since the linear scan for in vivo electrochemistry method was first described for measuring biogenic chemicals. One such improvement was the in vitro processing of the linear scan current signal as the first half-derivative of the linear signal [Oldham, "Analytical Chemistry" Vol. 45 (1973) p. 39 and U.S. Pat. No. 3,868,578; Kanazawa, U.S. Pat. No. 4,449,552]. However, neither Oldham nor Kanazawa describe circuitry applicable for detection of organic materials in living organisms. Although they describe oxidation and reduction reaction species, they do not describe cathodic (reduction) currents in vivo. For the purposes of this application, cathodic current is defined as current based on the acquisition of electrons by neurochemicals within the organ or suborgan and flowing away from and/or on an indicator electrode situated within the organ or suborgan. Anodic current is defined as current based on the loss of electrons by neurochemicals in the organ or suborgan and flowing toward and/or on an indicator electrode situated within the organ or suborgan.

When applied to the brain, or other body organs, this type of processing (the first half derivative of the linear signal) should result in a semidifferentiated voltammogram having sharper peaks, which then allows greater separation between peaks representing chemical substances and which are easier to read than previous, linear voltammograms. The older conventional methods did not allow sharply defined individual detection of amines because of similar electrochemical potentials for biogenic amines set by the catechol moiety of the amines. Chronoamperometry, for example, does not allow any direct, individual and simultaneous detection of the biogenic amines. Semiderivation or semidifferentiation of the signal briefly allowed somewhat better detection. Many practitioners, however, have found it difficult or impossible to obtain reproducible measurements routinely using what is known as the in vivo electrochemistry technique of semiderivative or semidifferential voltammetry.

Although telemetric devices have been produced in the past, as described in U.S. Pat. No. 4,424,812 (Lesnick) and U.S. Pat. No. 3,882,277 (DePedro), telemetric devices for monitoring brain signals have not been described. Neither of these patents describe monitoring signals produced electrochemically either in vivo, in vitro or in situ.

The wisdom of the prior art indicates that an oxidation current, or anodic current, should be used to detect biochemical species in the brain. Previous researchers assumed that in living systems, all chemical species which could be detected by electrochemical signals were converted into stable oxidized species. Most of the previous researchers also assumed that all biogenic chemical reactions produced oxidized species without producing stable reduced species. These assumptions have provided only a limited tool for diagnosing the mental and physiological states of living organisms, as only a limited number of biogenic chemicals can be detected using prior art methods.

SUMMARY OF THE INVENTION

It is an object of this invention to provide a method for measuring biogenic chemicals.

It is another object of this invention to provide an in vivo, in situ or in vitro electrochemical method for measuring biogenic chemicals.

It is another object of this invention to provide a useful way to measure biogenic chemicals using the semiderivative or semidifferential voltammetric technique to produce a cathodic current.

It is another object of this invention to provide the circuitry for such a cathodic current.

It is another object of this invention to provide a cyclic voltammogram within the context of the cathodic current.

It is another object of this invention to provide an in vivo electrochemical method for measuring biogenic amines, amine metabolities, ascorbic acid, amino acids and neuropeptides and other neurotransmitters and modulators of brain neurochemistry.

It is another object of this invention to provide an in vivo electrochemical method for measuring alterations in biogenic brain chemicals in relation to the administration, both peripheral and central, of psychopharmacological agents and neuropsychopharmacological agents such antidepressants, analgesics, antianxiety agents, anti-panic agents, anti-manic/depressive agents, calcium blocking agents, agents of addiction, other neuropeptides, enkephalinamides, dynorphin and other potential modulators of brain neurochemistry.

It is another object to provide an in vivo electrochemical method for interpreting these alterations in brain neurochemistry for diagnosing mental illness, Alzheimer's disease, and other diseased states caused by or which involve these neurochemical alterations, vis-a-vis healthy states, and developing new and more effective psychotherapeutic agents and other clinical applications.

It is another object of this invention to provide an in vivo electrochemical method for measuring the levels and dynamic changes of biogenic chemicals with an instantaneous readout of rate in humans, in vivo.

It is another object of this invention to provide a means for studying the dynamic levels, reuptake and/or release of biogenic chemicals produced during certain behavioral manifestations and thus provide a method for determining the causes of these manifestations.

It is another object of this invention to provide a method by which to correlate the production of certain biogenic chemicals with electrophysiological measurements and other measurements such as dialysis measurements.

It is another object of this invention to develop electrodes which are extremely selective to biogenic chemicals, which could be and are biological markers.

It is another object of this invention to provide a method of making reference, indicator (working) and auxiliary electrodes.

It is another object of this invention to provide a means for diagnosing illness in vivo, as opposed to the current manner of diagnosing illness from in vitro markers, i.e. post-mortem, from frozen brains and body organs.

It is another object of this invention to provide a telemetric method of diagnosing dynamic release mechanisms of biogenic chemicals such that a human patient may be continuously monitored without the impediment of wires.

It is another object of this invention to describe peaks representing biogenic chemicals and neurotransmitters which have heretofore not been described and which influence behavior.

It is another object of this invention to provide a means for automating the in vivo monitoring of an animal or patient.

It is another object of this invention to provide neurochemical profiles from different brain regions, providing a neurochemical mapping device for diagnosis.

Unexpectedly, the inventor has found that a vast number of biochemical reactions produce a large number of biogenic chemical species heretofore unknown and undetectable. Using the method of this invention, it has now been found that semiderivative (semidifferential) voltammetry can be used for measuring concentrations and an instantaneous readout of rates of release and/or reuptake of biogenic chemicals in vivo in a reliable and repeatable manner according to the method of this invention. More particularly, it has been found, also unexpectedly, that the current produced by biogenic chemicals when monitored by a semiderivative electrochemistry device is only measurable by circuitry which provides a cathodic current. Thus, the, method of this invention relates to the measurement of a current produced in the body of an animal or a human being, the signal of which is processed by a cathodic current vis-a-vis previous circuits which are anodic. This permits the measurement of stable reduced and oxidized species in vivo with a cathodic current, heretofore inconceivable.

The method of this invention is particularly well-suited to measuring biogenic chemicals in vivo, that is, in a living animal or human being, although this method can be used to measure such chemicals in vitro. It was previously thought that biochemical reactions, in vitro, and quintessentially in vivo could only be measured by anodic currents. However, using the method of this invention, one can routinely detect oxidized and reduced species, with cathodic currents, expanding the range of detection considerably for the field of diagnosis in pharmacotherapeutics and medicine.

The present invention pertains to electrodes; an electronic circuit arrangement, which includes the electrodes, acting as an electrochemical cell to effectuate a cathodic (reduction) current in vivo, in vitro and in situ, which can be faradaic in nature; methods for using the circuit; and methods for making the electrodes. In situ is defined as taking a specimen of living cells, or an organ containing living cells, from a body and analyzing the specimen in a glass, or similar vessel. An example of an in situ specimen is a Pap Smear. The cathodic current can be derived from an electrochemical cell; the cathodic current with semidifferential voltammetry is unknown within the current concepts of brain neurophysiology and in vivo electrochemical reactions. The cathodic current serves as a specific detector for recognizing electroactive materials (and even non-electroactive materials with the use of antibodies) for biomedical diagnosis of diseased states, vis-a-vis healthy states. Cathodic analysis and detection of reversible and irreversible reduced or oxidized compounds, directly applicable to pharmacotherapeutics in biomedical research, were heretofore precluded.

BRIEF DESCRIPTION OF DRAWINGS

FIG. 3A depicts a graph drawn according to conventional electrochemical format wherein the axis indicating anodic (oxidation) current points downward and the axis indicating positive voltage points to the left. FIGS. 3B and 3C depict semiderivative voltammetry signals drawn according to nonconventional format, wherein the axes indicating anodic (oxidation) current points upward and the axes indicating positive voltage points to the right.

FIG. 7 is a representation of the results of the signal obtained using the method of this invention of endogenously released striatal dopamine and serotonin in acutely and chronically diabetic rats. Results are expressed as percent change from endogenously released dopamine and serotonin in the non-diabetic rat, matched for age, sex, food and weight. Bars represent the mean values derived from six to eight rats.

FIG. 8 is a representation of the signals, obtained from using the method of this invention, of rat striatal extracellular dopamine in hypoxic hypoxia using the method of this invention. Results are expressed as percent change from basal extracellular dopamine in the same animals under normal and abnormal conditions of $O_2$ (oxygen) availability. Bars represent mean values derived from six rats.

FIG. 9a represents a semidifferential voltammogram showing basal dopamine and serotonin release from rat striatum in vivo prior to treatment with dynorphin. FIG. 9b represents a semidifferential voltammogram showing dopamine and serotonin release from rat striatum in vivo after pharmacological manipulation with dynorphin (1–13) 1.5 mg/kg administered subcutaneously. The figure uses nonconventional electrochemical notation.

FIGS. 28(a) and 28(b) are computer programs to direct a modified Bioanalytical System (BAS) brand DCV5 detector or similar detectors to scan for oxidation or reduction currents in vivo (Computer Program 1) and in vitro (Computer Program 2), dependent on the type of electrochemical technique used.

FIGS. 29(a) and (b) are schematic diagrams of (a) a generalized operational amplifier circuit and (b) an operational amplifier integrator.

FIG. 31 represents: FIG. 31(a) A semidifferential voltammogram showing the dopamine (DA) signal on the first trial of, microelectrode conditioning (preconcentration) in phosphate buffer containing 5 uM of each of dopamine (DA), serotonin (5-HT), 5-hydroxyindoleacetic acid (5-HIAA), 3-4 dihydroxyphenylacetic acid (DOPAC), uric acid (UA) and ascorbic acid (AA). This is a stearate (1.24 cc Nujol) microelectrode.

FIG. 31(b) A semidifferential voltammogram showing the 5-HT signal on the first trial of electrode conditioning (preconcentration) in phosphate buffer containing 5 uM of each of DA, 5-HT, 5-HIAA, DOPAC, UA and AA. This is a stearate (1.24 cc Nujol) microelectrode.

FIG. 31(c) A semidifferential voltammogram showing no signal in phosphate buffer having a pH of 7.4 with no added chemicals. This is a stearate (1.24 cc Nujol) microelectrode.

FIG. 40 is a semidifferential voltammogram obtained from the analysis of NE and 5-HT, in phosphate buffer, using DA-pretreated graphite stearate electrodes. The dashed line represents 5 uM NE and 5 uM 5-HT. The solid line represents 5 uM NE and 1 uM 5-HT. The stearate (1.24 cc Nujol) graphite microelectrode was used.

FIG. 44 is a schematic diagram of a working electrode.

DETAILED DESCRIPTION OF THE PREFERRED EMBODIMENT

The method of this invention involves implanting, preferably, three electrodes in the body, preferably the brain: a reference electrode, an auxiliary electrode and a working or indicator electrode. The reference electrode provides a zero voltage point. The auxiliary electrode maintains the current, with a potential control operational amplifier, providing a sort of "ground" insofar as "drift" is eliminated, which maintains the voltage applied between the working and the reference electrode as a constant within the time limits of detection. The working or indicator electrode is used to vary the electrical potential with respect to the reference electrode.

The current signal emitted by any biological system is produced by the charge flowing, or current, between the reference and working electrodes. The current varies dependent on the electrochemical reactions taking place within the organ or suborgan. The signal is preferably processed with at least two operational amplifiers, one for the indicator, a current measurer, and one for the reference, a follower operational amplifier, processing the current between the two electrodes. The semiderivative circuit is an electrochemical circuit which is added to a circuit for linear scanning. The semiderivative circuit is made up of a series of ladder networks of resistors (from about 2 kilohms to about 2 megohms) and capacitors (from about $5 \times 10^4$ to $5 \times 10^{-2}$ microfarads) which process the current signal as the analog of the first one-half derivative of the undifferentiated signal. The resistive capacitive network that produces the semidifferentiated signal is described in detail in "Semiintegral Electroanalysis: Analog Implementation", *Analytical Chemistry*, vol. 45, No. 1 January 1973, by Keith Oldham, which is hereby incorporated by reference.

The novel circuitry of this invention provides the production of a reduction, or cathodic, current, which allows detection of both reduced and oxidized species heretofore undetected and precluded within these detection limits.

Figure 1:
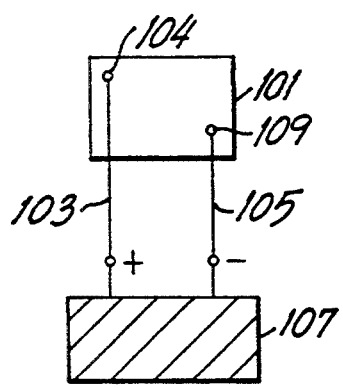
FIGS. 1 and 2 are schematic representations of two circuits which can be used in attempting to establish a semidifferential voltammetric signal.
Figure 2:
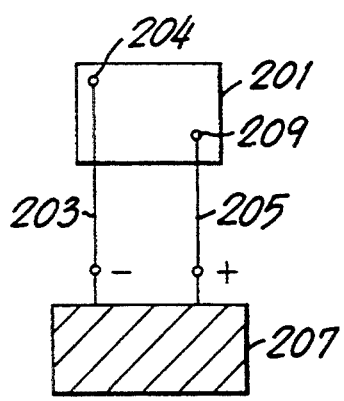

The electrodes should be situated in such a way as to accommodate a cathodic, or reduction, current from, for example, the brain. The electrodes can be situated in any specific region, such as the striatum, tuberculum olfactorium or nucleus accumbens. FIG. 1 shows a very simplified schematic view of the circuitry as it should appear in accordance with the method of this invention. The semiderivative circuit, 107, is connected to the brain, 101, via two leads: the brain lead, 103, attached to the working electrode, 104, and the reference lead, 105, which is attached to the reference electrode, 109. The current being emitted from the brain is a cathodic current, positive for reduction. Thus, in order to obtain a reliable measurement, the positive terminal of the voltammetry control should receive the emitted current signal from the brain lead which is attached to the working electrode. No signal would be produced if the leads were connected as shown in FIG. 2, which is the circuit configuration which would conventionally be expected to measure current generated by biogenic brain species. In FIG. 2, the working electrode 204 is shown implanted in the brain, 201. The brain lead, 203, is connected to the working electrode and the negative terminal of the semiderivative voltammeter, 207. This system, which produces anodic current, does not generate a recognizable signal. Ultimately, a cathodic current must be produced.

Conceptually, the indicator electrode of this invention is an inert surface which serves as an electron source or sink. The indicator electrode can be placed in specific parts of an organism or suborganism for diagnosis of diseases which range from mental and neurological problems to aging processes and malignant cervical cancers and other types of cancers, for example. As the potential is applied, the electrons from molecules or molecules of biogenic chemicals near the electrode surface can either gain electrons from the body, or source (cathodic reduction) or lose them to the indicator electrode sink (anodic oxidation). The current is dependent on the number of molecules which undergo electron transfer at the electrode surface; this is an accurate indication of the increase of species concentration in solution, in addition to an accurate assessment of the rate at which electricity is moved across the electrode and converted into charge. An instantaneous readout of rate is a unique feature of electrochemistry; this reflects in vivo release and/or reuptake mechanisms.

Figure 11:
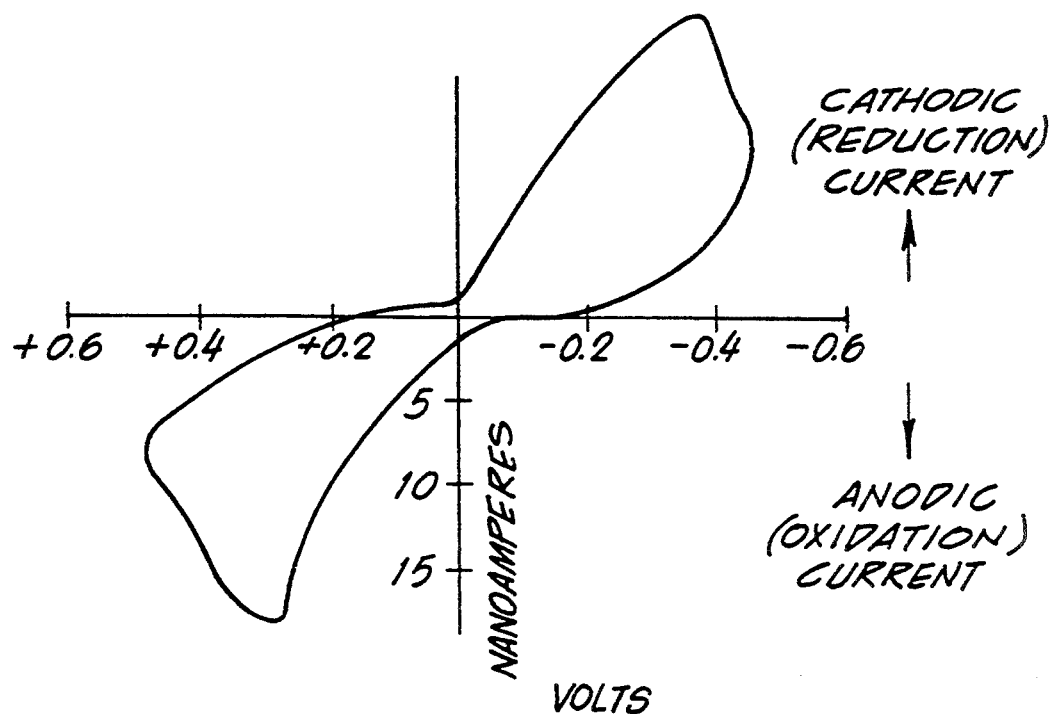
FIG. 11 is a representation of a typical linear scan cyclic voltammogram for a reversible redox reaction by electrochemical convention.

For the purposes of illustration, parts of FIGS. 3, 11 and ff. (and the following) are provided to delineate the conventional means for interpreting electrochemical measurements with the use of drawings according to electrochemical convention. By conventional electrochemical notation, oxidation (anodic) currents are plotted downward and cathodic (reduction) currents are plotted upward (See FIG. 11).

Figure 12:
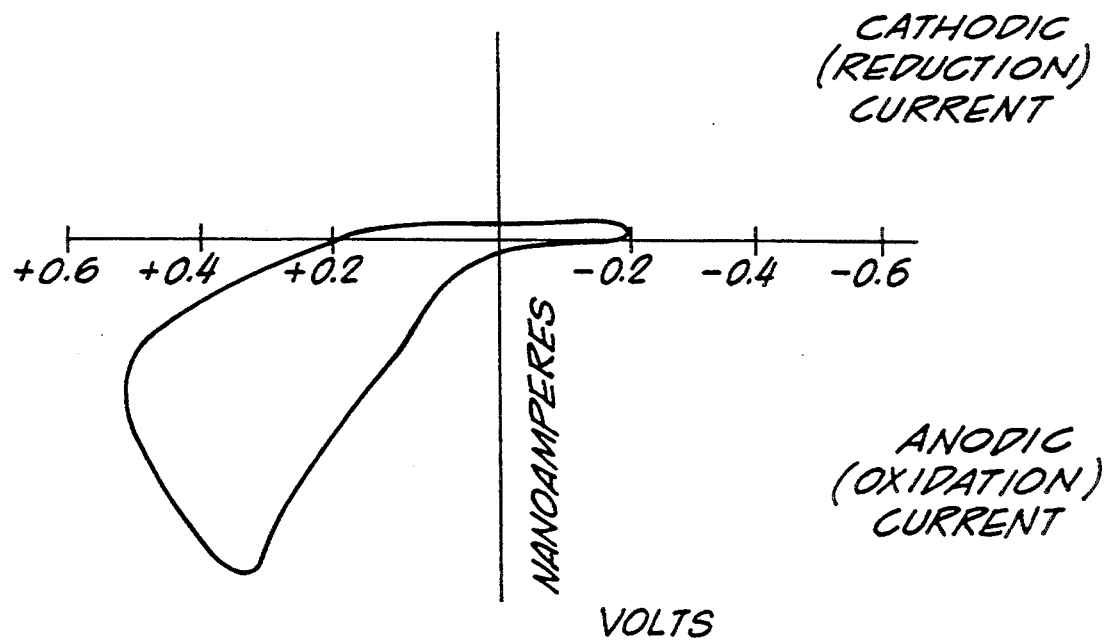
FIG. 12 is a representation of a typical linear scan cyclic voltammogram for an irreversible redox reaction producing a stable oxidized species only.

In the brain, in specific areas such as caudate, cerebral cortex and hippocampus, some biochemical reactions are irreversible in that they do not yield reproducible stable species, in range. This is indicated by the lack of reduced species on the reverse half cycle, as shown by FIG. 12, a linear scan cyclic voltammogram.

Figure 13:
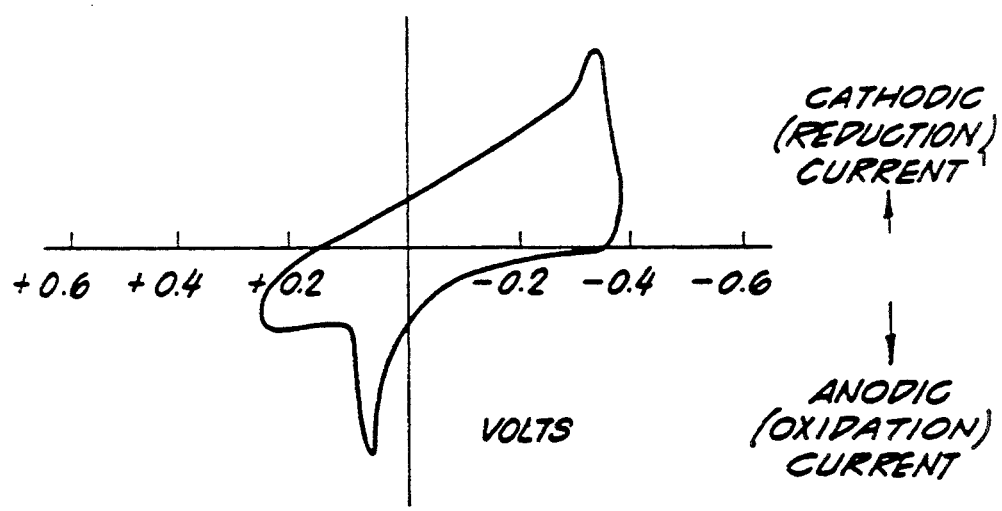
FIG. 13 is a representation of a typical linear scan voltammogram producing stable reduced and oxidized species.

Some organic material shows reversibility in brain tissue such as the oxidation-reduction behavior of injected 6-hydroxydopamine (60HDA) and the injected quinone 6-hydroxyquinone (60HQ). This reversible reaction produces both stable reduced species (60HDA) and stable oxidized species (60HQ). FIG. 13 illustrates this reaction as a linear scan. Peaks appear at the voltages at which these species are, respectively, reduced and oxidized. This is an example of the use of the apparatus of the prior art to measure by oxidation current.

The application of a potential, between 0 and +1000 mv, tests for stable oxidation species; application of a potential between 0 and −1000 mv detects reducible species. This is a useful test to distinguish reversible from irreversible oxidation reactions in all types of electrochemical experimentation.

An electrical circuit for providing an output signal having a mathematical relationship in operation to an input signal can be semiintegrated or semidifferentiated, The semiintegration circuit consists of an electrical transmission line in the input to the operational amplifier; the semidifferentiated circuit has such a line in the feedback loop of an operational amplifier.

Figure 14:
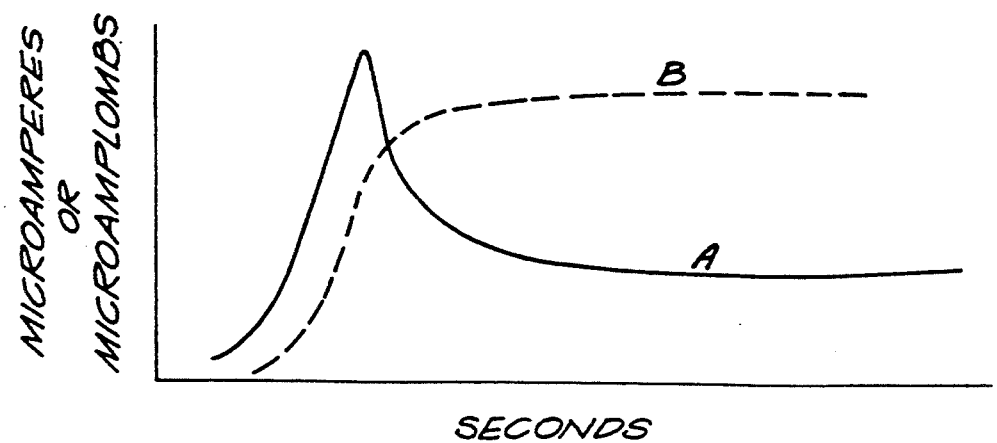
FIG. 14 is a representation of semiintegrated and semiderivative signals wherein curve A in amperes represents unchanged current and curve B in amplombs represents a semiintegrated curve, the latter providing for a longer lasting signal.

Semiintegral and semidifferential electroanalysis diminishes non-faradaic current by the addition of analysis time. A graph comparing results obtained from electroanalytical apparatus where the indicator (working) electrode current i(t) has been recorded (a) unchanged (Curve A in amperes) and (b) semi-integrated (Curve B in amplombs) is shown in FIG. 14. The amplomb measurement on the y axis is the sum of ampere $sec^{\frac{1}{2}}$ and coulomb $sec^{\frac{1}{2}}$. The full current curve (A) contains a preliminary peak followed by a falling off, making integration difficult. However, the semiintegrated curve (B) rises to a steady state value which can be used to determine concentration in dynamic levels because the signal lasts longer than that of linear scanning techniques.

It is postulated that, due to the speed at which the semiderivative circuitry is able to process signals, the reduced and oxidized species in the brain are detected using cathodic current according to the method of this invention. Conventional brain electrochemical scans have only processed oxidation currents. It is a novel aspect of this invention that cathodic reduction currents can be used to detect neurotransmitters and other chemicals in the brain and other sub-organisms.

The method of this invention describes a circuitry which can differentiate specific chemicals as biological markers of diseased states for purposes of psychotherapeutics, i.e. irreversible and reversible substances in the diagnosis of mental disease such as Alzheimer's and schizophrenia, mood disorders relating to diseases such as diabetes, and peripheral disease such as uterine or cervical cancer, diabetes, end the subsequent applications of the principles of telemetry thereof and the automation of the technique.

The method of this invention distinguishes semiintegral and semidifferential electroanalysis from other types of electrochemical analysis such as linear scan techniques within the concepts of cathodic and anodic currents. In the circuitry of the method of this invention, a cathodic (reduction) current is used to detect reversible and irreversible oxidizable and reducible species to delineate specific chemicals in disease vis-a-vis the anodic (oxidation) current taught in the prior art. Anodic currents taught in the prior art are unusable for semidifferential techniques in brain and other sub-organisms. They are unstable and not reproducible. Cathodic currents with semidifferential circuits are stable, reproducible and irreversible and not amenable to cyclic voltammetry. Another embodiment of the method of this invention would be the insertion of a differential operational amplifier to process the first derivative of the output current so as to provide a signal that would be cyclic in nature. This could also be a signal inversion circuit.

When monitoring the reaction of biological systems to the administration of a particular stimulus, such as a drug, a baseline value should first be obtained by measuring the current generated with respect to different potentials without the stimulus. The voltammeter is used to obtain a baseline value for certain biogenic chemicals by measuring the current generated from the brain with respect to the application of varying potentials or voltages. Different applied potentials can range from about −200 mv to about −1000 or from about 0 to about +1000 mv or any combination thereof may be applied. The scan rate, or rate at which the potentials are applied, is preferably in the range of about 5 to 30 mv-$sec^{-1}$, most preferably about 10 mv-$sec^{-1}$. Sensitivity, or amplification of the signal, can be in the range between about 0.1 and about 150 nAs$^{-\frac{1}{2}}$ inch$^{-1}$ volt$^{-1}$, preferably about 5-20 nAs$^{-\frac{1}{2}}$ inch$^{-1}$ volt$^{-1}$ in vivo and about 1-10 nAs$^{-\frac{1}{2}}$ inch$^{-1}$ volt$^{-1}$ in vitro. Preferably, for in vivo measurements, the temperature should be about body temperature, i.e. for mammals, 37.0° C. ±0.5° C. For in vitro measurements, the temperature of the phosphate buffer electrochemical cell should be from about 20° C.–about 25° C. It is important to remember that oxidation potentials can and will undergo lateral shifts dependent on temperature changes, time constant changes, and/or changes in resistance, capacitance and electrochemical parameters with time constants at any point or range between about 0.001 and about 10 seconds. Preferably, for in vivo measurements, the time constant is in the range from about 1.0 to about 5.0 seconds, most preferably about 5.0 seconds.

The reaction to the administration of stimulus can be measured after baseline values are recorded. After administration of the stimulus, potentials are applied and the current is measured with respect to the changing potentials. A comparison between voltammograms obtained prior to and after the stimulus will indicate the changes in production of biogenic chemicals and hence the presence of diseased states, which can even lead to bizarre behavior.

The method of this invention can be used for chronic studies, which take place over a relatively long time period, e.g. three to eight months and even longer, or for acute studies, in which values are taken over a short time period or only a few times or even once or during one study. The integrity of the electrode over a long time period is extremely useful and there is no problem discerning electrode placement in specific and minute areas of brain because of the neurochemical mapping profile described in this invention.

Preferably, the reference electrode used should be Ag/AgCl. The auxiliary electrode can be a platinum or a stainless steel electrode. Various modifications, however, may be made. The working electrode, which is also known in the art as a probe or sensor, if used for acute or chronic studies in a freely-moving animal, is preferably composed of a teflon-coated stainless steel microelectrode homogeneously packed with graphite paste, which is comprised of graphite and nujol or mineral oil or silicon oil. Most preferably the nujol has a specific gravity from about 0.8 to about 1. Commercial nujol typically includes DL-a-tocopherol as a stabilizer. A milliliter of nujol may contain up to 0.02 international units of DL-a-tocopherol. For the purpose of this specification, weight or volume of nujol means the total weight or volume, including additives which are typically in commercially sold nujol. The graphite paste also comprises an additional chemical compound which can serve as a modifier, selected from the group of complex lipids (e.g. acylglycerols, phosphoglycerides, sphingolipids and waxes) and simple lipids (e.g. prostaglandins, steroids and terpenes), glycolipids, lipoproteins, fatty acids such as, but not limited, to lauric acid, acetic acid, propionic acid, butyric acid, pentanoic acid, caproic acid, caprylic acid, capric acid, tridecanoic acid, pentadecanoic acid, hectadecanoic acid, nonadecanoic acid, myristic acid, palmitic acid, stearic acid, arachidic acid, lignoceric acid, palmitoleic acid, oleic acid, linoleic acid, linolenic acid, arachidonic acid, tuberculostearic acid, lactobacillic acid, elaidic acid, cerebronic acid, trans-hexadecenoic acid and the like, fatty acid derivatives, cerebrosides, and salts thereof.

The mixture should not come into contact with any substance other than an inert substance (for example, plastic, polypropylene and the like and glass) while it is being mixed or admixed. The graphite, oil and additional chemical compound should be in a container made of an inert substance and stirred or mixed with an implement made of an inert substance. For example, the graphite, oil and additional chemical compound could be in a glass container such as a mortar and pestle and stirred with a glass implement. The mixing typically occurs as the mixture is heated over a period of about 5 to about 20 minutes from a starting temperature of about 10° to about 25° C. to a final temperature of about 50° to about 55° C. Preferably the heating occurs from about 25° C. to about 55° C. Preferably the time period is from about 5 to about 10 minutes. The graphite paste can be used immediately after it is formed or it can be stored indefinitely. If it is stored, it should not be permitted to come in contact with any light. Typically, the graphite paste is stored for about 5 days–2 weeks prior to use to allow it to age. The graphite paste should be capable of being stored indefinitely as long as it remains impermeable to contamination with any other substance such as dust, etc., and light.

The microelectrode of the present invention can be used in any one or all of the techniques employed for in vivo electrochemical measurements including but not limited to square wave, amperometric measurements, semidifferential voltammetry, linear scanning, chronoamperometry, differential pulse and double differential pulse. The electrode made in this manner allows the subject to move without breaking the electrode. When the microelectrode is used for acute or chronic studies in an anesthetized animal, either glass or stainless steel teflon coated microelectrodes may be used. If it is desired to measure biogenic chemicals such as dopamine with or without the appearance of certain acids such as ascorbic acid or the dopamine metabolite 3,4-dihydroxyphenylacetic acid (DOPAC), or to measure serotonin (5-HT) with or without uric acid (UA) or 5-hydroxyindoleacetic acid (5-HIAA), the serotonin metabolite, and if it is further desired to have even greater selectivity, e.g., to determine norepinephrine selectively, the graphite paste should be modified. (Stearate modification has been shown to detect serotonin without detecting 5-hydroxyindoleacetic acid or uric acid in the same electrochemical signal or at the same oxidation potential) (Broderick 1986, 1987, 1988, 1989). Broderick, P. A., *Neuropeptides* 10 (1987) 369–386, Broderick, P. A., *Neurosci. Lett.* 95 (1988) 275–280, Broderick, P. A., *Brain Res.* 495(1) (1989) 115–121. Unmodified paste which is known, consists of graphite (carbon) and Nujol in a 3:2 ratio (Adams 1973). When paste is modified with an additional chemical compound, in accordance with the present invention, using stearic acid (stearate), for example, 0.7477 g graphite, 0.4503 g Nujol (extra heavy), 0.0502 g stearic acid are used. The weight ratio of graphite, oil and added compound or chemical can be in the range of, but not limited to, 0.15–7.5:0.1–5:0.01–0.5, respectively. Preferably the ratio of graphite weight ill grams: oil volume in cc's: compound weight in grams is 1.0 to 2.0:1.0 to 2.0:0.01 to 0.4, respectively; most preferably 1.0 to 1.5:1.14 to 1.34:0.01 to 0.10, respectively. The density of the oil typically ranges from 0.5 g/cc–2 g/cc.

Where arachidic acid (or less preferably stearic acid) is the modifying compound a preferable ratio is a weight of graphite in gms: volume of oil in cc's: and weight of acid in grams, respectively, of 1.0–1.5:1.14–1.34:0.10. More preferably the ratio is 1.0–1.5:1.19–1.34:0.10. Most preferably the ratio is 1.0–1.15:1.19–1.29:0.10.

Where the modifying compound is stearoyl cerebroside a preferable ratio is a weight of graphite in grams: volume of oil in cubic centimeter: and weight of cerebroside in grams, respectively, of 1.0–1.5:1.14–1.34:0.01–0.05.

Where the modifying compound is a mixture of arachidic acid and stearic acid in a 1:1 weight ratio, then the weight ratio of mixture is preferably 0.15 to 7.5 graphite: 0.1 to 5.0 oil: 0.01 to 0.25 arachidic acid.

Figure 35:
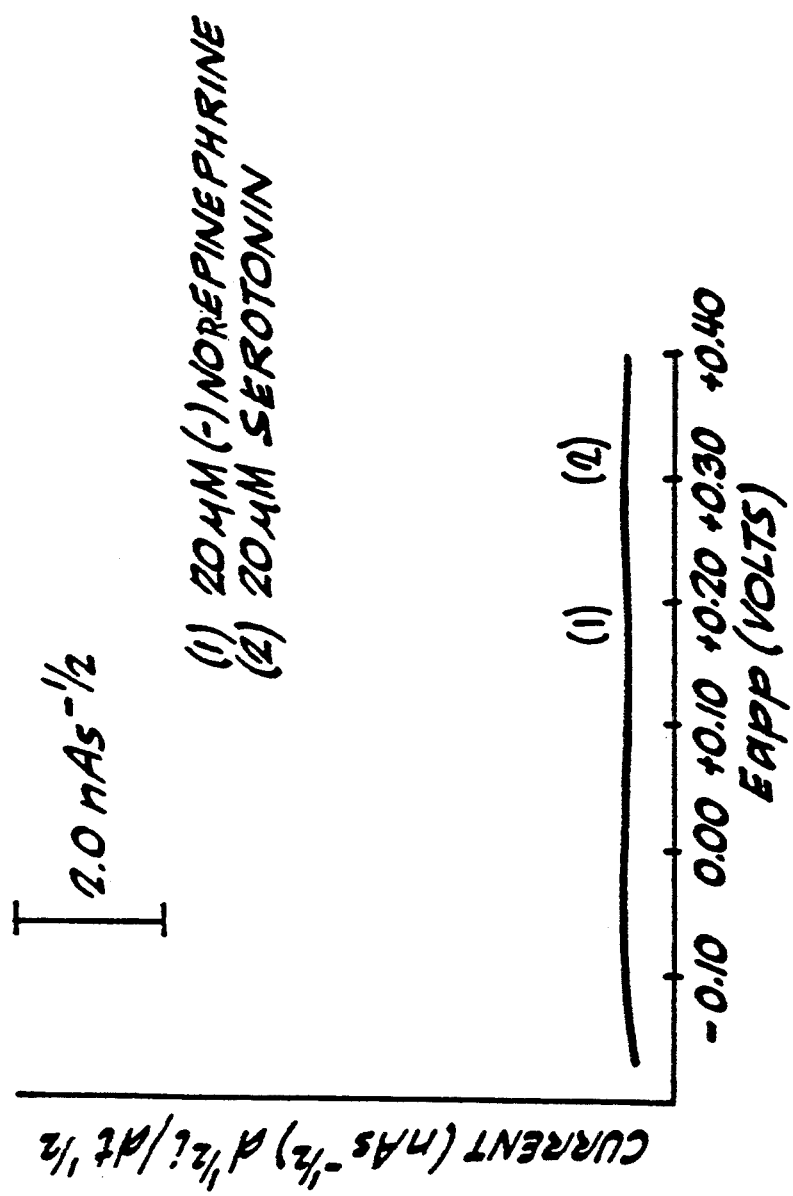
FIG. 35 is another semidifferential voltammogram which shows the behavior of the microelectrode when ratio of paste modification with stearate is incorrect. In this case, there was no significantly defined difference between norepinephrine (NE) and serotonin (5-HT) peaks. The semiderivative voltammogram is representative of the fourth electrode conditioning (preconcentration), at which time the 20 uM norepinephrine (1) peak and 20 uM serotonin (2) peak should be significantly defined when the correct paste modification is used.
Figure 36:
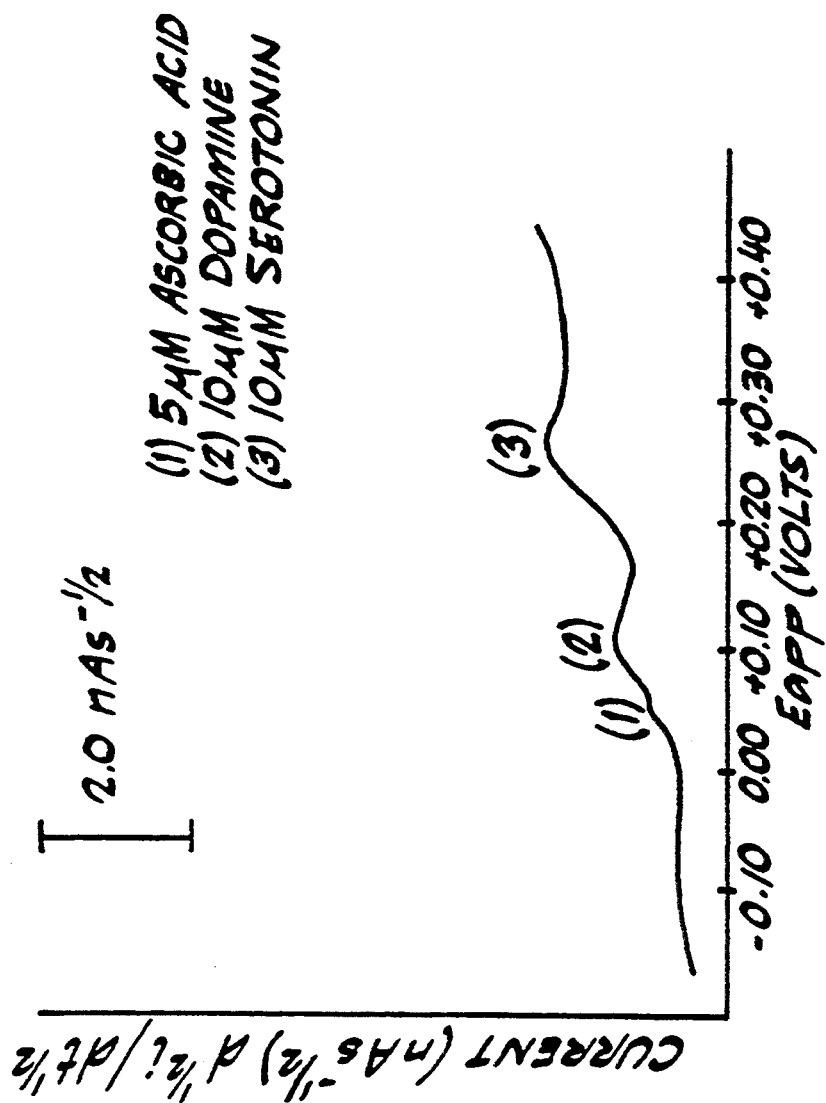
FIG. 36 is a semidifferential voltammogram which shows the behavior of the electrode when paste modification with stearate (1.24 cc Nujol) is correct. The semiderivative voltammogram is representative of a second microelectrode conditioning. The concentration of biochemicals [5 uM AA, 10 uM DA, and 10 uM 5-HT] is less than in FIGS. 34 and 35. Also, the number of conditionings is less. However, the voltammogram is correct and dramatically better than FIGS. 34 and 35. There is a clear, significant difference between the peaks of dopamine, serotonin and ascorbic acid.

The voltammogram shown in FIG. 35 is incorrect, came about by admixing 0.5072 g graphite, 0.4804 g Nujol (extra heavy), and 0.0526 g stearic acid. The density of Nujol may range from about 0.8 to about 1.5 gm/cc, preferably about 0.8 to about 1.2 gm/cc. Most preferably about 0.8 to about 1.0 gm/cc. Nujol is a type of mineral oil. Mineral oil preferably ranges from about 0.8 g/cc to about 1.2 g/cc. Silicon oil ranges from about 0.9 g/cc to about 1.2 g/cc.

Correct paste composition can and should be verified by combustion analysis and gas chromotographical analysis. Combustion analysis and gas chromatographical analysis were performed on 5 mg synthetic graphite stearate paste mixtures to determine the accuracy of the content of graphite and stearate acid. The graphite content was determined by combustion analysis and the stearic acid content was determined by gas chromatographical analysis. The level of Nujol can be calculated by the difference. These methods are important in the verification of paste composition.

It is noteworthy that another unexpected breakthrough in the distinction between the catecholamines, dopamine and norepinephrine has been accomplished with the stearate modification described in this invention (Broderick, P. A., Neurosci. Lett. 95 (1988) 275–280). These catecholamines are very important physiological brain neurotransmitters which oxidation potentials were too close in proximity to distinguish. We distinguish them here in FIGS. 38–42. Each of these catecholamines are involved in diseased states such as Alzheimers, sleep disorders, schizophrenia, drug abuse, anxiety disorders and others. Furthermore, one is more important than the other in specific disorders, e.g., norepinephrine may well be more important than dopamine in anxiety disorders.

Figure 38:
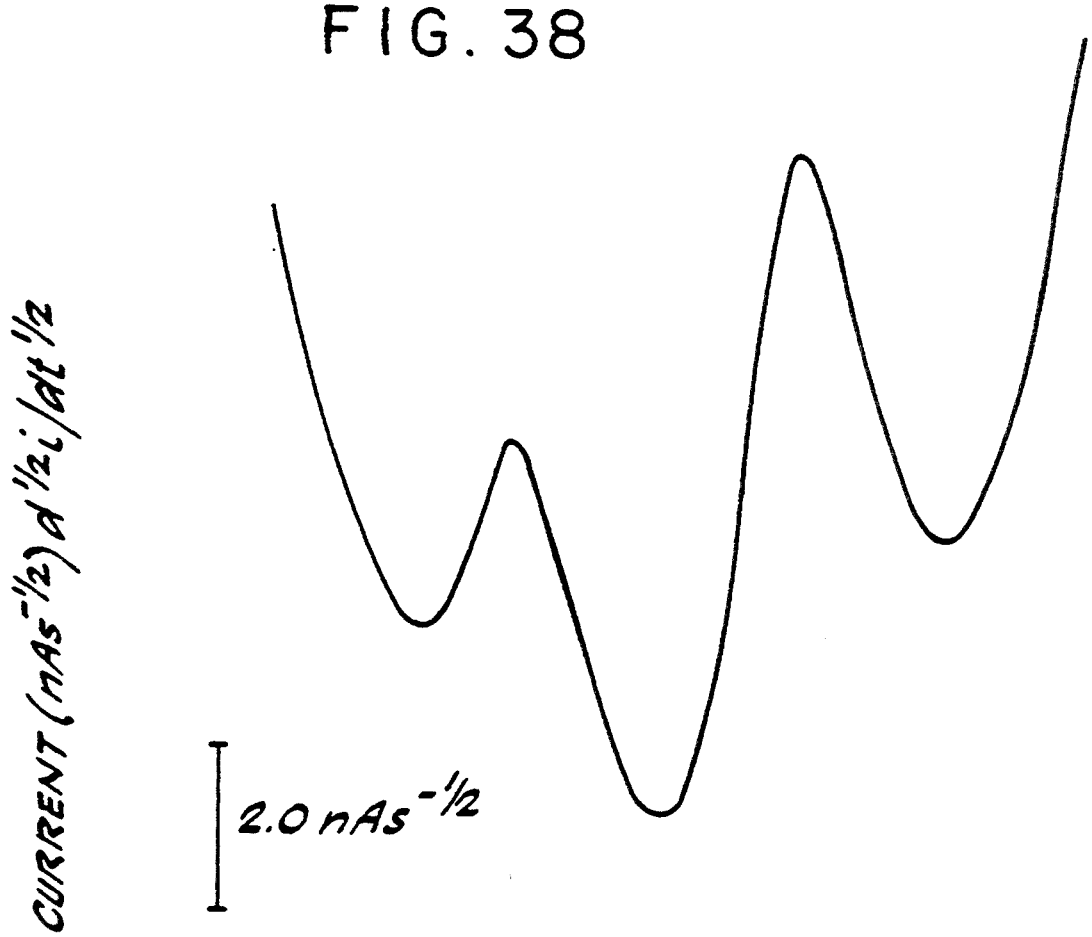
FIG. 38 is a semidifferential voltammogram obtained from the analysis of a solution of 5 uM of each of DA, 5-HT, DOPAC, 5-HIAA, AA, UA and HVA in phosphate buffer. Only DA and 5-HT are detected. Stearate (1.24 cc Nujol) graphite microelectrodes were previously exposed to extracellular fluid in the nucleus accumbens region of a rat brain, in vivo.
Figure 39:
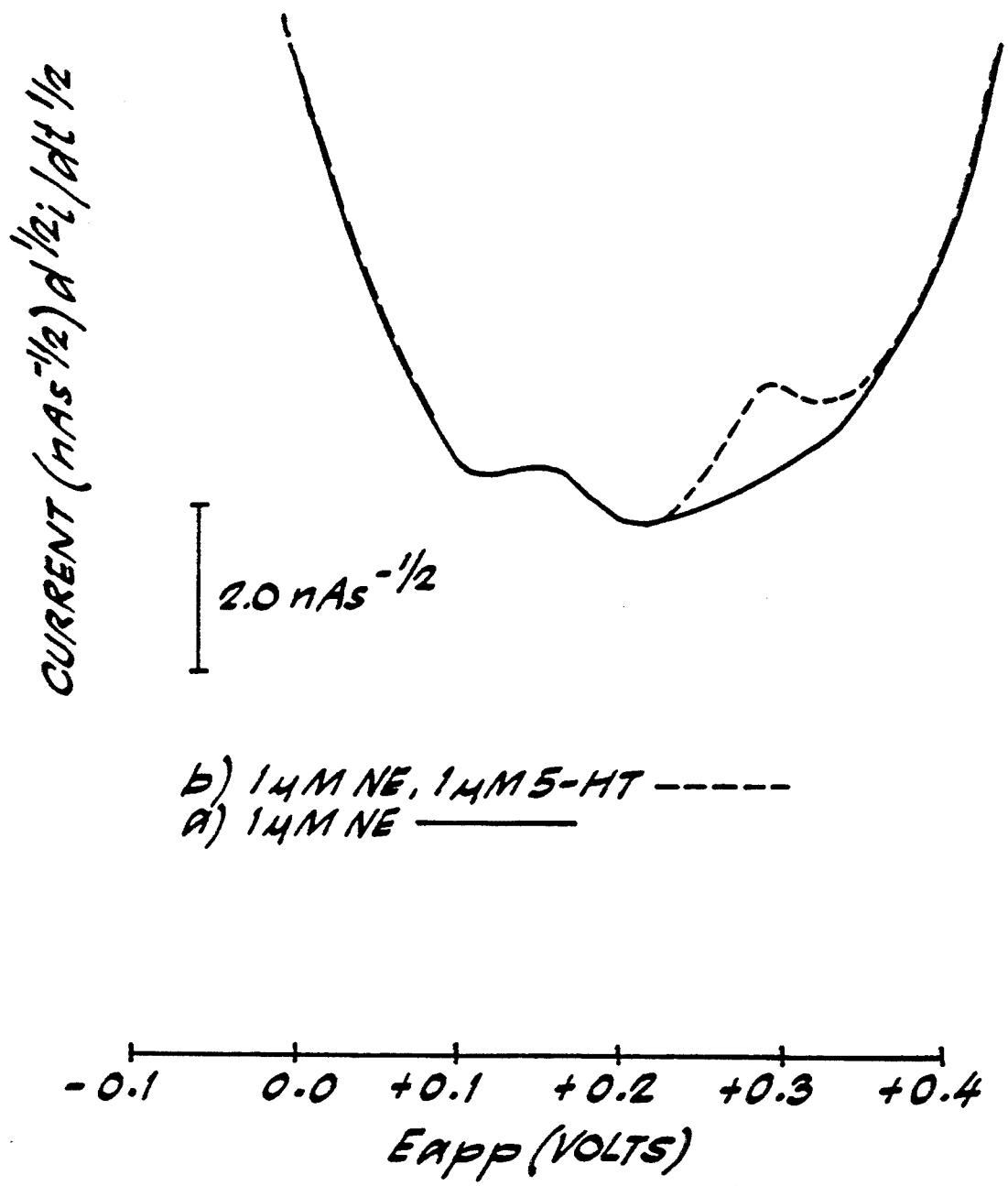
FIG. 39 is a semidifferential voltammogram obtained from the analysis of 1 uM NE and 1 uM 5-HT, in phosphate buffer. The stearate (1.24 cc Nujol) graphite microelectrode was used.
Figure 41:
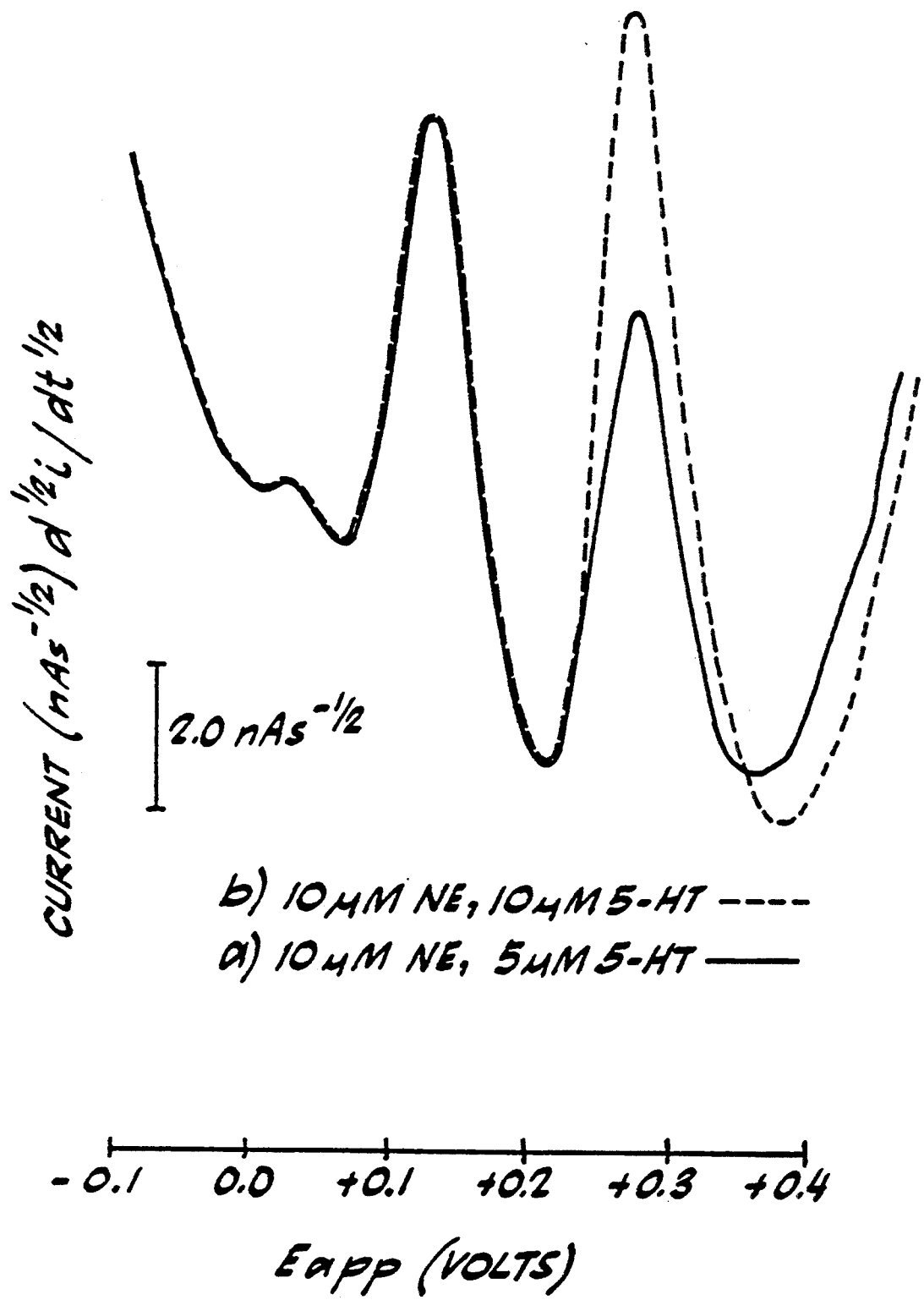
FIG. 41 is a semidifferential voltammogram obtained from the analysis of NE and 5-HT, in phosphate buffer, using DA-pretreated graphite (1.24 cc Nujol) stearate microelectrodes. The dashed line represents 10 uM NE and 10 uM 5-HT. The solid line represents 10 uM NE and 5 uM 5-HT.

A semidifferential voltammogram obtained from the analysis of a series of chemical tests with the graphite stearate electrode is shown in FIG. 38. Stearate graphite electrodes were exposed to DA, 5-HT, DOPAC, 5-HIAA, HVA, AA and UA. Only dopamine and serotonin were detected. Increasing amounts of DOPAC, 5-HIAA, HVA, AA and UA did not increase either the dopamine or serotonin signal. It should be noted that oxidation potential may shift laterally, dependent on concurrent shifts in pH, temperature, time constants, scan rate or resistance characteristics. The detection of norephinephrine (NE) and 5-HT, using graphite stearate electrodes in combination with semidifferential electroanaylsis, is shown in FIG. 39. The oxidation potentials are 0.155 V±0.015 V and 0.290 V±0.015 V, respectively. The electrochemical signal and oxidation potential remains the same for 5-HT no matter which catecholamine is undergoing testing. The electrochemical signal for the catecholamine NE, on the other hand, shows a different electrochemical signature from that electrochemical signal for DA. The oxidation potential for NE is 30 mV higher than that for DA. As concentrations of NE and 5-HT increase in amount, and if the electrode is pretreated with DA, the NE signature consists of a double peak. The earlier peak occurs at +0.030 V and the later one occurs at +0.140 V (FIG. 40). Notably, the later oxidation potential for NE is approximately 15 mV less than that for NE when the electrode is not pretreated with DA, and when sensitivity, scan rate, pH, time constants, resistance and other relevant parameters are exactly the same. Progressive and upward amounts of NE result in an increased double NE peak. This effect is shown in FIG. 41. The addition of 5-HT insignificantly increases the double peak signature of NE. Graphite stearate electrodes, which have not been exposed to the catecholamine DA, do not exhibit the double peak NE signature.

Figure 42:
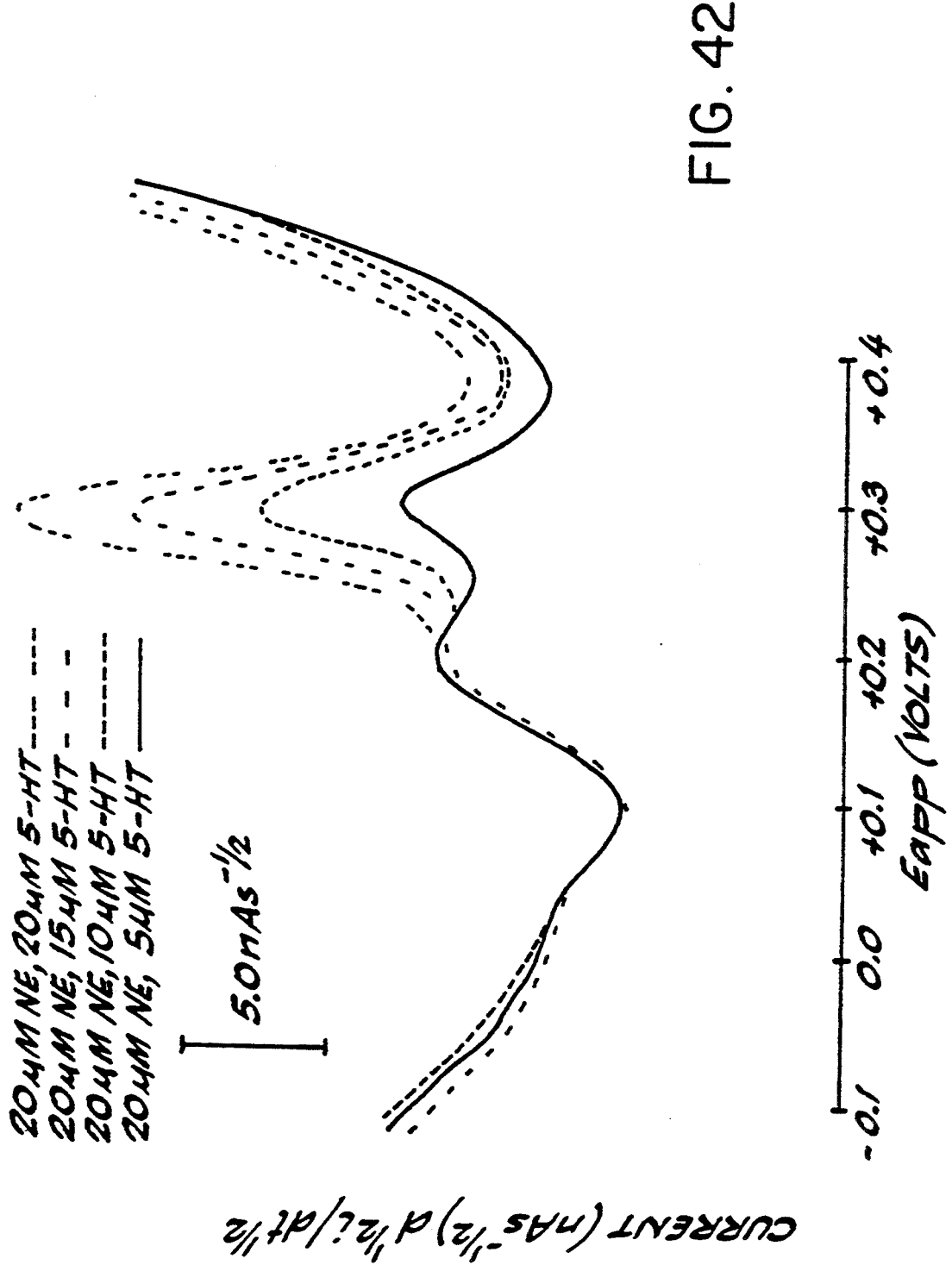
FIG. 42 is a semidifferential voltammogram obtained from the analysis of NE and 5-HT in phosphate buffer using DA-pretreated graphite (1.24 cc Nujol) stearate microelectrodes which were previously exposed to extracellular fluid in hippocampal CA1 brain region of rat, in vivo. The --- --- line represents 20 uM NE and 20 uM 5-HT. The - - - line represents 20 uM NE and 15 uM 5-HT. The ------- line represents 20 uM NE and 10 uM 5-HT. The _____ line represents 20 uM NE and 5 uM 5-HT.

Finally, a semidifferential voltammogram showing in vitro detection of NE and 5-HT, using graphite stearate electrodes, which have been exposed to hippocampus of rat brain, is shown in FIG. 42. 5-HT is detected without interference from its metabolite 5-HIAA and its purported contaminant, UA. The electrochemical signature for NE in vitro after hippocampal exposure exhibits a higher oxidation potential than that seen for prehippocampal exposure and displays the NE double peak. These electrodes were pretreated with DA before their implantation in discrete hippocampal rat brain CA1 regions. Graphite stearate electrodes, not previously exposed to DA before hippocampal CA1 insertion, do not exhibit the double-peak signature. Whether or not the stearate graphite electrode has been previously exposed to DA either in vivo or in vitro, the electrochemical signature of NE shows an oxidation potential for NE which is greater than that for DA. Importantly, when the stearate graphite electrode detects NE with an electrode that is pretreated with DA, the NE peak will be earlier than that seen for the detection of NE alone, yet later than that seen for DA alone. The signal for the combination of NE, DA, and 5-HT differs both from the DA-5HT combination and from the NE-5HT combination.

The coulombic efficiency of the graphite stearate electrode for NE vis-a-vis that for DA is similar. The graphite stearate electrode is 2- to 3-fold more responsive to serotonin than it is to the catecholamines, DA and NE, at equimolar concentrations. The interactive effects of 5-HT on the NE signal are again similar to the serotonergic effects on the catecholamine DA, i.e., increasing uM amounts of 5-HT insignificantly increase the catecholamine signal.

Summarily, the electrochemical signal for NE is approximately 0.03 V greater than that for DA. For graphite stearate electrodes pretreated with dopamine, the electrochemical signature for NE is a double peak. Given the caveat then, that all electrochemical parameters are the same, the NE signature will have an oxidation potential that is greater than that for DA, whether or not the electrode is DA-conditioned. These data may have relevance to neuronphysiological studies in vivo. It is entirely possible that the underlying principles can be extended to other types of electrochemical techniques in vitro and in vivo.

Blaha and Lane, in *Brain Research Bulletin*, Vol. 10, (1983) p. 861 have suggested modification with stearate but their report describes that detection of ascorbic acid is not possible with their assay. It is believed that the same kind of detection can be achieved using nafion-coated electrodes or other coatings known to those of ordinary skill in the art, Gerhardt, GA et al. *Brain Res.* 290 (1984) 390–395 [Adams, 1984].

However, the microelectrode described in the present invention overcomes these selectivity problems. The graphite and oil may also be modified with fatty acids (preferably other than stearic acid), fatty acid derivatives (including stearic acid derivatives), simple lipids, complex lipids such as sphingolipids and waxes, glycolipids, or lipoproteins. The microelectrode may be modified by a cerebroside, sphingosine, ceramide, galactocerebroside, sulfatide, cerebronic acid, psychosine, dihexoside, trihexoside, and tetrahexoside. The fatty acids differ in the complex lipids which contain backbone structure to which the fatty acids are covalently joined. Fatty acid modifications produce fine selectivity and specific fatty acid paste mixtures are stearic acid, arachidic acids, N-stearoyl-DL-dihydrophingosine, arachidic acid stearyl ester, stearic acid arachidyl ester and stearoyl cerebroside.

Various modifications on the indicator electrode can be made. The indicator electrode can be made a variable oxidant so that selectivity for anionic and cationic species can be made such that previously unidentified biological markers can be detected by electrostatic repulsion, electrocatalysis, catalysis or other means, between the electrode surface and the molecule of interest. Modifications other than the fatty acid derived modifications not specifically noted are not precluded.

Complex lipids have fatty acids, simple lipids do not have fatty acids. There are two kinds of fatty acids: saturated and unsaturated. Stearic acid is saturated and arachidic acid is saturated. However, stearic acid and arachidic acid can ionize to different extents when subjected to a given voltage and temperature. While not being bound by the following theory, these ionization differences appear to result in enhanced selectivity and amplification of sensitivity. Unsaturated fatty acids have lower melting points than do fatty acids. Unsaturated fatty acids have non-rotating double bonds. Thus they are very rigid. They may have a "receptor" type reaction at the electrode diffuse double layer.

Indeed, although strides in the delineation of electrochemical signals have been made in the past few years, there remains a gap in the present literature in the description of electrochemical electrodes, which involves the conventional electrochemical limitations regarding dopamine (DA), 3-4-dihydroxyphenylacetic acid (DOPAC) and ascorbate (ascorbic acid-AA). These problems exist insofar as these chemical substances have similar oxidation potentials and have not previously been readily discerned one from the other. Moreover, these problems exist insofar as the electrocatalytic regeneration of dopamine by the reducing properties of ascorbate are concerned.

Figure 37:
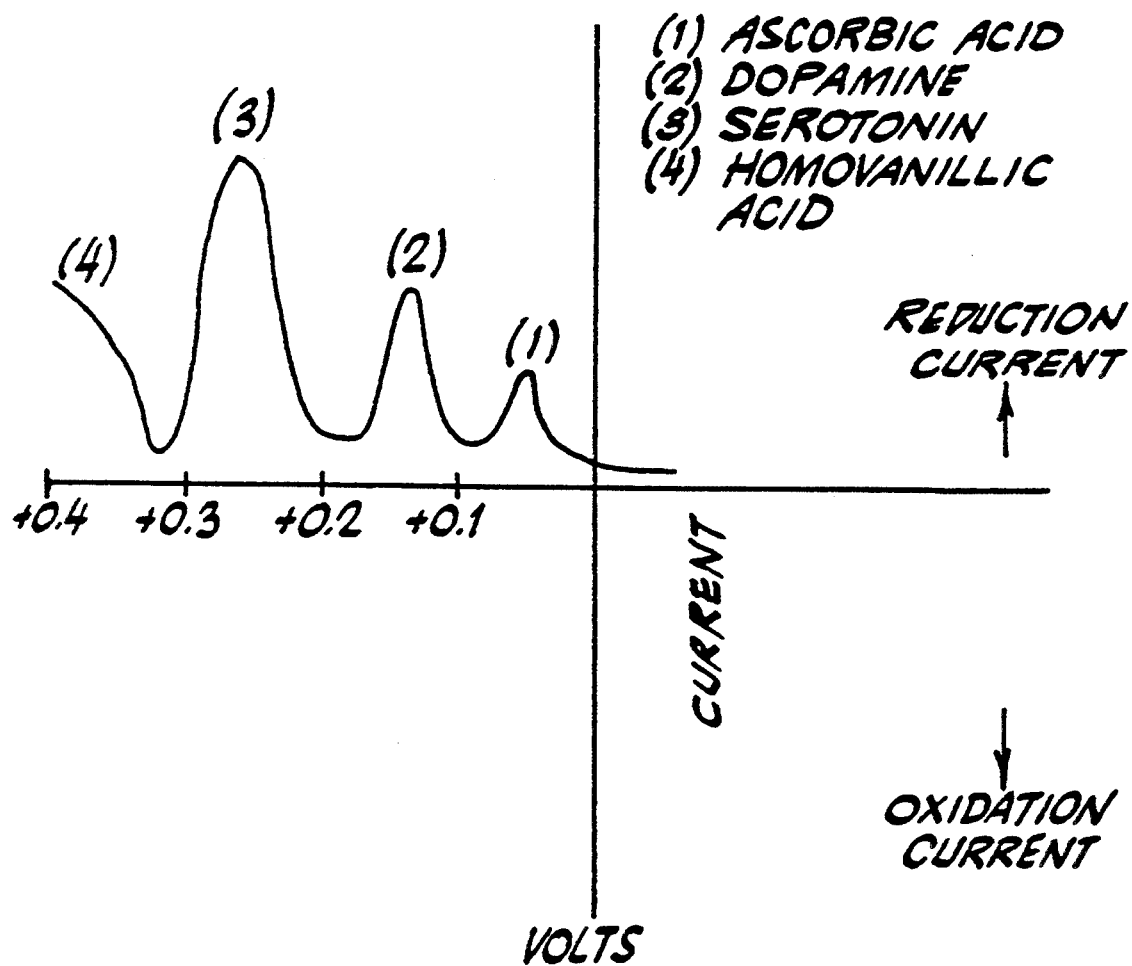
FIG. 37 is a semidifferential voltammogram showing a clear, significant difference between the peaks of ascorbic acid (1) and putative homovanillic acid (4), in addition to dopamine (2) and serotonin (3). This shows that ascorbic acid and putative homovanillic acid can be detected at high concentrations.

The present invention addresses the DA-AA-DOPAC question by defining and characterizing the stearate probe within the context of microelectrodes in vitro, in order to assist their use in electrochemical and neurophysiological studies. Additionally, the present invention addresses selectivity problems at indoleaminergic oxidation potentials, which are further positive than the catecholaminergic-ascorbate potentials. These are peak oxidation potentials at which serotonin, 5-hydroxyindoleacetic acid and uric acid can conceivably oxidize. The present invention describes semidifferential treatment of voltammetric data at small graphite stearate electrodes, in vitro. The findings show a distinct separate and simultaneous detection of dopamine and serotonin without interference from dopaminergic and serotonergic metabolites and other purported contributions to the dopamine and serotonin signal, i.e., ascorbic acid and uric acid. Ascorbic acid can be distinguished separately. This can be seen in schematic drawing FIG. 37.

Conditioning of the electrode in vitro is all important in the appropriate detection of the neurotransmitters and metabolites by electrochemical signals in vivo and in vitro. Indeed, brain fluid-adsorbed electrodes or brain treated electrodes, which can be inserted into the extracellular fluid of the brain to increase sensitivity need not be used because the conditioning process (described here) on the electrode inherently enhances sensitivity. Importantly, it should be noted that any residual current is not responsible for the enhanced sensitivity.

The purpose of the electrodes of the present invention is to permit detection and measurement of chemical concentrations that were unknown or less accurate prior to the present invention. However, prior to measuring unknown concentrations, the newly fabricated microelectrodes should be conditioned. Conditioning is important and heretofore unknown. Conditioning is important because it increases sensitivity of the electrodes for the biogenic amines and other neurochemicals with a controlled and studied manner so as to be able to achieve the best sensitivity before the experimental assay begins. Thus conditioning achieves accurate pre-and post-calibration data for extrapolation to release and/or reuptake of extracellular concentration of neurotransmitter in the brain synapse, in vivo, and/or other in situ or in vitro measurements.

Conditioning requires determining the peaks of known concentrations of the targeted chemical or chemicals in vitro in solution. To ensure that the voltammogram peaks of these chemicals will not be contaminated by other chemicals, the solutions employed for conditioning typically include metabolites of the targeted chemicals and other biogenic chemicals that may either naturally be in specimens that are in vivo, in situ or in vitro and/or may have similar oxidation potentials as shown by previous redox reactions or the like.

Conditioning occurs by exposing the microelectrode in vitro to a phosphate buffer solution containing the targeted chemical(s) as well as metabolites of these targeted chemicals and other biogenic chemicals having oxidation potentials similar to those of the targeted chemicals. Typically the oxidation potentials of these biogenic chemicals are in the range ±100 mV relative to the potentials of the targeted chemicals. The closeness of the oxidation potentials of the chemicals that should be in the conditioning solution depends on the electrochemical circuitry and/or the electrochemical characteristics of the electrode being tested. For example, conditioning an electrode for use with a semidifferential circuit, one should test for one or more biogenic chemicals having a potential in the range ±50 mV relative to the potential of the targeted chemical(s).

The solution of chemicals is employed for conditioning because these metabolites and close chemicals could affect measuring the targeted chemicals.

The conditioning typically includes three to five in vitro exposures of the graphite indicator microelectrode (modified as described above) to the solution of chemicals in a phosphate buffer. In the first exposure, the concentration of each of the chemicals is in the 25 nanomolar to 3 micromolar range and potential is applied and current is measured. In a subsequent exposure, the concentration of at least one of the chemicals in the mixture is raised to the 3–20 micromolar range and potential is applied and current is measured. In a further subsequent exposure the concentration of at least one of the chemicals is raised to be in the 19–200 micromolar range and potential is applied and current is measured. This set of exposures occurs over a 24 hour period. Then the set is repeated upon waiting at least 12 hours after the first set is completed. Optionally the set of exposures is repeated at least one more time, preferably one to four more times.

While exposing the graphite indicator microelectrode to this concentration, potential is applied to the graphite indicator microelectrode from −200 mV to +500 mV at a sensitivity of typically 2 nA/V. The potential is applied with the semidifferential circuitry shown in Example 15. However, electrochemical techniques other than semidifferential voltammetry may be employed. No ultraviolet light sources should be in close proximity to the phosphate buffer solution or stock solutions of target and close chemicals.

Conditioning of microelectrodes to detect dopamine and serotonin is described here as a process preferably including a set of five repeated exposures (of each newly fabricated microelectrode) to a solution of phosphate buffer containing DA (dopamine), DOPAC (3,4-dihydroxyphenylacetic acid), AA (ascorbic acid), 5-HT (serotonin), 5-HIAA (5-hydroxyindoleacetic acid) and UA (uric acid) in 1–20 uM concentrations in a 1, 5, 10, 15 and 20 uM final aliquot step protocol, before insertion into any discrete neuroanatomical or anatomical substrate.

In the first exposure, the electrode is typically exposed to DA, DOPAC, AA, 5-HT, 5-HIAA and UA in a 1 uM concentration. Other chemicals having oxidation potentials similar to dopamine or serotonin may also be employed. The exposures and application of potential are then repeated at the above-mentioned higher concentrations to achieve the above-mentioned five exposures. The five exposures are preferably conducted in one 24 hour period. Then twelve or more hours after the prior set of exposures is completed, the five exposures are repeated. Optionally the five exposures are further repeated at least one more time, preferably one to four more times. Each repetition occurs upon waiting at least twelve hours after the prior set of exposures is completed. The electrodes are stored in physiological saline before brain insertion.

FIG. 31(a) shows the detection of dopamine during a first conditioning experiment, using the graphite stearate electrode. FIG. 31(b) shows the detection of serotonin during a first conditioning experiment, using the graphite stearate electrode. FIG. 31(c) shows: the resulting voltammogram which occurs when only phosphate buffer and no other chemicals are present. The phosphate buffer for these studies is calculated in great detail in Example 13. In these experiments, dopamine and serotonin were dissolved in phosphate buffer in 5 uM amounts, simultaneously with 5 uM amounts of AA, DOPAC, 5-HIAA and UA. Sigmoidal curves, resembling plateaus rather than peaks, are commonly seen during the first conditioning experiment. The graphite stearate electrode should show no residual electrochemical response in phosphate buffer, even after the electrode is or has been previously exposed to amines and acids (Calibration unit $nAs^{-\frac{1}{2}}$, seen on FIGS. 31–43a, 45–50, denotes changes per axis of each voltammagram).

Figure 32:
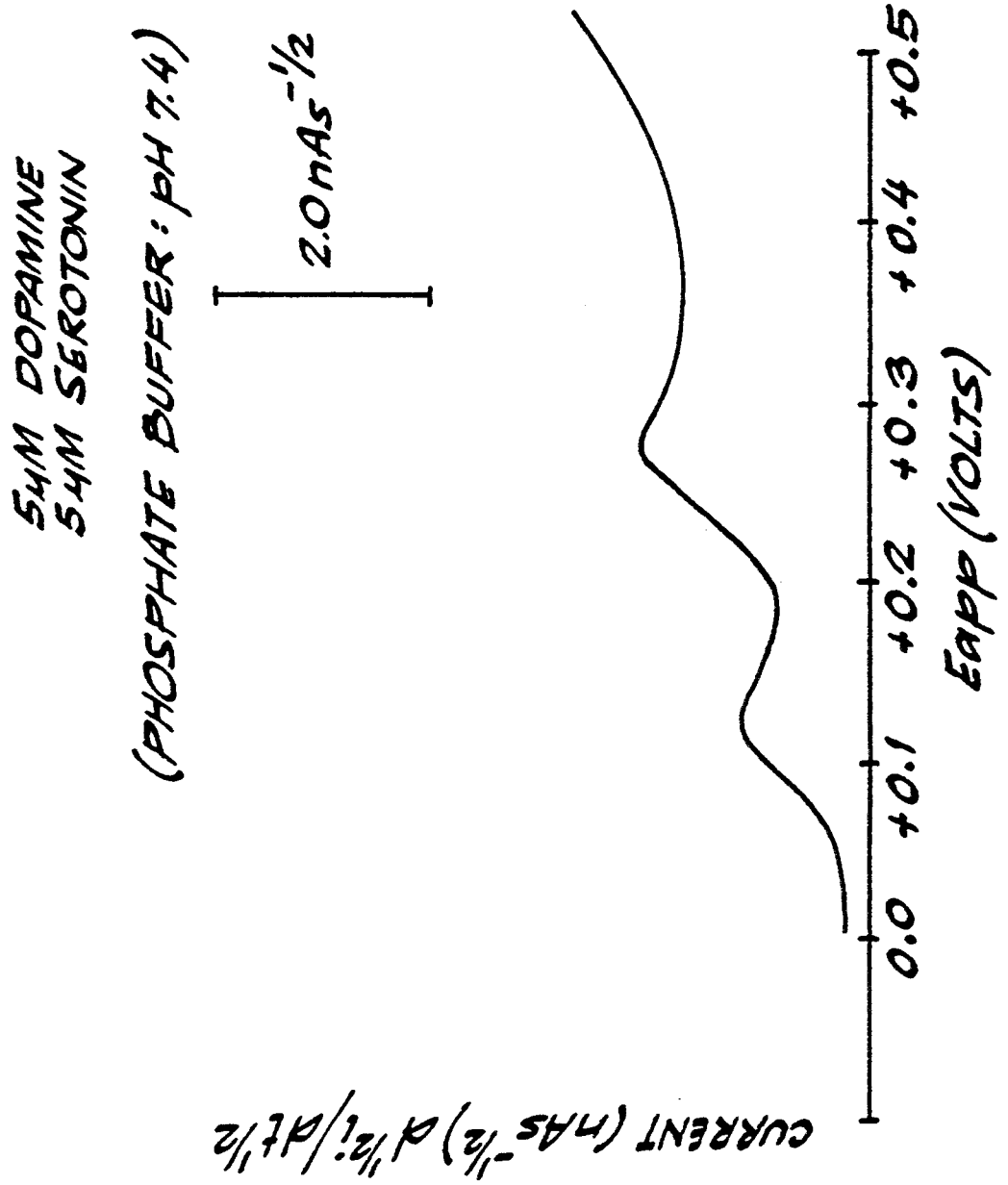
FIG. 32 is a semidifferential voltammogram derived from the graphite stearate electrode in phosphate buffer having a pH of 7.4 containing 5 uM of each of DA, 5-HT, DOPAC, 5-HIAA, AA and UA on the third trial of microelectrode conditioning (preconcentration). Only DA and 5-HT were detected. DOPAC, 5-HIAA, AA and UA, did not alter either the DA signal or the 5-HT signal. This is a stearate (1.24 cc Nujol) microelectrode.
Figure 33:
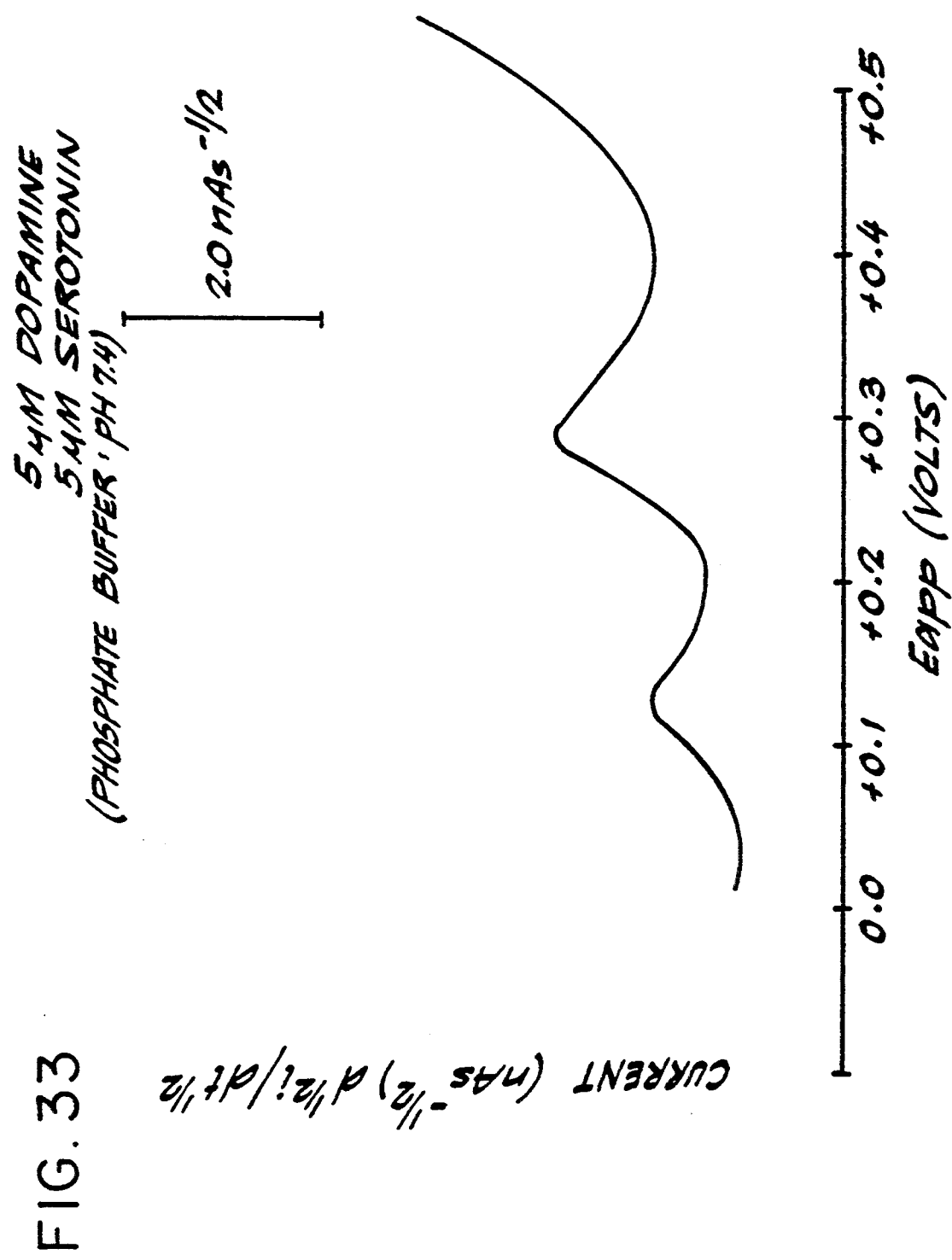
FIG. 33 is a semidifferential voltammogram derived from the graphite stearate microelectrode (1.24 cc Nujol) in phosphate buffer having a pH of 7.4 containing 5 uM of each of DA, 5-HT, DOPAC, 5-HIAA, AA and UA on the fifth trial of microelectrode conditioning (preconcentration). Only DA and 5HT were detected. Putative homovanillic acid (HVA) can be detected between 0.4 and 0.5 V. DOPAC, 5-HIAA, AA and UA did not alter either the DA signal or the 5-HT signal.
Figure 34:
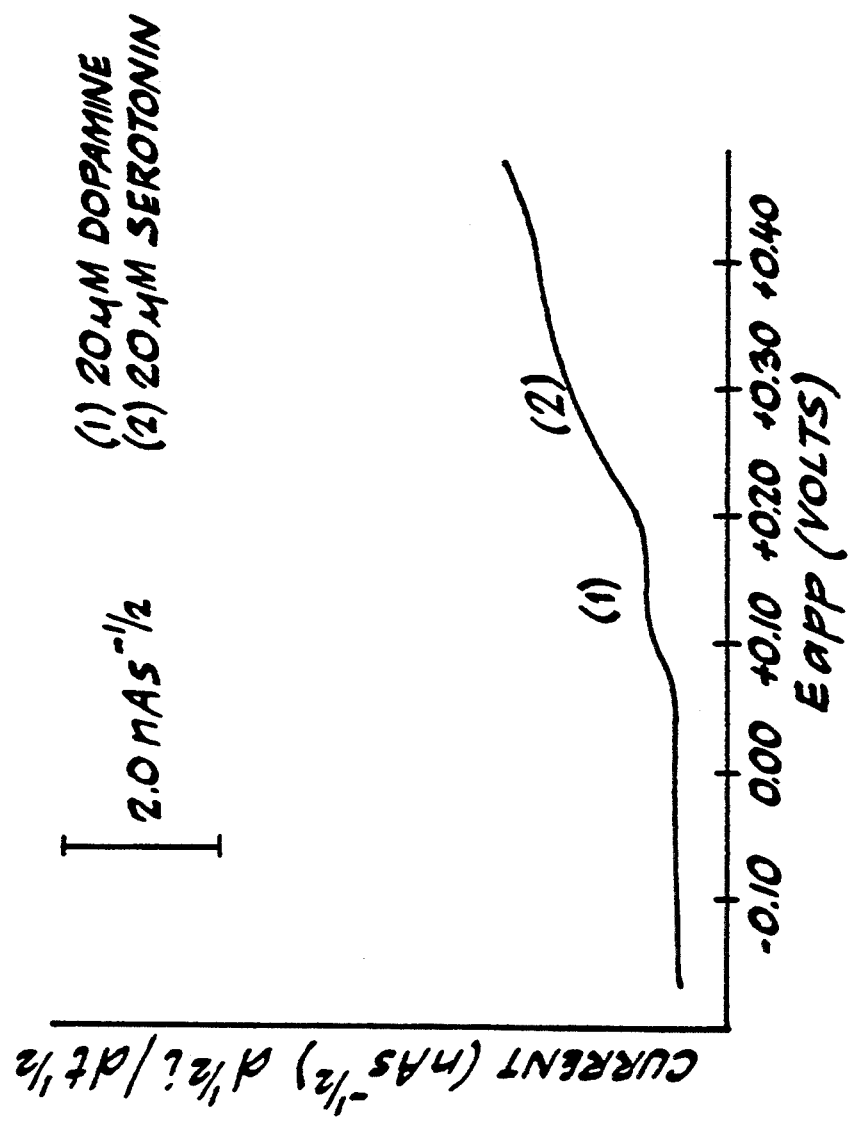
FIG. 34 is a semidifferential voltammogram which shows the behavior of the microelectrode when the ratio of paste modification with stearate is incorrect. There is no significantly defined difference between the dopamine and serotonin peaks. The semiderivative voltammogram is representative of the fourth electrode conditioning, at which time the 20 uM dopamine (1) peak and the 20 uM serotonin (2) peak are significantly defined, when the correct paste modification is used. Additionally, the ratio between peaks and the amplitude of each peak is incorrect.
Figure 43:
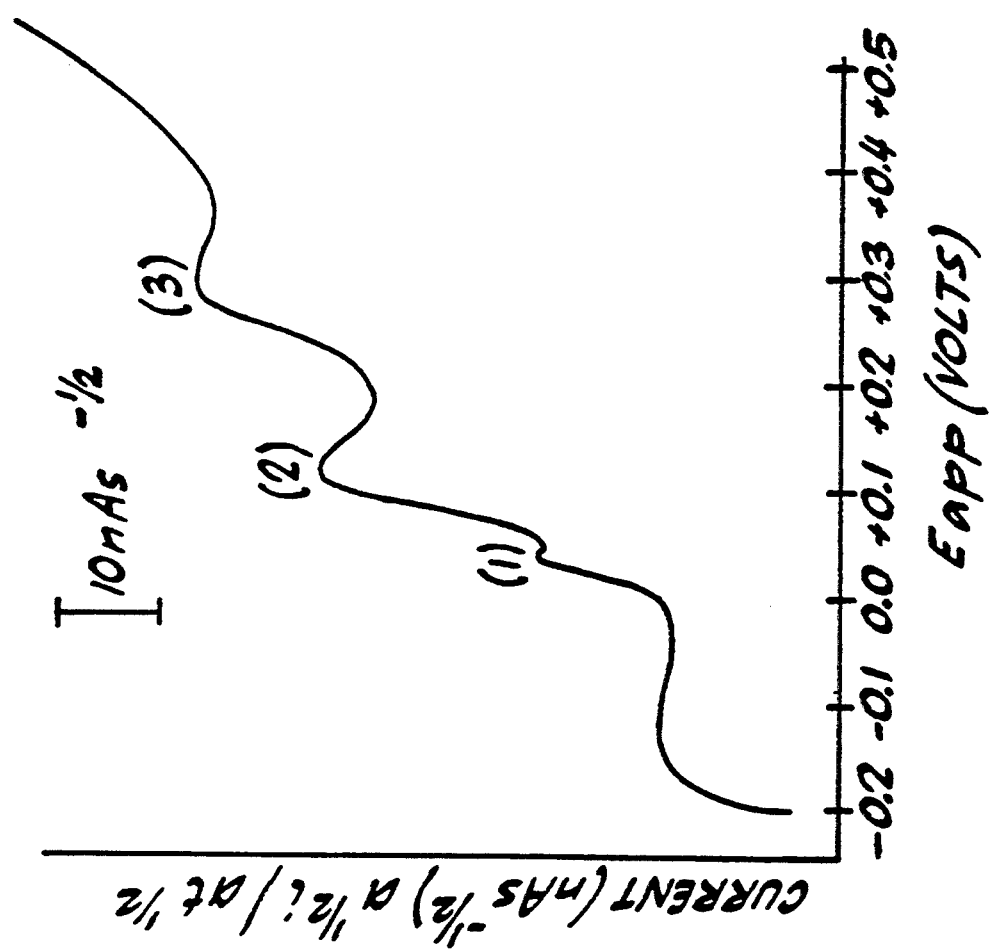
FIG. 43 is a semiderivative voltammogram showing the detection of ascorbic acid (1) (greater than 200 uM), dopamine (2) (greater than 200 uM) and serotonin (3) (greater than 200 uM) in phosphate buffer solution. At high uM concentrations of DA, 5-HT and AA, three clearly singular peaks occur.

FIG. 32 is a semidifferential voltammogram showing the detection of dopamine and serotonin with the graphite stearate electrode in phosphate buffer during a third conditioning experiment. The phosphate buffer contained 5 uM amounts of DA, AA, DOPAC, 5-HT, 5-HIAA, and UA. The peak height of each signal increased with increasing uM amounts of dopamine and serotonin, respectively. 3-4-Dihydroxyphenylacetic acid (DOPAC), homovanillic acid (HVA), 5-hydroxyindoleacetic acid (5-HIAA), ascorbic acid (AA)., and uric acid (UA) did not increase or alter the dopamine or serotonin signals. The graphite stearate electrode was unresponsive to 5-HIAA and DOPAC at any oxidation potential studied within the range of −0.2 v and +0.5 v. The graphite stearate electrode was not responsive to AA at the same oxidation potential as that for dopamine or serotonin. However, there was a response to AA, at an oxidation potential of +0.055 v ±0.005 v, at high uM concentration (FIG. 43). At low uM concentrations of AA, the response of the graphite stearate electrode to AA was insignificant or none at all (FIG. 33). Additionally, the coulombic efficiency of the stearate electrode to detect AA was dramatically less than that coulombic efficiency seen for the detection of either dopamine or serotonin. When low uM amounts of ascorbate and dopamine were simultaneously tested in phosphate buffer, no electrocatalytic regeneration of dopamine by ascorbate occurred. HVA is detected within an oxidation potential range from +0.4 to +0.5 v and/or approximately +0.42 v to approximately +0.49 v.

FIG. 33 is a semidifferential voltammogram showing the detection of dopamine and serotonin with the graphite stearate electrode in phosphate buffer during the process of fifth conditioning. The phosphate buffer contained 5 uM DA, AA, DOPAC, 5-HT, 5-HIAA and UA. The semidifferential voltammogram reflects a final conditioning experiment. Only dopamine and serotonin were detected. The oxidation potentials were within the expected range, i.e., +0.140 v ±0.015 v and +0.290 v ±0.015 v respectively. Additional amounts of DOPAC, 5-HIAA, AA and UA did not alter either signal. The caveat is noted that oxidation potentials for dopamine and serotonin can shift to the right or the left, dependent on differences in parameters such as temperature, pH, various resistance and capacitance characteristics, scan increments, frequencies, scan rates and time constants and other parameters.

Experiments in which final concentrations of 600 uM DA, and AA were pipetted into the 3-electrode phosphate buffer system in a 3 step, 200 uM aliquot protocol, showed that at high uM concentrations of AA and DA, 2 clearly singular peaks occurred for AA and DA. The AA and DA peaks were detected at oxidation potentials of +0.055 v ±0.005 v and +0.140 v ±0.015 v respectively. These data are seen in FIG. 43. No electrocatalytic regeneration of dopamine by ascorbate was seen at equimolar 200 and 400 uM concentrations of AA and DA. At 600 uM and DA, the dopamine peak was enhanced by approximately 10%. Data from preliminary experiments showed that UA was detected by the graphite stearate electrode, but at high uM concentrations of UA and at oxidation potentials higher than those needed to detect dopamine and serotonin. High concentrations of DA (200 uM) simultaneously tested with low uM concentrations of AA (20 uM) produced two clearly singular peaks. The AA peak was a spiked peak. The DA peak was broad. The reverse condition showed an ascorbate peak at 0.090 v. The peak resembled as an adsorptive prewave spike.

Thus, the present invention demonstrates that the graphite stearate electrode selectively detects dopamine at early positive oxidation potentials and selectively detects serotonin at later positive oxidation potentials, without detection of the possibly interfering chemicals, 3-4-dihydroxyphenylacetic acid (DOPAC), 5-hydroxyindoleacetic acid (5-HIAA), ascorbic acid (AA), uric acid (UA) and homovanillic acid (HVA) at the same oxidation potentials as those needed for the detection of dopamine or serotonin.

Conventional electrochemical wisdom dictates that DA, DOPAC and AA should oxidize at similar potentials. The ability to distinguish among these chemicals has been a major goal among electrochemists and neuroscientists for over a decade. The importance is felt in both in vitro and in in vivo studies since biochemical catecholaminergic and ascorbate reactions are essential in neurophysiological processes. The present invention shows that separation of dopamine, ascorbate and DOPAC waves are complete with the small graphite stearate electrode in vitro. When DA, DOPAC and AA are simultaneously tested, the ascorbate wave is detected at a potential, which is more negative than that needed to detect dopamine. AA is detected with low coulombic efficiency and generally high concentrations are needed for the AA signal to be detected. DOPAC waves are not detected at early oxidation potentials even at high concentrations. Significant electrocatalytic regeneration of dopamine, which can occur probably because of the reducing properties of ascorbate, is not seen.

The present invention addressed the problems of electrocatalytic regeneration of dopamine by ascorbate during the simultaneous exposure of these chemicals to the stearate microelectrode and the results were that an insignificant electrocatalytic regeneration occurred at high uM concentrations. Electrocatalytic regeneration of dopamine was first described by Adams. et al. In this reaction, ascorbic acid acts as a reducing agent to reduce dopamine-quinone back to dopamine, thereby enhancing the dopamine current. Wightman et al shows the electrocatalytic regenerative capacity of an electrode is directly related to the size of the electrode, i.e, at smaller electrodes, very little enhanced current is obtained. It appears that the concentration of species in solution may be a factor in the phenomenon of signal enhancement due to electrocatalytic regeneration as described by Broderick et al.

The stearate electrode responds to the detection of indoleamines at higher oxidation potentials than those oxidation potentials needed for the detection of the catecholamines. The coulombic efficiency of the electrode for serotonin, is two to three fold higher than that for dopamine. The better coulombic efficiency for serotonin is consistent with the adsorptive properties for serotonin. Although the exact mechanisms of the differences in the coulombic efficiency of the graphite stearate electrode for dopamine and serotonin need to be defined, other electrochemical processes, such as radial diffusion and slow scan rates, may be explanatory. The graphite stearate electrode of the present invention is not responsive to the detection of uric acid, at the same oxidation potential as that for dopamine or serotonin. The graphite stearate electrode will detect uric acid at high uM concentrations, at an oxidation potential of approximately +0.350 volts, which is beyond the oxidation potential needed for detection-of either DA or 5-HT. Thus, the microelectrodes as described in the present application are important because they enable spatially resolved chemical measurements in vitro and in vivo.

Electrodes may be constructed as follows, but their construction is in no way limited to the method described herein. The graphite paste mixture constituting the microelectrode of the present invention can be packed in an acceptable encasement therefor comprised of stainless steel or other acceptable metal or an inert material such as, but not limited to, plastic, Teflon, polypropylene and the like or glass. The stainless steel can be additionally encased by an inert material such as Teflon.

FIG. 44 shows an embodiment of a stainless steel indicator (working) electrode 117. The Teflon-coat 121 of the stainless steel indicator electrode 117 (tip diameter size approximately 150–200 u) can be pulled over the stainless steel to a length of approximately 500–750 u and packed with graphite paste 123. Thus, the steel 119 forms the base of a cylindrical well and the teflon 121 forms the walls of that well (teflon wall comprising the well is approximately 500–750 u in length) into which well the graphite paste 123 is packed. The term microelectrode is a relative one since the size of the brain varies from species to species. Therefore, the size of the electrode should be proportional to the size of the discrete anatomical area being studied in a given species.

Total diameter size of the microelectrode (including inner and outer diameter) could range from about 0.001 u–10 mm. Preferably, the diameter of the microelectrode is approximately $2\mu$ to 1 mm, more preferably $2\mu$ to $500\mu$. Another preferred microelectrode diameter range is $50\mu$ to 1 mm.

The length of the microelectrode should be sufficient to reach the desired neuroanatomical and other anatomical substrates and to prevent undue stress on such substrates.

The length of the microelectrode should be in such a proportion to the diameter of the microelectrode to prevent undue stress on the microelectrode itself.

An example of a graphite paste mixture that constitutes the microelectrode of the present invention and that can be packed into the cylindrical well described hereinabove is stearic acid (100 mg) mixed with 1.5 g graphite (carbon) powder in 1.24 cc extra heavy Nujol. Notable differences though may occur in the effects of of oils by weight and/or by volume. Potentials were applied to the indicator electrode between $-1000$ mv and $+1000$ mv.

The criteria for selection of appropriate indicator electrodes can be: (a) that the electrode showed at least 100 mv (current (nA)) deflection with about 10 uM DAHCL (dopamine hydrochloride); (b) that the paste composition presented homogeneously under a dissection microscope, 300×magnification. The potentials were measured with respect to an Ag/AgCl (1M NaCl) reference electrode.

The reference electrode can be fabricated by coating with chloride the entire length of a forty mm silver wire, previously coiled around an ⅛ inch drill bit. The chloride can then be coated in a 1M-NaCl solution for one-half hour at a current of 2 mA per electrode. The electrode is then equilibrated in fifty mL of a 1M-NaCl solution until the criterion for the reference electrode is satisfied, i.e. the potential difference between the fabricated reference electrode and a BAS reference electrode (not usable in brain) should not exceed 10 mv. More recently, 2.5 mv is a better criterion.

In addition, an auxiliary electrode, made of stainless steel, can be housed in combination with the reference Ag/AgCl electrode in a one ml Biotip brand pipette (Becton-Dickinson, Orangeburg, N.Y.), or, auxiliary and reference can be separately placed in contact with dura. A description of the reference electrode, as used in the brain of the freely moving animal is described as follows. The reference electrode is a Ag/AgCl reference electrode. The Ag/AgCl reference electrode is constructed by plating 10 mm silver wire (from Medwire Corp., Mt. Vernon, N.Y.) with AgCl in a 1M NaCl solution for about a half hour with the voltmeter (from Micronta) set at a current of 2 milliamps per electrode. The wire is then inserted into a 1.50 microliter capillary pipette (from Cole-Palmer Instrument Co., Chicago, Ill.) with 5% agar in physiological saline. The opening of the pipette is then shut off with absorbent cotton. An amphenol pin is soldered to the coated silver electrode at the other end of the pipette.

Preferably, the electrodes are implanted in vivo using a sterotaxic surgery device such as the David Kopf device. A David Kopf device consists of pairs of microscaled bars which allow the surgeon to implant the electrodes at the precise organ site desired.

The method of this invention may be used to measure biogenic chemical levels, release mechanisms or reuptake or reuptake inhibition mechanisms in synapses and extracellular fluid of both anesthetized animals or humans and freely-moving (unanesthetized) animals or humans.

The method of this invention may also be used to elucidate behavioral-determinants. By determining the levels of release or reuptake of biogenic chemicals and the changes in those levels, release or reuptake, while observing certain animal and human behavior, one can correlate the behavior patterns with the biogenic chemical alterations. This observation can contribute to the possible determinations of the causes of certain behavioral manifestations in all stages of life (neonatal, adult and aged), for example, brain reward/brain pain systems, euphoria, drug addiction, alcohol dependency, diabetes, self-administration studies, stereotypy, catalepsy, anti-anxiety or anxiety paradigms, turning behavior paradigms, reactions to environmental stimuli throughout life stages, conflict/avoidance paradigms, muricide, and other behavioral studies such as memory loss or brain injury, due to ischemia, stroke and other cardiovascular consequences.

The method of this invention can be used in vivo in applications involving any warm-blooded or cold-blooded animal possessing a brain or a primitive brain or type of brain and other organs of the body, such as a human, a primate, a lower mammal, reptile or squid. It is particularly well-adapted to observing the levels of biogenic chemicals in mammals, including human beings, which has been heretofore unachievable.

Telemetric measuring devices known to those skilled in the art may also be used to monitor current via radio and TV signals such that external electrodes need not be attached to a stationary source which would hinder movement of the subject during measurement. For example, the telemetric dual antenna described in U.S. Pat. No. 4,539,710 (Dinsmore) which is incorporated herein by reference may be used in the telemetric embodiment of the process of this invention for detection of electrochemical signals from the brain or other suborgans of animals and humans.

Figure 15:
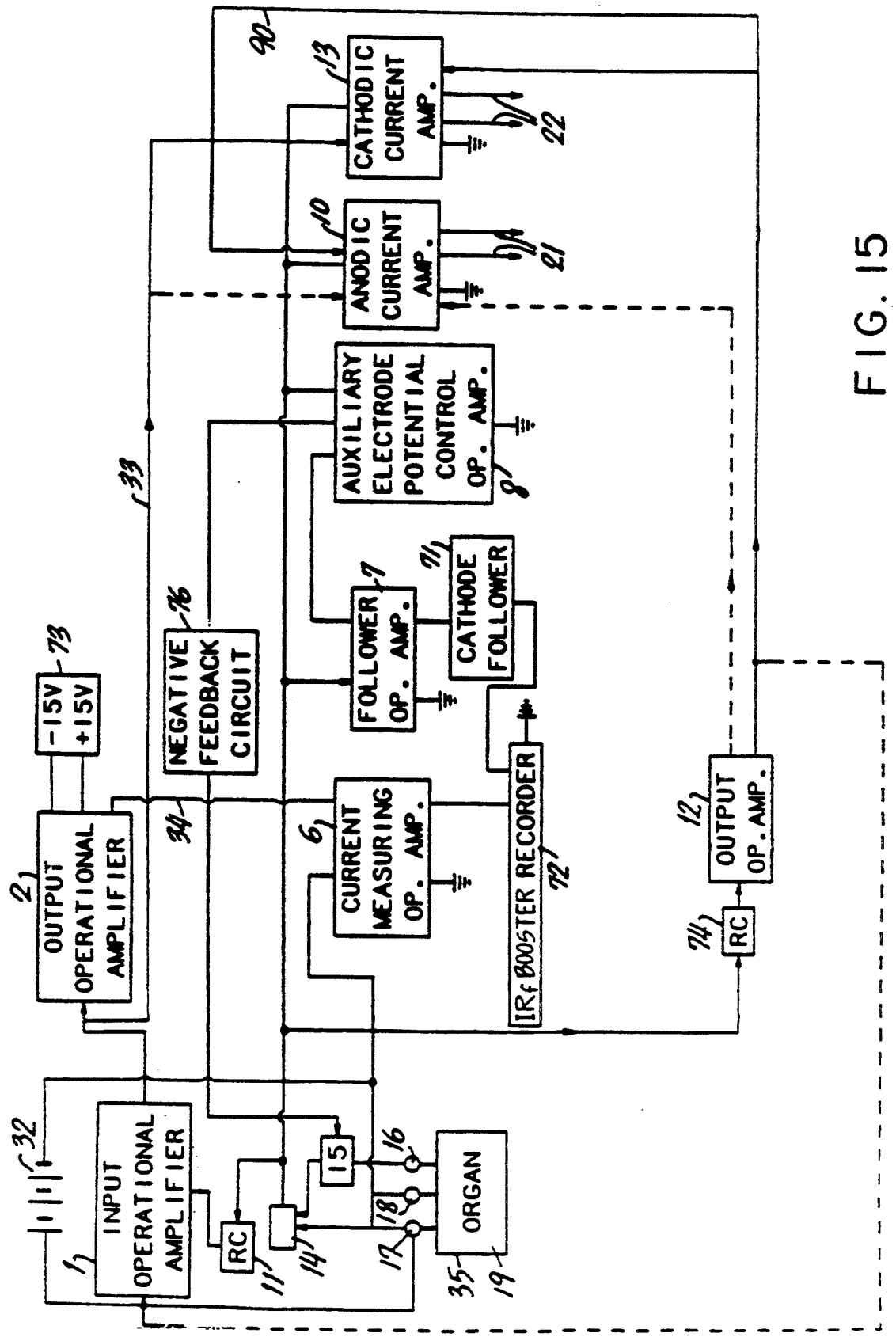
FIG. 15 is a schematic diagram illustrating an embodiment of a circuit arrangement according to the method of this invention. The diagram illustrates the circuitry for producing cathodic (reduction) currents to distinguish these from anodic (oxidation) currents which are used in other forms of electrochemical detection such as linear scan and chronoamperometry.
Figure 30:
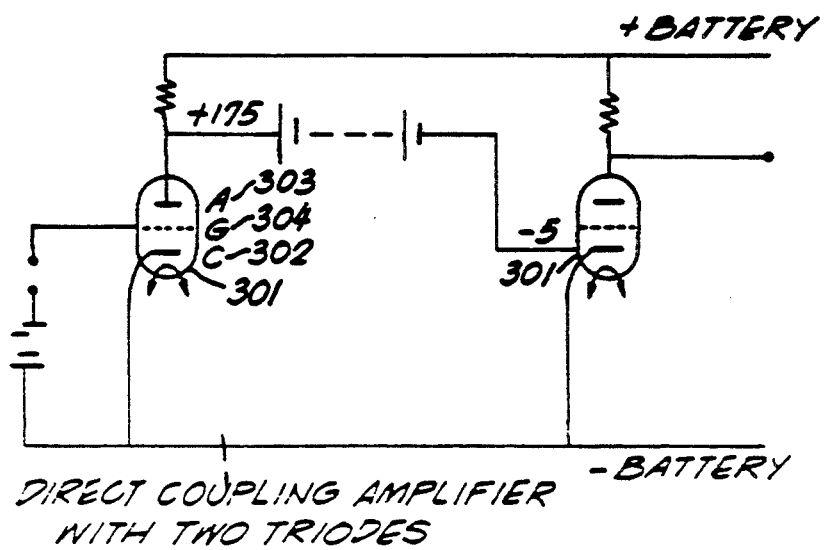
FIG. 30 is a schematic diagram of a direct coupling amplifier having two triodes.

The schematic diagram in FIG. 15 depicts the circuitry needed for the production of cathodic and anodic currents for semiintegral, semiderivative or semidifferential processing. An indicator electrode 17, reference electrode Ag/AgCl 16, and an auxiliary electrode 18 are connected to organ or sub-organ 19 and are connected to operational amplifiers, 14, 15 forming an electrochemical cell, 14–19. More specifically, operational amplifier 14 is connected between indicator electrode 17 and auxiliary electrode 18 and operational amplifier 15 is placed between reference electrode 16 and auxiliary electrode 18. The auxiliary electrode 18 and reference electrode 16 are placed in contact with the cortex or outer layer 35, of the organ or sub-organ. The indicator electrode 17 is inserted into the interior of the specific part of the brain or other suborganism which is the object of study. Battery 32 which provides an equal and opposite potential to that potential being measured is connected between the indicator electrode 17 and the reference electrode 16. A potentiostat (not shown) provides a known voltage against the electrochemical cell so that concentration changes at the electrode do not occur and so that no residual current will flow, causing an IR drop across the cell and changing the electromotive force. The circuit arrangement of the electrochemical cell, 14 to 18 is connected to operational amplifiers 6–8. The basic design of an operational amplifier is shown in FIG. 29. Operational amplifier 6 produces an analog signal proportional to tile current through the indicator electrode 17 which is processed through a semidifferential ladder network which can be and is received by the y-axis external measuring instrument such as a recorder, 72. Operational amplifier 7 receives the analog voltage signal proportional to the current between electrodes 16 and 17 and the current is processed through a cathode follower, 71, which may be plotted on the x-axis of any recording instrument or an oscilloscope 72. Operational amplifier 8 maintains a constant potential on auxiliary electrode 18 by means of a negative feedback circuit 76 (not shown in detail) which automatically corrects for any drift of the potential difference between the reference and indicator electrodes. In accordance with the invention, the electrochemical cell 14–19 is connected in series with direct coupling amplifiers 10 and 13, which can be triodes or pentodes examples of which are seen in FIG. 30. Transistor amplifiers or integrated circuit amplifiers could, of course, also be used. These amplifiers respectively produce anodic and cathodic currents emitted from the organ being studied. RC filters 11 and 74 filter out unwanted and transient surges in electrical output. The resistance capacitance complex amplifier resists an exponential decay of signal. It is expressed as a time constant, in seconds. The time constant in seconds can be varied so that different components of the signal can be detected and interpreted. Differential operational amplifiers 1 and 2 are a ladder network of resistors and capacitors for semidifferentiating the current produced by the electrochemical cell. As stated previously, ladder network amplifiers such as 1 or 2 are described in the Oldham work, incorporated herein by reference. Ladder network amplifiers 1 and 2 are used to semidifferentiate cathodic (reduction) currents for the purposes of delineating irreversible and reversible biological chemicals and the like for medical diagnosis. Operational amplifier 1 transmits an input signal to operational amplifier 13 which like amplifier 10 may be a triode as shown in FIG. 30. The signal is then transmitted to terminal output cables 22 for direct processing of semidifferential cathodic current. One aspect of the novel circuitry is the electrical connection 33 between amplifiers 1 and 13.

Figure 16:
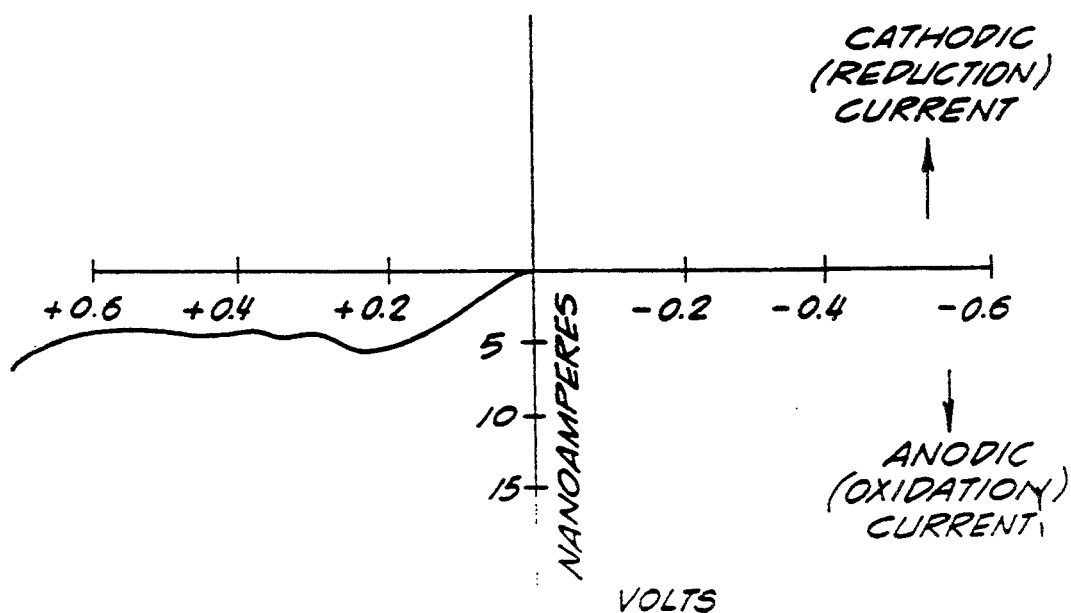
FIG. 16 is a diagram illustrating a linear scan voltammogram showing the production of biogenic chemicals using the conventional electrochemical notation.

Input operational amplifier 15 is connected between auxiliary electrode 18 and reference electrode 16 and to the input of output operational amplifier 12 through RC filter 74. Amplifier 12, which has an output connected to an input of cathodic current amplifier 13, may also optionally be connected so as to output to anodic current amplifier 10. Since amplifiers 10 and 12 have a linear gain, this arrangement will produce linear reproductions of the cathodic and anodic currents when a chart recorder such as 72 is connected to outputs of amplifiers 10 and 13. The linear scan is shown in FIG. 16.

Figure 10A:
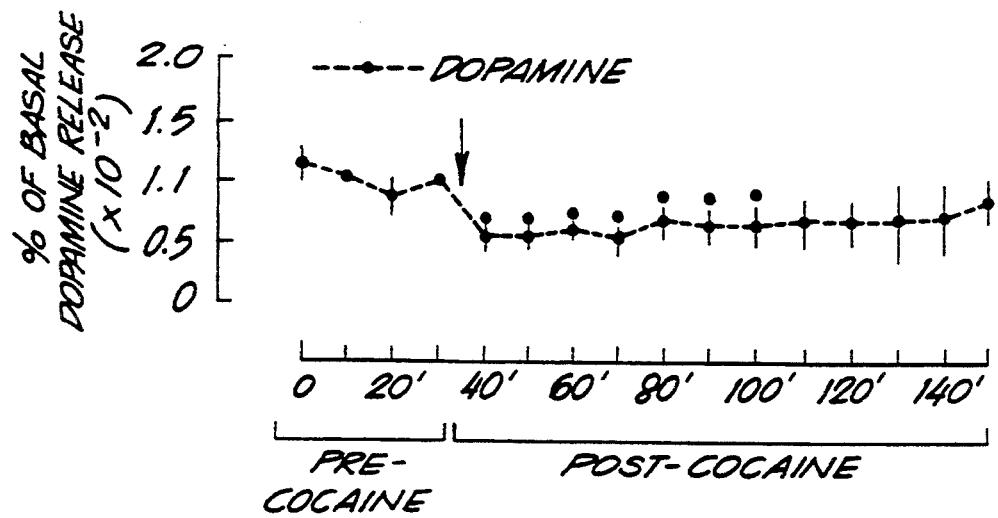
FIG. 10a illustrates a line graph showing the time course characteristics of the effect of cocaine (20 mg/kg injected subcutaneously) on dopamine release from rat striatum. The x axis represents time (in minutes) before and after the administration of cocaine. The y axis represents dopamine release as percent of control. The percent of controls were calculated by averaging the first four scans and dividing all values by that average.
Figure 10B:
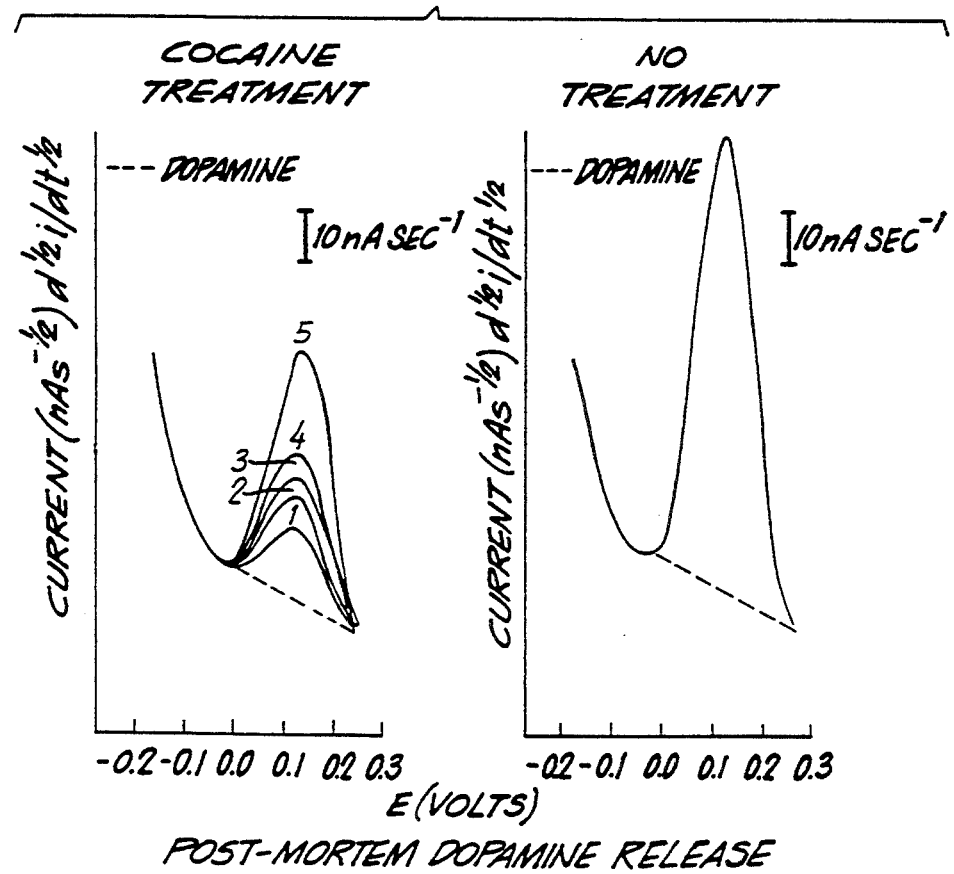
FIG. 10b illustrates semiderivative voltammograms showing post-mortem differences between dopamine release in cocaine treated (left voltammogram) and untreated animals (right voltammogram). The x axis represents increasing oxidation potentials in volts; the y axis represents current in nA $sec^{-1}$. The electrochemical signal for dopamine (1) represents dopamine release pre-mortem. The electrochemical signals for dopamine (2,3,4,5) represent dopamine release post-mortem, (ten minute intervals), in a cocaine treated animal. In contrast, the right voltammogram represents dopamine release ten minutes post-mortem in an untreated animal. The figure uses non-conventional electrochemical notation.
Figure 17:
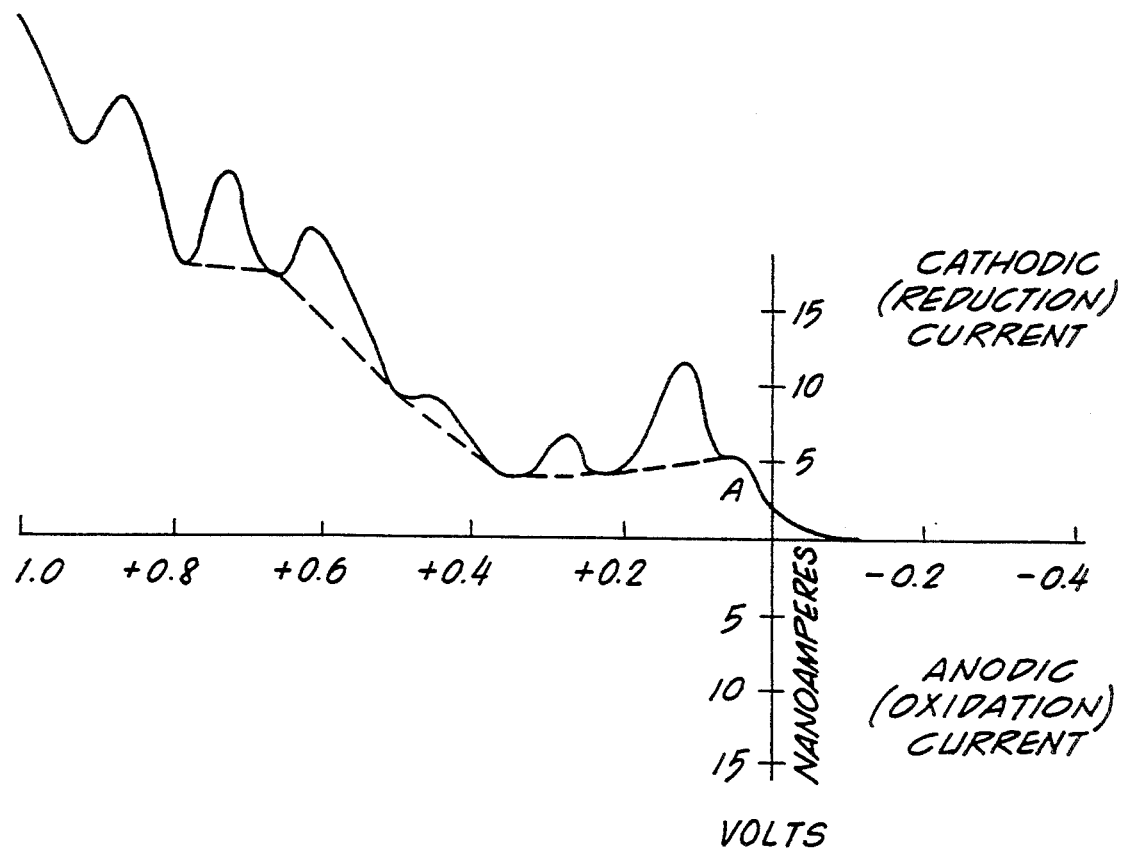
FIG. 17 illustrates a semidifferential voltammogram showing the production of biogenic chemical peaks at 150, 290, 520, 690, 790, 820 and 910 mv. This Figure illustrates the usefulness of the methods of this invention in medical diagnosis, as the peaks represent neurotransmitter and neurotransmitter-like peptides as detected by cathodic currents in accordance with the method of this invention with semidifferential processing according to the invention herein using conventional electrochemical notation and describing peaks not heretofore described.

Optionally, an output of amplifier 12 can be connected to an input of semidifferential amplifier 1 and then the output obtained from amplifier 1 can be connected to the input of amplifier 13 to result in a signal having a steeper slope of current versus oxidation potential as shown in FIG. 17. This signal has the advantage of more clearly defining the chemicals being analyzed and increasing the time for analysis as shown in FIG. 10b. The output of amplifier 2 can be directly connected to the y-axis of the recorder 72 by line 34.

Power supply 73, which is shown providing plus fifteen and minus fifteen volts to semidifferential amplifier 2, may also be used as a power supply for linear operational amplifier 12.

Alternatively, in place of the electrical connection between 1 and 13, a potential divider circuit with a triode or transistor selecting switch (not shown) can be used to direct the anodic current for non-differentiated and nonsemidifferentiated scanning techniques to triode operational amplifier 10 by connection line 90, in series with terminal output cables, 21. The potential divider circuit with an anode/cathode (triode) selecting switch can also be used to direct cathodic current for differentiated and semidifferentiated scanning techniques to the reduction amplifier, 13, in series with the terminal output cables, 22. An electrical connection line between amplifier 1 and triode 10, will provide results that are not confusing for currents that are non-differentiated. However, confusing results for current production that is differentiated or semidifferentiated will occur.

Preferably the circuit employs isolated grounds. Optionally, a Miniguard TM surge suppressor (static-magnetic voltage regulating transformer) from Jefferson Electric is employed.

Figure 19:
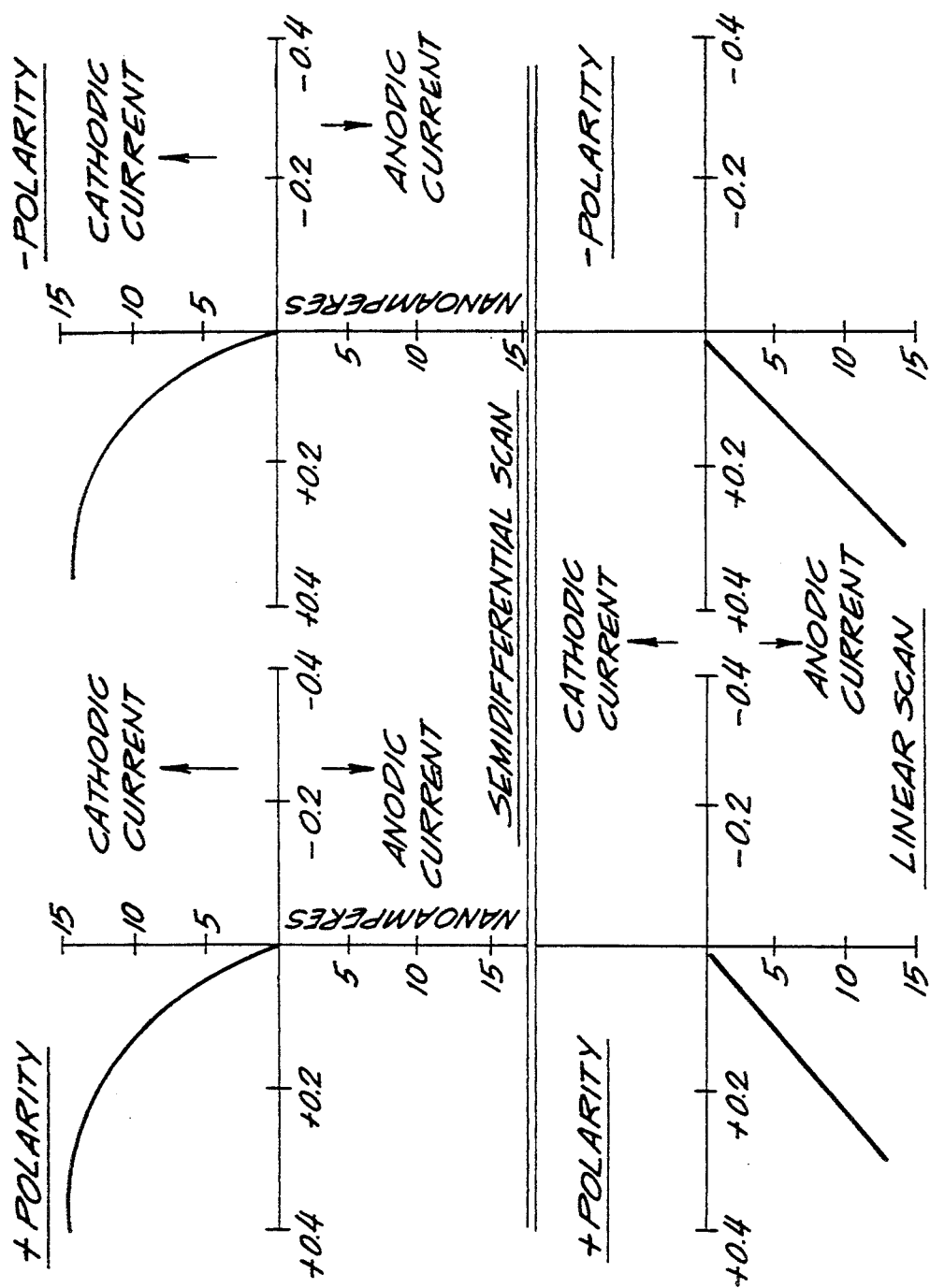
FIGS. 19(a) and 19(b) are diagrams illustrating that the difference between linear scanning techniques (b) and semiintegral and semidifferential processing (a) of current are not a function of polarity.
Figure 20A:
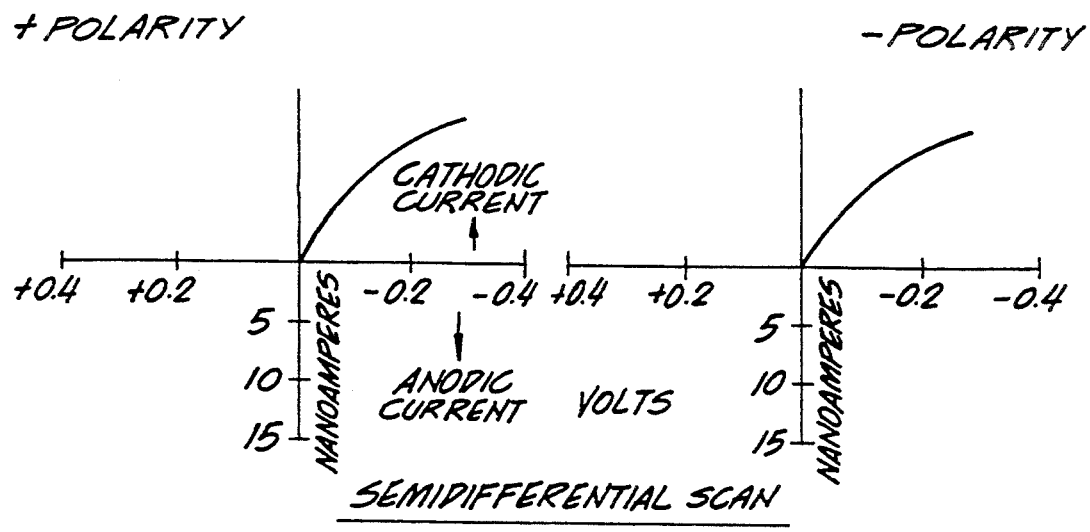
FIGS. 20(a) and 20(b) are diagrams illustrating that the differences between linear scanning techniques (b) and semiintegral and semidifferential processing (a) of current are not a function of the directionality of Eapp (applied potential).
Figure 20B:
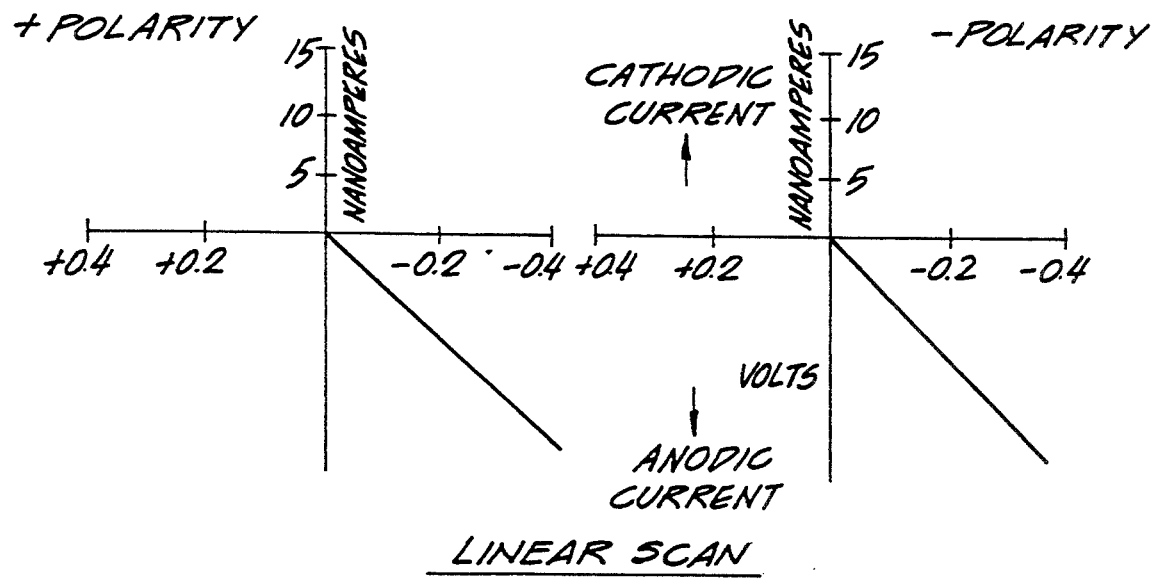
Figure 21:
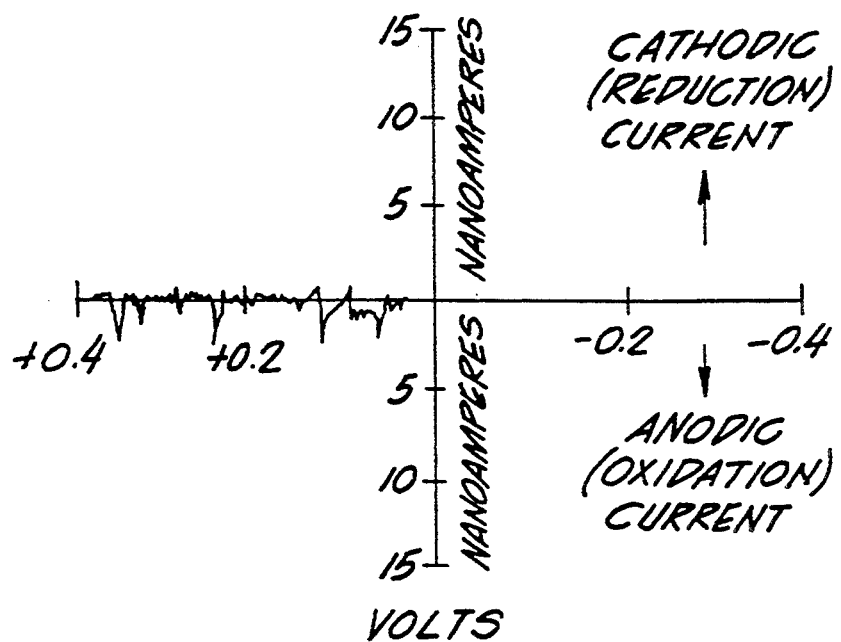
FIG. 21 is a diagram illustrating recording results from a semidifferential voltammogram processed with an anodic (oxidation) current, from the brain. The recording is unrecognizable.
Figure 22:
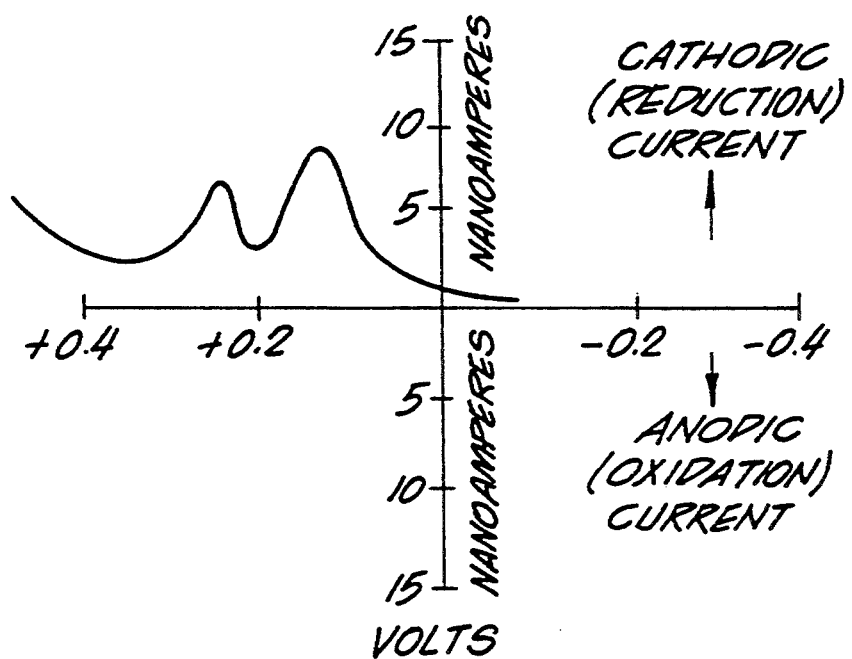
FIG. 22 is a diagram illustrating a recording from a semidifferential voltammogram processed with a cathodic (reduction) current according to the method of this invention.
Figure 23:
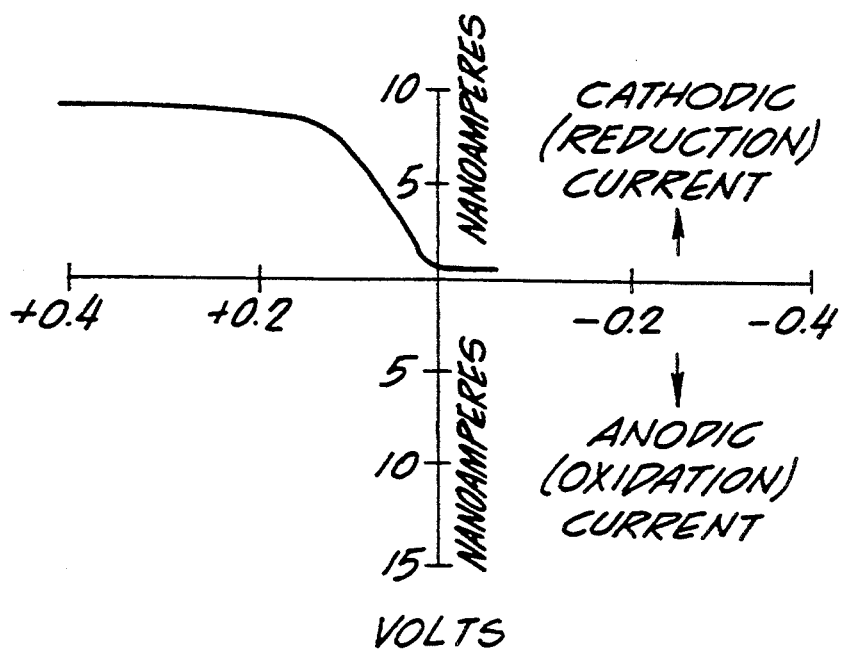
FIG. 23 is a diagram illustrating a recording from a semidifferential voltammogram processed with a cathodic (reduction) current with an electrode which had not been brain-treated; e.g., whose adsorption properties at the diffuse double layer of the electrode surface (the capacitance or barrier layer) had not overcome any possible column effects.
Figure 24:
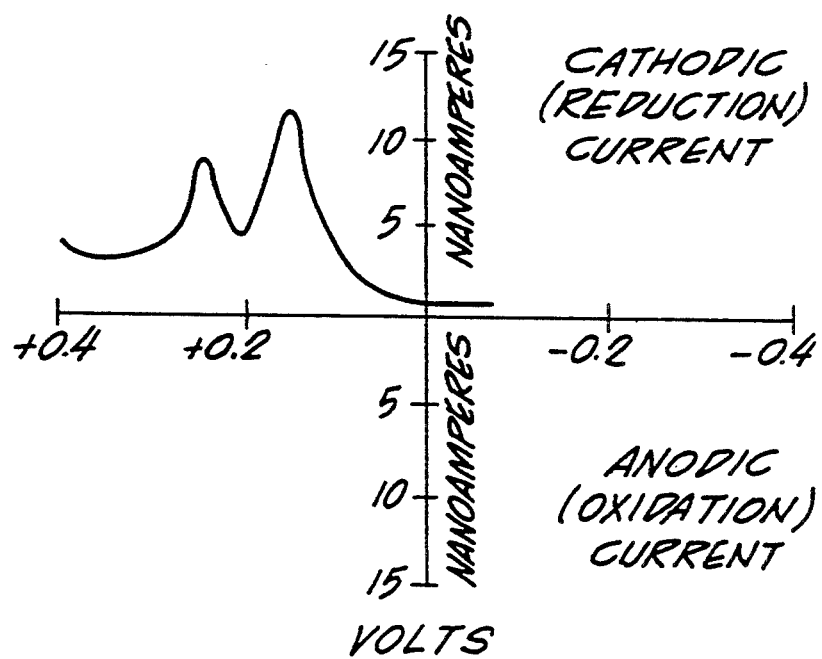
FIG. 24 is a diagram illustrating a recording from a semidifferential voltammogram, processed with a cathodic (reduction) current, with a brain fluid-adsorbed electrode treated with fatty acids to selectively detect cations or anions for medical diagnosis.
Figure 25:
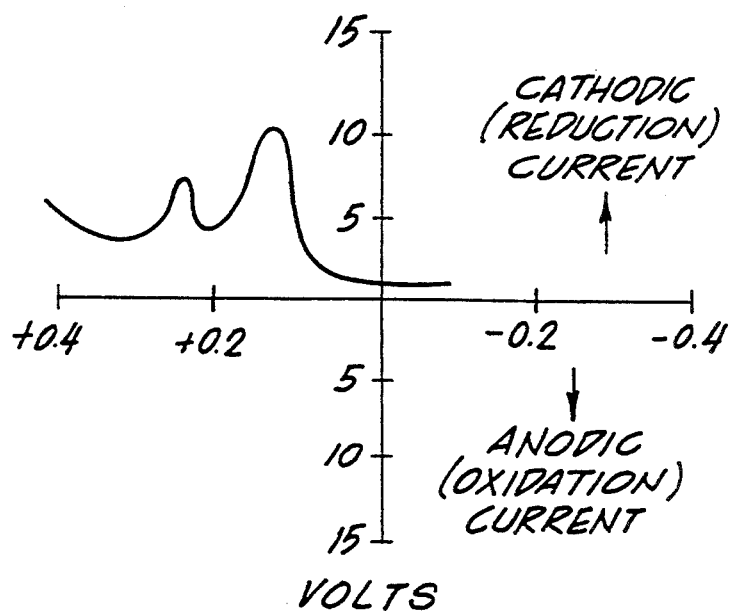
FIG. 25 is a diagram illustrating a recording from a semidifferential voltammogram, processed with a cathodic (reduction) current according to the method of this invention, with a brain fluid adsorbed electrode, treated with fatty acids, in vitro in phosphate buffer (0.01M PO4 buffer made with monobasic and dibasic phosphate) with dopamine and serotonin hydrochloride, said biogenic chemicals correlating to the same peaks in the brain, thus showing the detection of said biogenic chemicals as attainable for purposes of future discoveries in treatment.

The method of this invention requires a cathodic current production. This current production is not a simple function of a change in polarity, which would produce the same signal, as shown by FIG. 19; nor is it a simple function of the directionality of the applied potential, Eapp, as shown by FIG. 20. FIG. 16 is a graphical representation of the use of anodic current used with non-differentiated current. FIG. 17 is a graphical representation of the use of the method of this invention; cathodic current used with semidifferentiate current. The graph of FIG. 17 shows sharp peaks produced by chemical species, compared to the curve generated by non-differentiated anodic current of FIG. 16.

Figure 18:
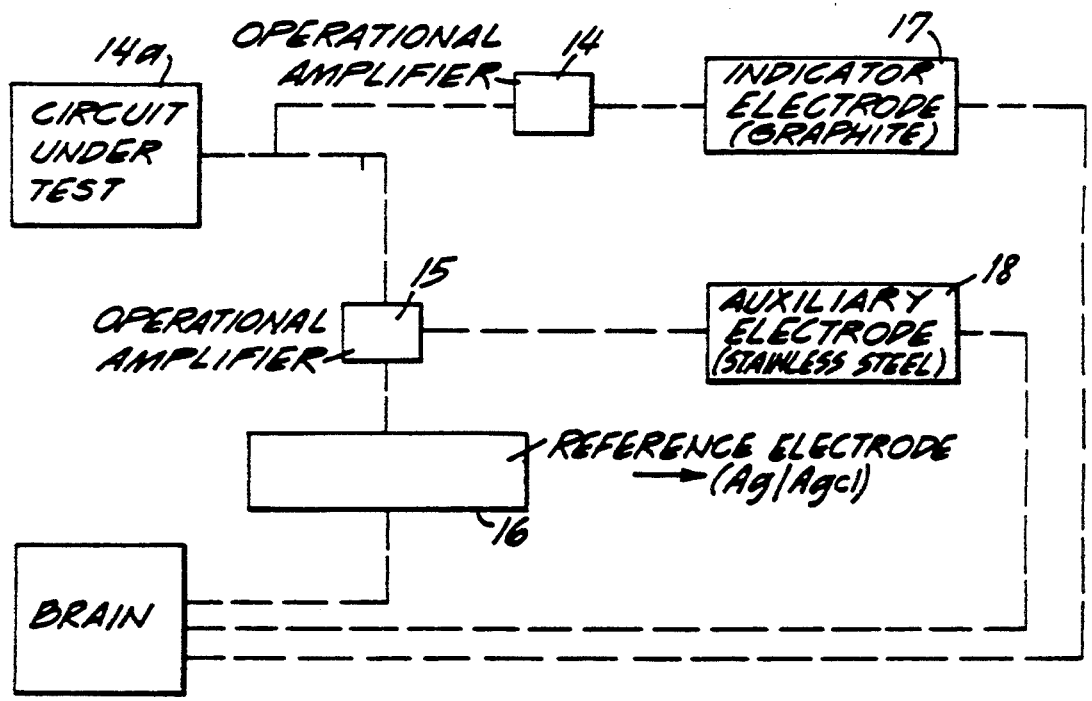
FIG. 18 is a schematic diagram of the three electrode system used in accordance with the method of this invention to generate such signals from living organisms and its relationship to the operational amplifier circuitry needed for semidifferential processing of current in addition to other types of electroanalysis.

FIG. 18 is a schematic diagram of a known three electrode system necessary to generate electrochemical signals from brain and other parts of living and non-living things. The figure is drawn in relationship to said operational amplifier circuitry needed for varying types of electrochemical procedures. FIGS. 21 through 25 are graphical representations of correct electrochemical signals vis-a-vis incorrect electrochemical signals; only the correct signals are useful as markers for diseased and healthy states and are thereby useful for diagnostic and therapeutic medical research.

Figure 26:
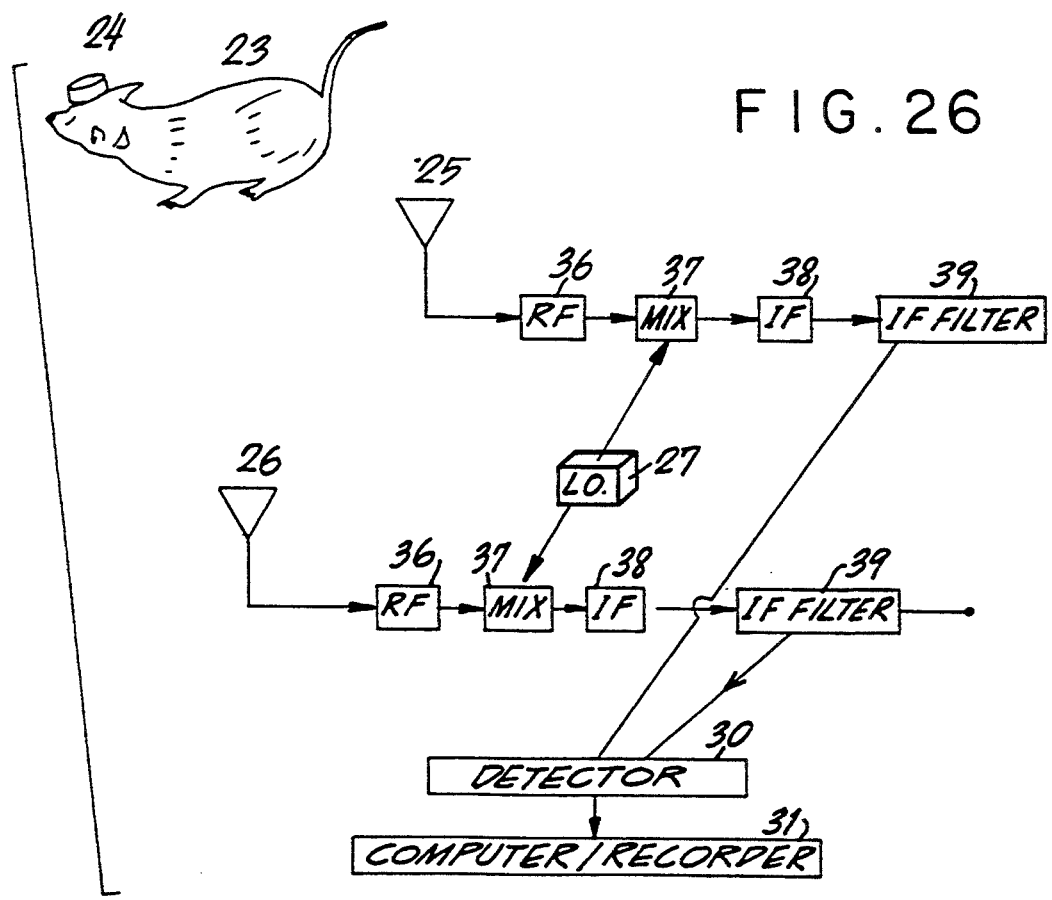
FIG. 26 is a schematic drawing illustrating the telemetric application to the electrochemical process of this invention, using a channel 8 or 9 television band in the transmitter to detect biogenic and other chemicals useful in biomedical diagnosis.

FIG. 26 shows the telemetric embodiment of the in vivo electrochemical semidifferential and linear detection of neurochemicals, biogenic amines and peptides both in the mobile and non-mobile, human and non-human organism, for purposes of medical diagnostics and preclinical and clinical pharmacotherapeutic discovery. Shown at, 23, is a pictorial view illustrating a rat, a commonly used laboratory animal, bred for the expressed purposes of biomedical research. The three electrode electrochemical circuit, FIG. 18, is implanted in the brain described in this invention. The electrode system is then cemented to the skull of the organism with acrylic and fitted with a snap on telemetric transmitter, 24, the principal elements of which comprise a Channel 8 or 9 TV Band, an oscillator, a silver oxide battery power supply, a contact switch assembly and a contactor for the three electrode snap on closure electrode system. Voltage is transmitted via electrolytes in the brain extracellular fluid, to a dual antenna network, 25–27, according to the invention of Dinsmore which allows interference-free reception of physiological signals through telemetry. A plurality of RFFM receiving channels are each associated with an antenna. Each is comprised of one or more RF amplification stages 36, a mixer stage 37 and one or more intermediate frequency stages 38, 39 along with an analog circuit. The common local oscillator, 27, provides uniformity in the intermediate frequency. A current measurer operational amplifier changes the output voltage of the telemetric receiver to current by an analog circuit 30, and the signal is displayed on a computer printer or strip chart recorder, 31. The detector, 30, is preferably a 3089 IC from National Semiconductor Corporation in accordance with the method of Dinsmore, in combination with the semidifferential circuit of Oldham, in addition to the novel circuitry of this invention described in FIG. 15.

Figure 27:
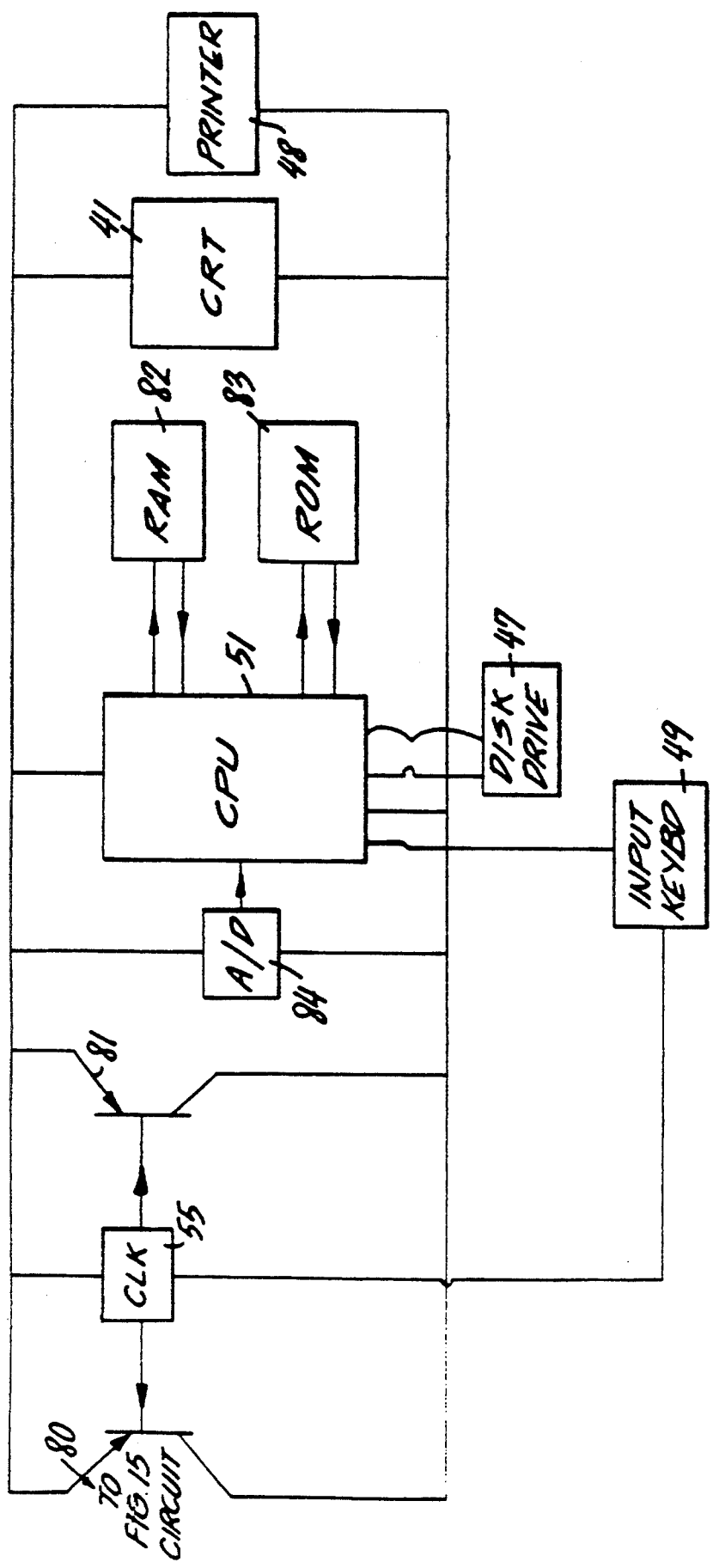
FIG. 27 is a schematic drawing illustrating a system for interfacing the detector with a computer.

The automation of the method of this invention to aid in the rapid detection of healthy and diseased states is described. A computer monitor, 41, a disk drive, 47, a printer, 48 and a computer keyboard, 49, are depicted in FIG. 27. Processor memory 82 and 83 are provided to move information from disk drive to memory. Memory disk drive 47 is provided as a means for bussing information. Chipboard 51 contains chips for the central processing unit, a fast 8-bit microprocessor, controlling analog to digital converter function, 84, printer 48 and disk drive 47. The "transistor-transistor logic", or "TTL", produces the outputs to the remote control pins of the circuitry depicted in FIG. 15. The output of organ 19 is connected to a detector (not shown) which contains all of the circuitry of FIG. 15. The TTL outputs can be controlled by an internal clock 55 such as the clock in an Apple IIe. The principal concept governing this automatic embodiment of the method of this invention is the application of the passage of a high voltage through a transistor in the computer TTL, 81, forming an on/off switch mechanism. The TTL logic is based on a switch which varies potential from 0 to 5 Volts logic. The detector logic comprising the unamplified circuit of FIG. 15 is TTL also, based on a 0–5 Volts switch off/on logic. In a practical embodiment, a strap cable can connect computer TTL switch 81 with detector TTL switch 80 through a terminal strip, with an interfacing device (not shown) which receives inputs and outputs from the TTL 80 and the TTL 81. In the present invention, this interfacing device has no electronic importance, but that does not by any means preclude additional electronic importance in the future, e.g. operational amplifiers, intended to amplify or dampen, are contained in this box which could amplify or dampen or otherwise attenuate or amplify signals from the brain and other living suborgans should the electrical interference from, say several computers, serve to dampen the signal. A strap cable from the TTL 80 connector, electrically connected to cell 14–19 of FIG. 15 comprises four or five single cables, designated to ground, scanning operation, cell and beginning and possibly ending applied potential in mv. TTL inputs and outputs on A/D converter 84 direct analog to digital converter TTL Logic in the interface (not shown) and switch 80. In addition, the attached programs e.g. shown in FIGS. 28(a) and 28(b) integrate the height and area under each analog signal which emanates from the brain and/or other suborgans, thus allowing for on-line analysis of neurotransmitter—and neurotransmitter—like substances in healthy and diseased states for the purposes of medical diagnosis.

FIGS. 29 and 30 set forth preferred embodiments for accomplishing specific functions of the circuit of this invention as shown schematically in FIG. 15. In FIG. 29(a), $Z_1$ and $Z_2$ are feed-in and feed-back impedances and, when the amplifier is equipped with high gain capacitance, the transfer function of the circuit can be delineated by $Z_1$ and $Z_2$. The point B where $Z_1$ and $Z_2$ are connected together and to the amplifier input is the "summing junction," which provides a ground because the signal voltage is infinitesimal. The current through $Z_1$ is equal to the current through $Z_2$. V, the potential drop across C is defined as:

$$V = -\frac{1}{C}\int idt = -\frac{1}{CR}\int V idt.$$

FIG. 30 shows a type of direct coupling amplifier based on a triode 301, i.e., an electronic valve with a wire mesh grid 304 and a cathode 302. The triode is the basis of the amplifier. When the third electrode (anode) 303 is held at a small negative potential relative to the cathode, electrons flowing through the valve are not attracted to the grid 304 but can still pass through it to the anode. Any change of the grid potential will produce a far greater change in the electrical field close to the cathode than will a similar alteration of anode potential. The direct coupling of more than one amplifier circuit allows the output of the first amplifier to be applied between the cathode and the grid of the next. The grid of the next stage should be held at a small negative potential with respect to its own cathode, to be a cathodic amplifier. A battery can provide a potential difference between the anode and the succeeding grid.

Figure 3A:
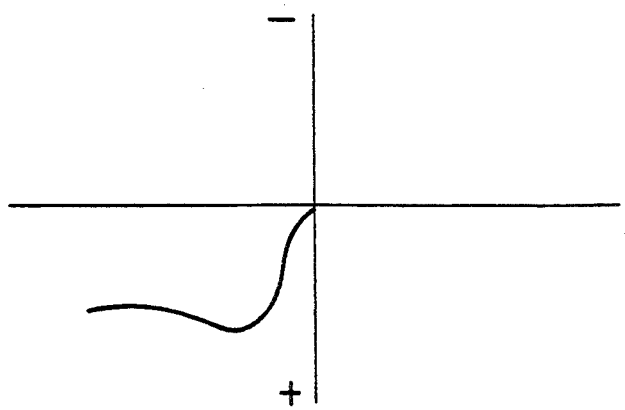
FIGS. 3A, 3B and 3C are representations of graphs showing signals which may be generated by linear and semidifferential scanning.
Figure 3B:
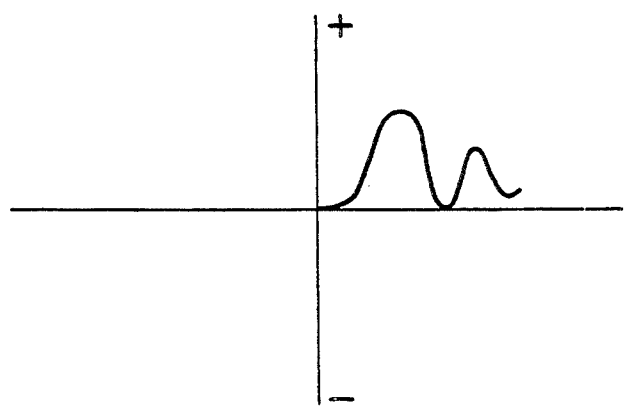
Figure 3C:
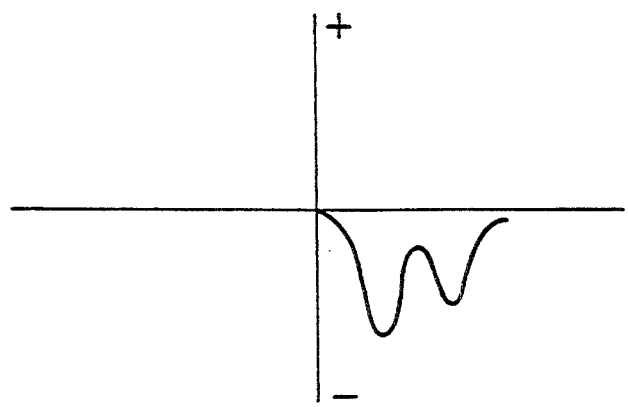

Therefore, one of the differences between the method of this invention and prior art methods can be seen by comparing a semiderivative voltammogram produced by using the method of this invention with graphs produced by prior art methods. In FIGS. 3A-3C, a "minus" notation denotes a reduction current and a "plus" notation denotes an oxidation current. FIG. 3A shows a graph obtained by a linear scan of biogenic chemicals. It is a typical curve representing an anodic current in conventional electrochemical form [Kissinger et al.]. In FIG. 3A, the peaks for biogenic amines, such as serotonin, are masked and undifferentiated from each other such as the dopamine peak. FIG. 3B is a semiderivative voltammogram which also presents an anodic current but is presented in non-conventional electrochemical form. [Lane, Hubbard and Blaha,. J. Electrochemistry, Vol. 95, (1979), p. 117.] In FIG. 3B, the dopamine and serotonin signals are contaminated by many other amines and many metabolites in addition to ascorbic acid and possible uric acid. FIG. 3B shows differentiated serotonin and dopamine peaks. FIG. 3C is a representation of a semiderivative voltammogram using nonconventional electrochemical notation, derived from using the method of this invention. It shows sharp, differentiated uncontaminated serotonin and dopamine peaks using a cathodic current and selective electrodes that are either brain treated or electrodes that have undergone the electrode conditioning process described herein, before implantation of the electrode in discrete brain regions. Unexpectedly, these and other chemicals heretofore undescribed can be reproducibly detected, such as in FIG. 17, by using a cathodic current according to the method of this invention.

Thus, the reproducibility and purity of signals generated by the process of this invention allow the automation of the cathodic current as demonstrated in FIGS. 27 and 28, as well as the telemetric application of the process of this invention to aid in the diagnosis of diseased states as shown in FIG. 26.

The process of this invention may also be used in humans as a neurochemical mapping device in order to show electrode placement in the human brain. By knowing the typical signal pattern produced in each part of the brain, a physician or researcher would be aware of the exact location of the electrode in a living patient without the necessity of dissecting the brain.

Figures 5A, 5B:
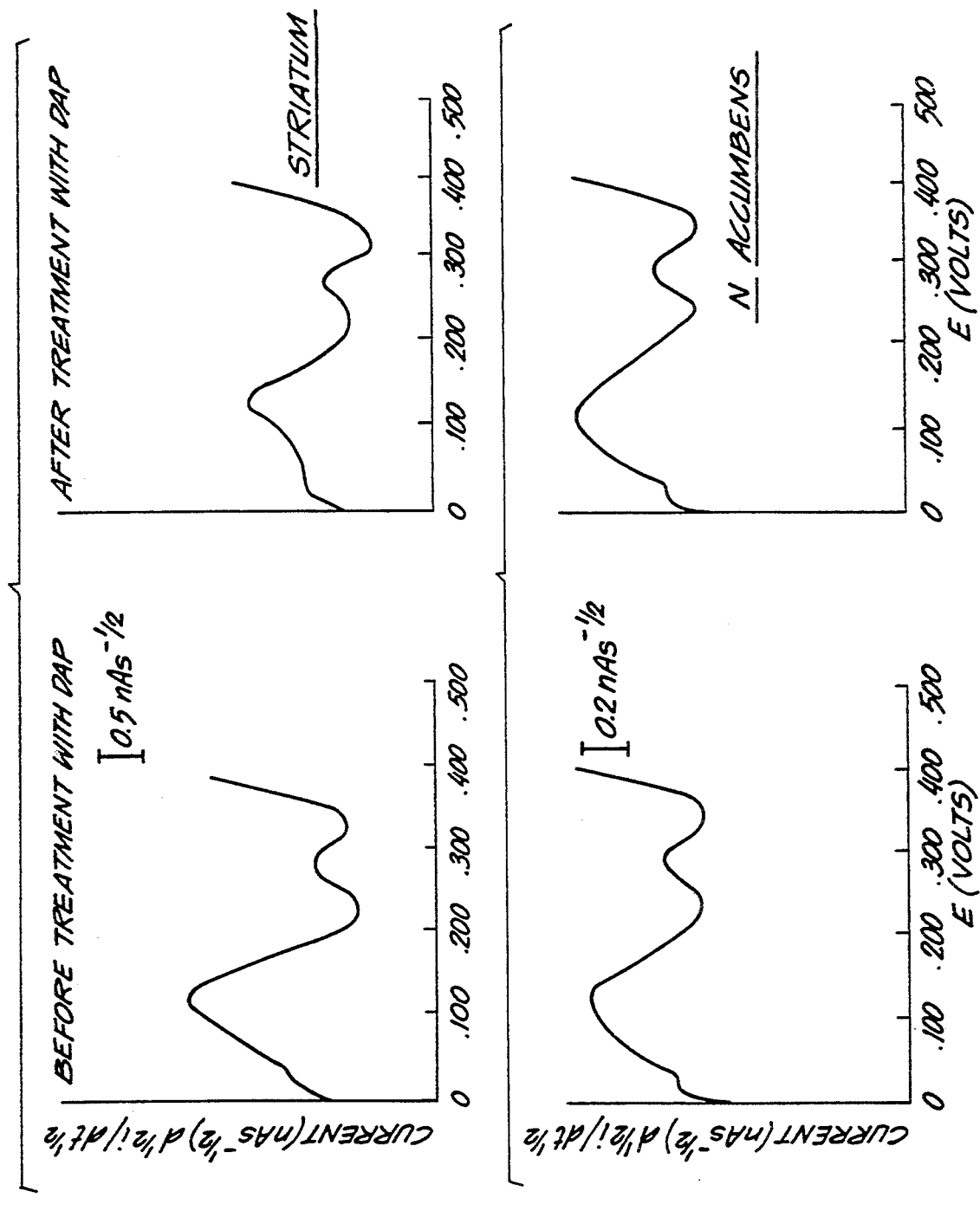
FIG. 5 is a representation of semiderivative voltammograms obtained from nucleus accumbens and striatum of the rat brain before and after treatment with DAP. These beginning neurochemical profiles from different brain regions can provide a means for neurochemical mapping for diagnosis as also exemplified in FIG. 6 below, so that the electrode placement can be ascertained by the signal profile displayed on a recorder, printer, or computer monitor.
Figure 6:
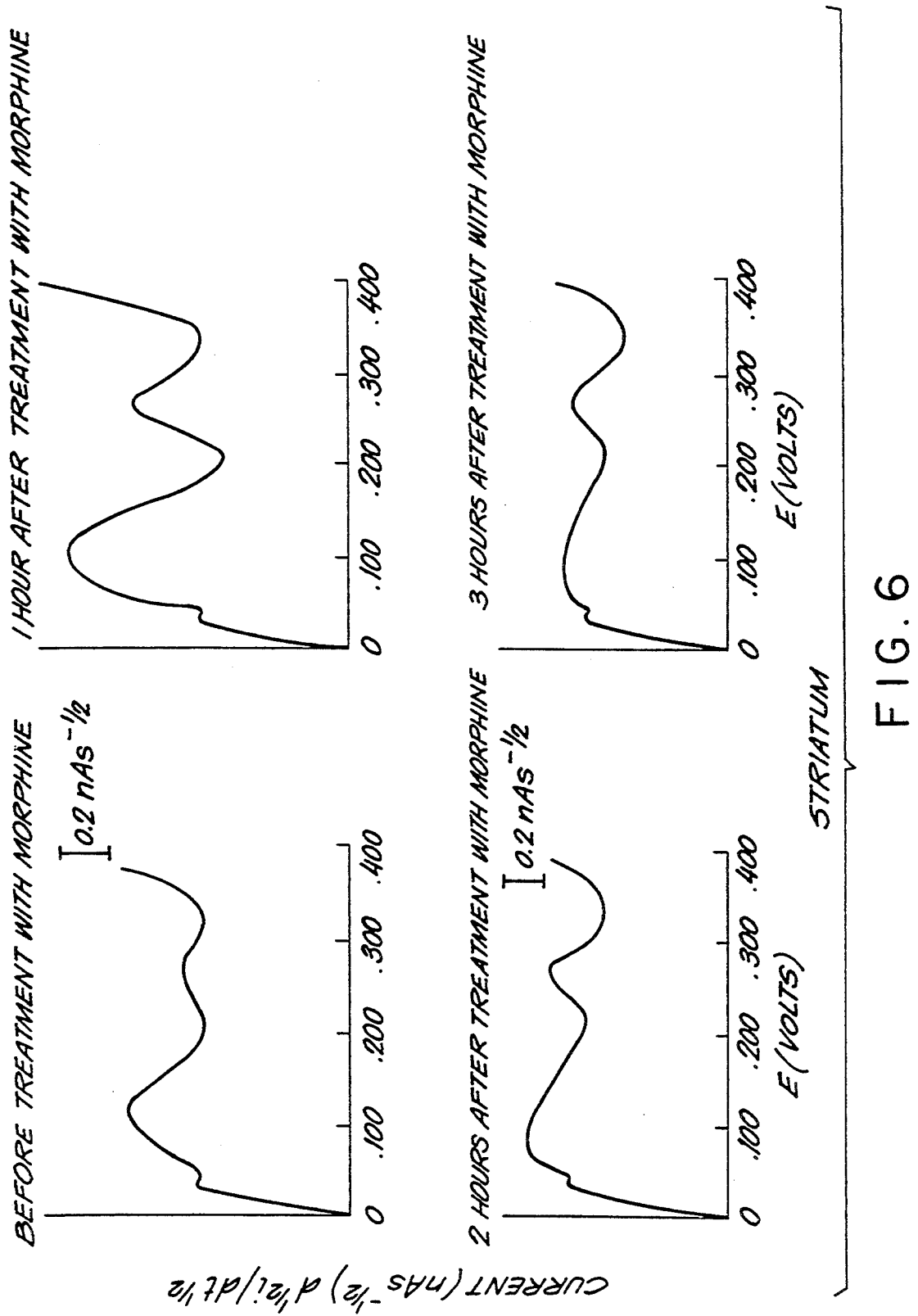
FIG. 6 is a representation of semiderivative voltammograms obtained prior to and 1, 2 and 3 hours after treatment with morphine, the results being directly related to underlying neurochemical addiction and pain processes.

The method of this invention can be used to measure biogenic chemicals in the organs of the body as well as in different parts of the brain, e.g. the striatum, tuberculum olfactorium, nucleus accumbens, median raphe, periaquaductal gray, hippocampus, locus coeruleus, the frontal cortex, amygdala, hypothalamus, thalamus, substantia nigra, globus pallidus and other areas. The methods of this invention can also be used to measure biogenic chemicals in such organs of the body as the heart, the retina, the gut, the cervix, kidney, liver, gall bladder, vagina and the like so as to diagnose, e.g., cervical cancer and the like. Subsequent neurochemical profiles are useful in diagnosis. For example, the method can also be used as a mapping device to determine electrode placement in the human, as shown in FIGS. 5 and 6.

Moreover, it can be used as a diagnostic tool to measure dynamic levels of biogenic chemicals and compare them to established normal dynamic values. The method of this invention can be used to measure levels of biogenic chemicals such as amines, amine metabolites, ascorbic acid, amino acids, particularly dopamine, homovanillic acid, tryptophan (a chemically irreversible substance), serotonin, enkephalins and enkephalinamides, neurotransmitters, putative neurotransmitters, and neuromodulators. It is believed that neuropeptides can also be measured using the method of this invention.

It is also believed that non-electroactive substances such as acetylcholine and electroactive substances that have small or low diffusion coefficients can be measured using the method of this invention. Non-electroactive substances and electroactive substances with small or low diffusion coefficients as well as electroactive substances having more than one electroactive moiety can be detected by immunoassay in association with or combination with the instant invention. An antigen is bound to an antibody and injected iontophoretically or by other means into brain or other organs in vivo and/or in vitro. Free and bound antigen differ in their electrochemical characteristics and the distinction can provide the detection of new substances. Free or unbound antigen can be more electroactive than bound antigen. U.S. Pat. No. 4,395,312, issued Jul. 16, 1983 to McCreery discusses means by which spectroelectrochemical means, associated with immunoassay means, are used to effect detection of some biochemical species in vitro. The instant invention can be used in combination with spectroelectrochemical means and/or immunoassay means and/or radioimmunoassay means.

These chemicals may be present at certain dynamic levels in normal persons without the administration of any stimuli. However, in persons having abnormal psychological characteristics, and, therefore, forms of mental illness, different dynamic levels of biogenic chemicals may be present. Thus, the in vivo electrochemical method of this invention may be used to diagnose mental illnesses, such as obesity, depression, manic depression, drug addiction, and others, such as neurochemical disorders in AIDS, e.g., AIDS related depression, etc., according to the dynamic levels of certain chemicals in the brain. The method of this invention can also be used for predicting the advent of neurological and other diseases such as diabetes, Alzheimer's, Parkinson's and Huntington's diseases based on the comparison between known normal levels and abnormal levels of particular substances, e.g. dopamine. The method can be used in combination with and to complement electrophysiological investigations and spectrophotofluorometric devices for studying calcium and other depolarizing agents in lymphocytes and fibroblasts as well as skin biopsies of patients with diseases, e.g. Alzheimer's and schizophrenia. It can also be used in studies of neuroimmunomodulation.

Moreover, certain biogenic chemicals measurable by the method of this invention are produced and/or altered in reaction to central or peripheral administration of chemical stimuli, such as drugs. These chemicals which may produce such reactions are psychopharmacological and neuropsychopharmacological agents such as neuroleptics, neuropeptides, amino acids, analgesics, gut and brain hormones, calcium blockers, addictive agents, antidepressants, antianxiety agents, anti-panic agents, amphetamines, endorphins, particularly beta and gamma-endorphins, enkephalins, enkephalinamides such as D-Met$^2$-Pro$^5$-enkephalinamide, cholecystokinin, dynorphin, marijuana, morphine, cocaine and other drugs and agents known to affect the human condition. Non-electroactive moieties and electroactive moieties which are slow to diffuse may be detected by attaching antigens to antibodies, the antigens having electroactive moieties, such as McCreery has done in vitro. However, in vitro applications are difficult to transfer to in vivo situations. For example, the central nervous system's effect on the release and reuptake of various neurotransmitters after peripherally-administered enkephalinamides have been detected, surprisingly, for the first time using the method of this invention.

The method of this invention can, therefore, be used for studying the mechanisms of action in the brain of particular agents. This would aid in the development of new psychotherapeutic agents by the study of structure-activity relationships of administered drugs. Analogs of the studied drugs could be evaluated for their effect on dynamic biogenic chemical levels in order to develop more effective therapeutic agents which have fewer and less severe side effects.

The following examples further illustrate certain embodiments of the method of this invention. Of course, they do not serve to limit the scope of this invention in any way. It should be noted that FIGS. 4, 5, 6, 9 and 10 illustrate representations of cathodic currents generated by using the method of this invention presented in the upright, nonconventional electrochemical notation. They should not be confused with conventional notation used throughout the descriptive example.

EXAMPLE 1

Teflon covered, stainless steel wire, 150–200 u diameter (Medwire, Mt. Vernon, N.Y.) was cut with a sterile #10 scalpel blade (Becton, Dickinson & Co., Rutherford, N.J.) into a 30 mm section. The cut was examined under a dissecting microscope (Nikon SMZ-1 with Nikon Transformer Illuminator XN) to determine the smoothness of the Teflon cut surface. Several blades should be used to achieve a flawless cut. The Teflon covering was then very gently pulled 500 u past the stainless steel. This exposed (2–5 mm) wire without Teflon in the middle of the electrode, while leaving the Teflon intact at the upper end of the wire. The exposed stainless steel was covered with spherical shaped acrylic dental cement. The electrode was then refined to a 10 mm length and a copper amphenol pin was soldered at the upper end, from which 2 mm of Teflon had been removed.

When the Teflon covering was gently pulled over the edge of the stainless steel, a cylindrical holder was formed. It was into this holder that the graphite stearate paste was packed. The graphite stearate paste was actually tapped into the Teflon holder by gentle prods, easing the grey claylike paste into the cylindrical holder from the surface of a clean glass plate, which was previously washed three times and separately with 95% ethanol and doubly distilled water. Slow, small tapping motions are used while coaxing the paste into the cylindrical holder. The paste should be homogeneously tapped into the cylindrical holder; the homogeneity of the paste should be examined under a dissecting microscope at 30×magnification. Excess graphite stearate paste was removed from around the tip of the electrode by gently applying the tip of the electrode, held at a 45 degree angle, to taut Teflon Tape (Fisher Scientific, Springfield, N.J.). The Teflon tape was previously washed three times and separately with 9% ethanol and doubly distilled water.

EXAMPLE 2

The fabrication of the graphite fatty acid paste was as follows: 1.24 ml Nujol (extra heavy), containing DL-a-tocopherol as a stabilizer, (Plough Inc., Memphis Tenn.) was admixed with 100 mg of stearic acid (99+%, Sigma, St. Louis, Mo.). This was done by stirring the extra heavy Nujol-stearic acid mixture manually with a glass stirring rod, while heating the Nujol mixture at incremental temperatures over a 10-min time period. The incremental temperatures should begin at 25° C. and end at 55° C. over the 10-min period. The Nujol-stearic acid was completely admixed before 1.5 g of Ultra Carbon (Ultra Superior Purity, Ultra Carbon, Bay City, Mich.) was added to the heated Nujol-stearic acid mixture. All stearic acid crystals should be melted before the mixture is removed from the heating device. The synthesized paste was allowed to cool. Then the paste was placed into a glass container. The glass container was rinsed with 100% ethanol and dried in nitrogen prior to placing the paste into it. The synthesized paste was aged and stored in the dark at room temperature. The vials were covered with parafilm. A great deal of care was taken not to allow dust and other extraneous particles near the paste mixture.

Combustion analysis and gas chromatographical analysis were performed on 5 mg synthetic graphite stearate paste mixtures to determine the accuracy of the content of graphite and stearic acid. The graphite content was determined by combustion analysis and the stearic acid content was determined by gas chromatographical analysis. The level of Nujol cart be calculated by the difference. These methods are important in the verification of paste composition. These methods have never been suggested for verification of any paste mixture heretofore.

EXAMPLE 3

The fabrication of the graphite fatty acid paste was as follows: 1.24 ml Nujol (extra heavy), containing DL-a-tocopherol as a stabilizer, (Plough Inc., Memphis Tenn.) was admixed with 100 mg of arachidic acid (Sigma, St. Louis, Mo.). This was done by stirring the extra heavy Nujol-arachidic acid mixture manually with a glass stirring rod, while heating the Nujol mixture at incremental temperatures over a 10-min time period. The incremental temperatures should begin at 25° C. and end at 55° C. over the 10-min period. The Nujol-arachidic acid was completely admixed before 1.5 g of Ultra-Carbon (Ultra Superior Purity, Ultra Carbon, Bay City, Mich.) was added to the heated Nujol-arachidic acid mixture. All arachidic acid crystals should be melted before the mixture is removed from the heating device. The synthesized paste was allowed to cool. Then the paste was placed into a glass container. The glass container was rinsed with 100% ethanol and dried in nitrogen prior to placing the paste into it. The synthesized paste was aged and stored in the dark at room temperature. The vials were covered with parafilm. A great deal of care was taken not to allow dust and other extraneous particles near the paste mixture.

Combustion analysis and gas chromatographical analysis were performed on 5 mg synthetic graphite arachidic paste mixtures to determine the accuracy of the content of graphite and arachidic acid. The graphite content was determined by combustion analysis and the arachidic acid content was determined by gas chromatographical analysis. The level of Nujol can be calculated by the difference. These methods are important in the verification of paste composition and have never been suggested for paste composition verification heretofore.

EXAMPLE 4

The fabrication of the graphite fatty acid paste was as follows: 1.00 ml Nujol (extra heavy), containing DL-a-tocopherol as a stabilizer, (Plough Inc., Memphis Tenn.) was admixed with 100 mg of arachidic acid (Sigma, St. Louis, Mo.). This was done by stirring the extra heavy Nujol-arachidic acid mixture manually with a glass stirring rod, while heating the Nujol mixture at incremental temperatures over a 10-min time period. The incremental temperatures began at 25° C. and ended at 55° C. over the 10-min period. The Nujol-arachidic acid was completely admixed before 1.5 g of Ultra Carbon (Ultra Superior Purity, Ultra Carbon, Bay City, Mich.) was added to the heated Nujol-arachidic acid mixture. All arachidic acid crystals were melted before the mixture was removed from the heating device. The synthesized paste was allowed to cool. Then the paste was placed into a glass container. The glass container was rinsed with 100% ethanol and dried in nitrogen prior to placing the paste into it. The synthesized paste was aged and stored in the dark at room temperature. The vials were covered with parafilm. A great deal of care was taken not to allow dust and other extraneous particles near the paste mixture.

Combustion analysis and gas chromatographical analysis was performed on approximately a 5 mg synthetic graphite arachidic paste mixture to determine the accuracy of the content of graphite and arachidic acid. The graphite content was determined by combustion analysis and the arachidic acid content was determined by gas chromatographical analysis. The level of Nujol was calculated by the difference. These methods were important in the verification of paste composition and have never been suggested for paste composition verification heretofore.

EXAMPLE 5

The fabrication of the graphite fatty acid paste is as follows: 1.24 ml Nujol (mineral oil), containing DL-a-tocopherol as a stabilizer, is admixed with 100 mg of arachidic acid (Sigma, St. Louis, Mo.). This is done by stirring the Nujol-arachidic acid mixture manually with a glass stirring rod, while heating the Nujol mixture at incremental temperatures over a 10-min time period. The incremental temperatures should begin at 25° C. and end at 55° C. over the 10-min period. The Nujol-arachidic acid is completely admixed before 1.5 g of Ultra Carbon (Ultra Superior Purity, Ultra Carbon, Bay City, Mich.) is added to the heated Nujol-arachidic acid mixture. All arachidic acid crystals should be melted before the mixture is removed from the heating device. The synthesized paste is allowed to cool. Then the paste was placed into a glass container. The glass container was rinsed with 100% ethanol and dried in nitrogen prior to placing the paste into it. The synthesized paste is aged and stored in the dark at room temperature. The vials are covered with parafilm. A great deal of care was taken not to allow dust and other extraneous particles near the paste mixture.

Combustion analysis and gas chromatographical analysis are performed on approximately a 5 mg synthetic graphite arachidic paste mixture to determine the accuracy of the content of graphite and arachidic acid. The graphite content is determined by combustion analysis and the arachidic acid content is determined by gas chromatographical analysis. The level of Nujol can be calculated by the difference. These methods are important in the verification of paste composition and have never been suggested for paste composition verification heretofore.

EXAMPLE 6

The fabrication of the graphite fatty acid paste is as follows: 1.24 ml Nujol (mineral oil), containing DL-a-tocopherol as a stabilizer, admixed with 100 mg of stearic acid (Sigma, St. Louis, Mo.). This is done by stirring the Nujol-stearic acid mixture manually with a glass stirring rod, while heating the Nujol mixture at incremental temperatures over a 10-min time period. The incremental temperatures should begin at 25° C. and end at 55° C. over the 10-min period. The Nujol-stearic acid is completely admixed before 1.5 g of Ultra Carbon (Ultra Superior Purity, Ultra Carbon, Bay City, Mich.) is added to the heated Nujol-stearic acid mixture. All stearic acid crystals should be melted before the mixture is removed from the heating device. The synthesized paste is allowed to cool. Then the paste is placed into a glass container. The glass container is rinsed with 100% ethanol and dried in nitrogen prior to placing the paste into it. The synthesized paste is aged and stored in the dark at room temperature. The vials are covered with parafilm. A great deal of care should be taken not to allow dust and other extraneous particles near the paste mixture.

Combustion analysis and gas chromatographical analysis are performed on 5 mg synthetic graphite stearic acid paste mixtures to determine the accuracy of the content of graphite and stearic acid. The graphite content is determined by combustion analysis and the stearic acid content is determined by gas chromatographical analysis. The level of Nujol can be calculated by the difference. These methods are important in the verification of paste composition and have never been suggested for paste composition verification heretofore.

EXAMPLE 7

The fabrication of the graphite fatty acid paste was as follows: 1.00 ml Nujol (extra heavy), containing DL-a-tocopherol as a stabilizer, (Plough Inc., Memphis Tenn.) was admixed with 50 mg of stearic acid (99+%, Sigma, St. Louis, Mo.) and 50 mg of arachidic acid (Sigma, St. Louis, Mo.). This was done by stirring the 1.00 cc of Nujol and 50 mg stearic acid and 50 mg arachidic acid manually with a glass stirring rod, while heating the Nujol mixture at incremental temperatures over a 10-min time period. The incremental temperatures began at 25° C. and ended at 55° C. over the 10-min period. The Nujol-stearic-arachidic acid was completely admixed before 1.5 g of Ultra Carbon (Ultra Superior Purity, Ultra Carbon, Bay City, Mich.) was added to the heated Nujol-stearic-arachidic acid mixture. All stearic-arachidic acid crystals were melted before the mixture was removed from the heating device. The synthesized paste was allowed to cool. Then the paste was placed into a glass container. The glass container was rinsed with 100% ethanol and dried in nitrogen prior to placing the paste into it. The synthesized paste was aged and stored in the dark at room temperature. The vials were covered with parafilm. A great deal of care was taken not to allow dust and other extraneous particles near the paste mixture.

Combustion analysis and gas chromatographical analysis were performed on approximately a 5 mg synthetic graphite stearic-arachidic paste mixture to determine the accuracy of the content of graphite, stearic and arachidic acid. The graphite content was determined by combustion analysis and the stearic acid and arachidic acid content were determined by gas chromatographical analysis. The level of Nujol was calculated by the difference. These methods were important in the verification of paste composition and have never been suggested for paste composition verification heretofore.

EXAMPLE 8

The fabrication of the graphite fatty acid paste was as follows: 0.10 ml Nujol (extra heavy), containing DL-a-tocopherol as a stabilizer, (Plough Inc., Memphis Tenn.) was admixed with 1 mg N-stearoyl-DL-dihydrosphingosine (10% of the Palmitine Analog) (Sigma, St. Louis, Mo.). This was done by stirring the 0.10 cc Nujol (extra heavy)-N-stearoyl-DL-dihydrosphingosine (stearoyl-sphingosine) mixture manually with a glass stirring rod, while heating the Nujol mixture at incremental temperatures over a 10-min time period. The incremental temperatures began at 25° C. and ended at 55° C. over the 10-min period. The Nujol-stearoyl-sphingosine mixture was completely admixed before 0.15 g of Ultra Carbon (Ultra Superior Purity, Ultra Carbon, Bay City, Mich.) was added to the heated Nujol-stearoyl-sphingosine mixture. All stearoyl-sphingosine crystals were melted before the mixture was removed from the heating device. The synthesized paste was allowed to cool. Then the paste was placed into a glass container. The glass container was rinsed with 100% ethanol and dried in nitrogen prior to placing the paste into it. The synthesized paste was aged and stored in the dark at room temperature. The vials were covered with parafilm. A great deal of care was taken not to allow dust and other extraneous particles near the paste mixture.

Combustion analysis and gas chromatographical analysis is performed on approximately a 5 mg synthetic graphite stearoyl-sphingosine paste mixture to determine the accuracy of the content of graphite, stearoyl and sphingosine. The graphite content is determined by combustion analysis and the stearoyl-sphingosine content is determined by gas chromatographical analysis. The level of Nujol is calculated by the difference. These methods are important in the verification of paste composition and have never been suggested for paste verification heretofore.

EXAMPLE 9

The fabrication of the graphite fatty acid paste was as follows: 0.10 ml Nujol (extra heavy), containing DL-a-tocopherol as a stabilizer, (Plough Inc., Memphis Tenn.) was admixed with 1 mg arachidic acid stearyl ester (Sigma, St. Louis, Mo.). This was done by stirring the 0.10 cc Nujol (extra heavy)-arachidic-stearyl ester mixture manually with a glass stirring rod, while heating the Nujol mixture at incremental temperatures over a 10-min time period. The incremental temperatures began at 25° C. and ended at 55° C. over the 10-min period. The Nujol-arachidic-stearyl compound was completely admixed before 0.15 g of Ultra Carbon (Ultra Superior Purity, Ultra Carbon, Bay City, Mich.) was added to the heated Nujol-stearic acid mixture. All of the arachidic-stearyl compound was melted before the mixture was removed from the heating device. The synthesized paste was allowed to cool. Then the paste was placed into a glass container. The glass container was rinsed with 100% ethanol and dried in nitrogen prior to placing the paste into it. The synthesized paste was aged and stored in the dark at room temperature. The vials were covered with parafilm. A great deal of care was taken not to allow dust and other extraneous particles near the paste mixture.

Combustion analysis and gas chromatographical analysis is performed on approximately a 5 mg synthetic graphite arachidic-stearyl paste mixture to determine the accuracy of the content of graphite and arachidic acid stearyl ester. The graphite content is determined by combustion analysis and the arachidic acid-stearyl ester content is determined by gas chromatographical analysis. The level of Nujol can be calculated by the difference. These methods are important in the verification of paste composition. These methods have never been suggested or used for paste composition verification heretofore.

EXAMPLE 10

The fabrication of the graphite fatty acid paste was as follows: 0.10 ml Nujol (extra heavy), containing DL-a-tocopherol as a stabilizer, (Plough Inc., Memphis Tenn.) was admixed with 1 mg stearic acid arachidyl ester (Sigma, St. Louis, Mo.). This was done by stirring the 0.10 cc Nujol (extra heavy or regular)-stearic acid-arachidyl ester mixture manually with a glass stirring rod, while heating the Nujol mixture at incremental temperatures over a 10-min time period. The incremental temperatures began at 25° C. and ended at 55° C. over the 10-min period. The Nujol-stearic acid-arachidyl ester was completely admixed before 0.15 g of Ultra Carbon (Ultra Superior Purity, Ultra Carbon, Bay City, Mich.) was added to the heated Nujol-stearic acid-arachidyl ester mixture. All stearic acid-arachidyl ester crystals was melted before the mixture is removed from the heating device. The synthesized paste was allowed to cool. Then the paste was placed into a glass container. The glass container was rinsed with 100% ethanol and dried in nitrogen prior to placing the paste into it. The synthesized paste was aged and stored in the dark at room temperature. The vials were covered with parafilm. A great deal of care was taken not to allow dust and other extraneous particles near the paste mixture.

Combustion analysis and gas chromatographical analysis are performed on approximately a 5 mg synthetic graphite stearic acid-arachidyl ester paste mixture to determine the accuracy of the content of graphite, and stearic acid-arachidyl ester. The graphite content was determined by combustion analysis and the stearic acid-arachidyl ester content are determined by gas chromatographical analysis. The level of Nujol is calculated by the difference. These methods are important in the verification of paste composition and have never been suggested for paste composition verification heretofore.

EXAMPLE 11

The fabrication of the graphite fatty acid paste was as follows: 0.05 ml Nujol (extra heavy), containing DL-a-tocopherol as a stabilizer, (Plough Inc., Memphis Tenn.) was admixed with 0.5 mg arachidic acid stearyl ester (Sigma, St. Louis, Mo.). This was done by stirring the 0.05 cc Nujol (extra heavy) arachidic-stearyl mixture manually with a glass stirring rod, while heating the Nujol mixture at incremental temperatures over a 10-min time period. The incremental temperatures began at 25° C. and ended at 55° C. over the 10-min period. The Nujol-arachidic-stearyl compound was completely admixed before 0.075 g of Ultra Carbon (Ultra Superior Purity, Ultra Carbon, Bay City, Mich.) was added to the heated Nujol-arachidic-stearyl mixture. All arachidic-stearyl compound was melted before the mixture was removed from the heating device. The synthesized paste was allowed to cool. Then the paste was placed into a glass container. The glass container was rinsed with 100% ethanol and dried in nitrogen prior to placing the paste into it. The synthesized paste was aged and stored in the dark at room temperature. The vials were covered with parafilm. A great deal of care was taken not to allow dust and other extraneous particles near the paste mixture.

Combustion analysis and gas chromatographical analysis are performed on approximately a 5 mg synthetic graphite arachidic-stearyl paste mixture to determine the accuracy of the content of graphite, the arachidic acid-stearyl ester. The graphite content is determined by combustion analysis and the arachidic acid-stearyl ester content is determined by gas chromatographical analysis. The level of Nujol is calculated by the difference. These methods are important in the verification of paste composition and have never been suggested for paste composition verification heretofore.

EXAMPLE 12

The fabrication of the graphite fatty acid paste was as follows: 0.05 ml Nujol (extra heavy), containing DL-a-tocopherol as a stabilizer, (Plough Inc., Memphis Tenn.) was admixed with 0.5 mg stearoyl cerebroside (bovine brain cerebroside) (Sigma, St. Louis, Mo.). This was done by stirring the 0.05 cc of Nujol (extra heavy or regular)-stearoyl cerebroside mixture manually with a glass stirring rod, while heating the Nujol mixture at incremental temperatures over a 10-min time period. The incremental temperatures began at 25° C. and ended at 55° C. over the 10-min period. The Nujol-stearoyl cerebroside compound was completely admixed before 0.075 g of Ultra Carbon (Ultra Superior Purity, Ultra Carbon, Bay City, Mich.) was added to the heated Nujol-stearoyl cerebroside mixture. All compound was melted before the mixture was removed from the heating device. The synthesized paste was allowed to cool. Then the paste was placed into a glass container. The glass container was rinsed with 100% ethanol and dried in nitrogen prior to placing the paste into it. The synthesized paste was aged and stored in the dark at room temperature. The vials are covered with parafilm. A great deal of care was taken not to allow dust and other extraneous particles near the paste mixture.

Combustion analysis and gas chromatographical analysis are performed on approximately a 5 mg synthetic graphite stearoyl cerebroside paste mixture to determine the accuracy of the content of graphite and stearoyl cerebroside. The graphite content is determined by combustion analysis and the stearoyl cerebroside content at least in part, is determined by gas chromatographical analysis. The level of Nujol is calculated by the difference. These methods are important in the verification of paste composition and have never even been suggested for verification of paste composition for in vivo studies, heretofore.

EXAMPLE 13

The phosphate buffer ($Na_2HPO_4$: $NaH_2PO_4$ ph 7.4) was made by mixing 0.02M $Na_2HPO_4$ (dibasic) with 0.02M $NaH_2PO_4$ (monobasic) in approximately a 4:1 ratio. Quite specifically, 405 ml dibasic was mixed with 95 mls monobasic for in vitro electrode conditioning for in vivo brain implants. Physiological saline (500 mls) was added. The final Molarity was 0.01M. The buffer was daerated with prepurified Nitrogen gas ($N_2$, extra dry grade, 5 psi, T. W. Smith Co., Bklyn, N.Y.). $N_2$ gas was perfused through the phosphate buffer and regulated with a Variable Area Flowmeter (Purgemaster, Fisher Sci., Fadem, N.J.). The Variable Area Flowmeter was calibrated at about 100 cc/min. Deaeration of the phosphate buffer with $N_2$ took place for one minute before each voltammetric scan began.

Dopamine (DA), ascorbic acid (AA), 3-4-dihydroxyphenylacetic acid (DOPAC), serotonin (5-HT), 5-hydroxyindoleacetic acid (5-HIAA) and uric acid (UA) were each pipetted into the phosphate buffer. The protocol consisted of separately testing a 1 uM amount of each compound in the phosphate buffer in which the graphite stearate electrode, Ag/AgCl reference electrode and auxiliary electrode were immersed. This was followed by pipetting cumulative 5 uM, 10 uM, 15 uM and 20 uM amounts of each compound separately into the same phosphate buffer, in 10 controlled studies. Each study began with an electrode test in 30 mls phosphate buffer with no added chemicals. The final volume of buffer with added chemicals was 30.12 mls. The electrodes were not exposed to brain extracellular fluid at anytime before or during the studies. In further experiments, homovanillic acid (HVA) (1–20 uM solutions) was pipetted into the phosphate buffer after the addition of DA, AA, DOPAC, 5-HT, 5-HIAA and UA.

In further experiments, final concentrations of 600 uM DA and ascorbate were measured in the 3-electrode phosphate buffer system in a 3-step, 200 uM aliquot protocol. Additionally, in preliminary experiments, final concentrations of 200uM dopamine with 20 uM ascorbate were measured. Also concentrations of 20 uM dopamine and 200 uM ascorbate were measured. The detection of uric acid with the graphite stearate electrode was also tested at high concentrations (up to 600 uM).

Detectable amounts of DA and 5-HT, which are less than 50 nM and 25 nM respectively, will be studied in the future.

EXAMPLE 14

The electroanalytical technique of linear potential sweep voltammetry (linear scan voltammetry) with a semidifferential output of current, which was modified according to the method of this invention with novel circuitry for the production of a cathodic (reduction) current, was used throughout the following examples.

The components of a DCV-5 detector made by Bioanalytical Systems (BAS-DCV5) were modified according to the method of this invention to produce cathodic circuitry for reproducible detection of biogenic characteristics in diseased and healthy states. The circuitry was plugged into an isolated ground. Also, the circuitry included a miniguard surge suppressor (from Jefferson Electric) having an input of 60 Hz and 95–130 volts. The output of the suppressor was 250 VA and 120 volts at 2.08 amps maximum. The modified DCV-5 was connected to a working electrode and a combined reference/auxiliary electrode. The teflon-coated working microelectrode (150–200 microns) was coated with a material consisting of graphite paste and nujol modified with stearate, which allows the measurement of changes in dopamine concentration and/or release and-/or reuptake without interference from ascorbic acid or the dopamine metabolite, 3,4-dihydroxyphenylacetic acid (DOPAC) and the detection of serotonin without interference from uric acid or the metabolite of serotonin, 5-hydroxyindoleacetic acid.

Adult, male, Sprague-Dawley rats were group housed and fed Purina rat food and water daily. Behavioral and biochemical studies were routinely carried out on these rats in the afternoons for better reproducibility. Surgical experiments were carried out in the mornings.

Prior to testing, a reproducible stable baseline measurement of the test rats' dopamine level was achieved in a period of 1.25 hours. The microelectrodes were first tested in vitro in phosphate buffer solution pH 7.4 (0.16M NaCl). Potentials were applied within a range of $-0.001$ or $-0.100$ to $+0.5$ v or higher or any combination thereof. The potentials were measured with respect to a reference Ag/AgCl electrode. Both the reference electrode and a platinum auxiliary electrode were placed in contact with the cortex of the brain. A stainless steel auxiliary electrode may also be used. The working electrode was stereotaxically implanted, using a David Kopf stereotoxic device, in the tuberculum olfactorium, according to the atlas of Pellegrino and Cushman, 1967 (coordinates: 2.6 mm anterior to Bregma, 2.5 mm lateral to midline and 9.5 mm below the dura mater, or skull surface).

On each experimental day, the animals were injected intraperitoneally with D-Ala$^2$-D-Pro$^5$-enkephalinamide monoacetate (DAP) dissolved in distilled water (5 mg/kg/ml), along with other animals injected with appropriate vehicle or saline control injections. Semiderivative voltammograms from rats anesthetized with chloral hydrate (450 mg/kg) were recorded every ten minutes for up to two hours at scan rate of 10 mv sec$^{-1}$ and a sensitivity of 0.2 nA sec$^{-1}$cm$^{-1}$.

Figure 4:
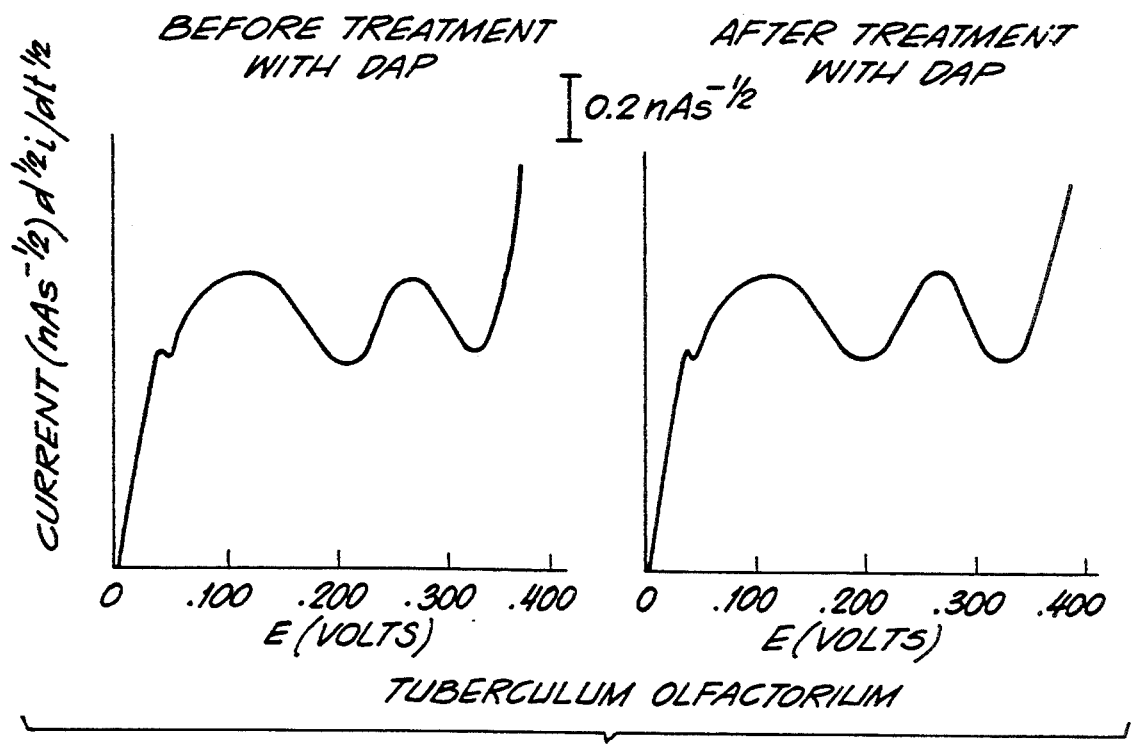
FIG. 4 is a representation of semiderivative voltammograms obtained from the tuberculum olfactorium of the rat brain before and after systemic treatment with $D-Ala^2-D-Pro^5$-enkephalinamide monoacetate (DAP), a compound similar to an endogenous opiate.

Changes in the dopamine signal in the tuberculum olfactorium after injection of DAP enkephalinamide were measured by comparing the mean of the pre-injection values with both the mean and the maximum of the post-injection values effects of the administration of the DAP enkephalinamide, in terms of basal dopamine release, is shown in FIG. 4, which shows two semiderivative voltammograms, one pre-injection and one post-injection. The dopamine signal (left-hand peak) is clearly unchanged from pre- to post-injection. The serotonin signal (right-hand peak) is, however, measurably higher after the injection.

It was observed that DAP did not inhibit the rats' locomotor activity. This observation is consistent with conventional theory which places control of locomotor activity in this part of the brain. It shows that dopamine levels in the tuberculum olfactorium are not affected by doses of DAP enkephalinamide. That locomotor activity was not affected is consistent with the placement of locomotor control in the tuberculum olfactorium because behaviorally DAP does not affect locomotor activity.

EXAMPLE 15

Rats were prepared for testing as in Example 14. The rats were injected with d-amphetamine sulfate (2.5 mg/kg) dissolved in saline, or DAP (5 mg/kg) followed in one-half hour by d-amphetamine sulfate. The amphetamine induced stereotypy in the treated rats, i.e. sniffing, head movement, rearing, licking, chewing, grooming, forepaw pacing and locomotor activity were observed. D-Ala$^2$-D-Pro$^5$enkephalinamide monoacetate was administered intraperitoneally. Changes in central nervous system dopamine concentrations in rat striatum and rat nucleus accumbens (coordinates adjusted to 4.0 and 7.5 mm below dura mater respectively), after administering the enkephalinamide were measured by comparing the mean of the pre-injection values with both the mean and the maximum of post-injection values. FIG. 5 shows semiderivative voltammograms from rat striatum (FIG. 5A) and rat nucleus accumbens (FIG. 5B). The semiderivative voltammograms show a significantly decreased dopamine signal from the striatum and no change in the dopamine signal from the nucleus accumbens. It was observed that the DAP inhibited head-bobbing, sniffing and frequency of rearing. It did not significantly inhibit the amphetamine-induced effect on locomotor activity. This is consistent with behavioral theory that associates stereotyped behaviors with nigrostriatal dopamine activation and locomotor activity with mesolimbic areas of the brain such as nucleus accumbens.

EXAMPLE 16

Rats were prepared for intraperitoneal administration of drug as in Example 14. D-morphine sulfate in distilled water solution was injected intraperitoneally (about 5 mg/kg rat weight) one hour after reproducible basal dopamine and serotonin signals were recorded from rat anterior striatum. The effect of morphine on striatal dopamine and serotonin signals was studied for a period of three hours. Alterations in the dopamine and serotonin signals, after morphine was injected, were measured by comparing the mean of pre-morphine injection values with both the mean and the maximum of post-morphine injection values. FIG. 6 shows the resultant semiderivative voltammograms taken 1, 2 and 3 hours after administration of morphine and shows changes in release and/or reuptake of brain chemicals in response to the drug. The results can be directly related to brain somatosensory systems involving tolerance to pain, addiction mechanisms and mechanisms of brain reward.

EXAMPLE 17

The method of this invention was used to diagnose diabetes mellitus as follows: male Sprague-Dawley rats were made diabetic with a single intraperitoneal injection of streptozotocin, 60 mg/kg. The diabetic state was assessed by positive glucose concentrations via urine analysis and by measurement of unfasting plasma glucose with the glucose oxidase 2 method (Beckman Glucose Analyzer). Blood was taken from the animals in capillary tubes via the intraocular method. Plasma glucose levels were in excess of 300 mg/100 mL. Neurotransmitters from these animals were studied along with age-matched controls at 3-day-and-a-month intervals following the induction of diabetes by measuring rate of release and reuptake using the circuit set forth in FIG. 15. The method of this invention was used to measure percent change from endogenously released dopamine and serotonin signals in a non-diabetic rat. The results of these measurements are diagrammed in FIG. 7. The method of this invention can therefore be applied to diagnose diseased states. The results show that serotonin is particularly vulnerable to the diabetic state and may indeed cause endogenous depression.

EXAMPLE 18

The method of Example 17 was used to study the dopamine signals from the brains of rats partially depleted of oxygen such as may be observed in brain injuries. This condition is known as "hypoxic hypoxia".

The left femoral artery of male Wistar rats (260–360 g) was cannulated for measurements of arterial partial pressures of oxygen ($PaO_2$) and carbon dioxide ($PaCO_2$) to determine the degree of hypoxia produced by a 15% $O_2$ inspiratory gas mixture. Bloods were drawn into 150 uL sodium heparin capillary tubes. Blood gases were measured by the ABL 30 Blood Gas Analyzer (Radiometer Amer. Inc., Westlake, Ohio). Gases were administered at a flow rate of six cubic feet per hour via a glove apparatus fitted over the animals' nose and mouth. Compressed air was administered to the animal. After a reproducible and stable baseline of extracellular dopamine and serotonin was evident, the animal was treated with 15% $O_2$ (See FIG. 8). The 15% $O_2$ was followed by compressed air treatment and repeated. The first recording in each treatment group was taken two minutes after the respective treatment was begun.

The administration of 15% $O_2$ treatment produced a significant increase on rat striatal extracellular dopamine, whereas administration of 20% $O_2$ returned the dopamine signal to control values. A second 15% $O_2$ treatment caused an irreversible increase in rat striatal extracellular dopamine. Data from femoral artery cannulations showed that $PaO_2$ values decreased as expected during the administration of 15% $O_2$ and returned to normoxic levels during the administration of each 20% $O_2$ treatment. Administration of 15% $O_2$ produced no significant effects on rat striatal extracellular serotonin.

EXAMPLE 19

The method of Example 17 was used to study pain or "analgetic" mechanisms. These mechanisms reflect cerebral blood flow related abnormalities related to somatosensory function and mechanisms of brain reward and drug addiction. These studies of brain analgetic mechanisms, use the opioid peptide, dynorphin. Dynorphin is a non-addicting opioid. FIG. 9a shows a typical voltammogram, of dopamine and serotonin release from rat striatum. Dopamine peaks at +130–+150 mv and serotonin peaks at +270–+290 mv when stearate is added to the graphite in vivo microelectrode. The effect of dynorphin administration on rat striatal dopamine and serotonin release is shown in FIG. 9b. Dopamine release decreased significantly, (30% below control value) and serotonin release increased significantly (40% above control values). The opposing effects of dynorphin occurred over a three-hour period after the administration of dynorphin. These results show that dynorphin does interact with analgetic brain mechanisms.

EXAMPLE 20

The effect of cocaine on dopamine release from striata of male, Sprague-Dawley rats was studied using the method of Example 17. The rats were injected with 20 mg/kg of cocaine subcutaneously. Chloral hydrate anesthetized rats underwent stereotaxic surgery for positioning in the anterior striatum of a teflon-coated working graphite electrode modified by stearate. A Ag/AgCl reference electrode and a stainless steel auxiliary electrode were placed in contact with the rat cortex. Semiderivative voltammograms were recorded every ten minutes. Potentials were applied between −200 and 500 mv, at a scan rate of 10 mv/sec. The results of these scans are illustrated in FIG. 10a as the percentage of basal dopamine release over a period of time, i.e. a decreased dopamine release was observed, emphasizing the control of dopaminergic function across membranes in brain reward and addiction processes.

A rat died of respiratory arrest after being administered a cocaine dose and was subsequently measured for dopamine release. The results of this measurement were compared to a similar measurement in a rat which had not received cocaine. These measurements are set forth in FIGS. 10(b) showing that cocaine has a direct effect on the membrane.

EXAMPLE 21

(Comparative Example)

The terming of this example as a comparative example is not an admission that it is prior art. The in vitro detection of dopamine and serotonin is measured by the semidifferential (semiderivative) voltammetry technique of Example 13, employing the phosphate buffer of Example 14, at a pH of 7.4, and or stearic acid-(stearate) working electrode. The stearic acid electrode is packed with 1 mg of a mixture made from 1.5 gms carbon (graphite), 1.00 cc Nujol (extra heavy) and 100 mg stearic acid. Electrodes are fabricated as in Example 1. Electrodes are then conditioned.

Conditioning includes exposing the electrode to a phosphate buffer solution including DA, DOPAC, AA, 5-HT, 5-HIAA and UA in 1-20 uM concentrations in a 1,5,10,15,20 uM five aliquot step protocol and applying −200 to +500 mV potential at a sensitivity of 2 nA/V. The potential was applied by a procedure similar to that of Example 14. In the first exposure, the electrode was exposed to DA DOPAC, AA, 5-HT, 5-HIAA and UA in a 1 uM concentration. The exposures were then repeated at the higher concentrations mentioned above to achieve five exposures. The five exposures were conducted in a 24 hour period.

Figure 45:
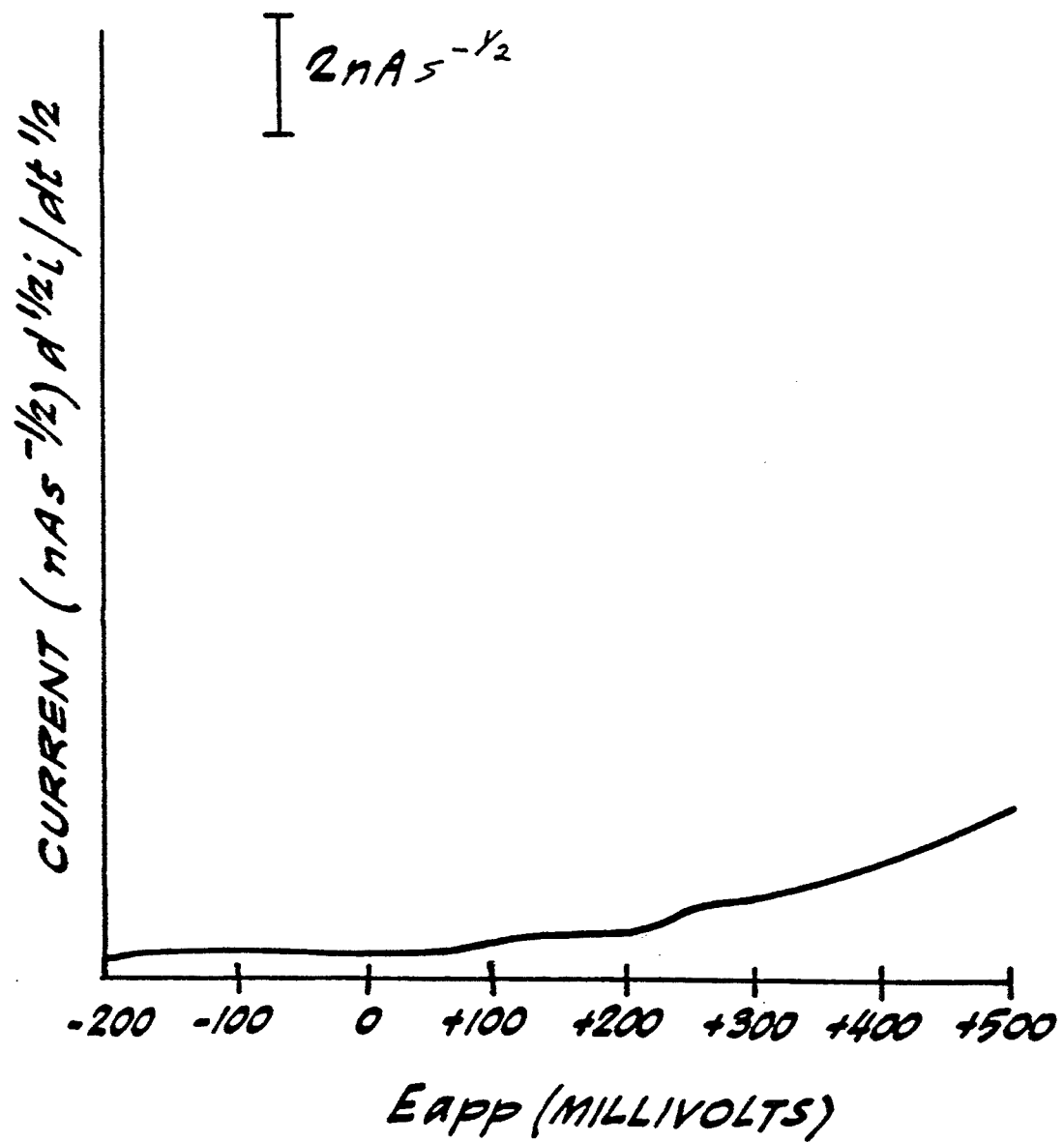
FIG. 45 is a semidifferential (semiderivative) voltammogram showing the in vitro detection of dopamine and serotonin (20 uM) in $PO_4$ (phosphate) Buffer containing DA (dopamine), 5-HT (serotonin), DOPAC (3,4-dihydroxyphenylacetic acid), 5-HIAA (5-hydroxyindoleacetic acid), AA (ascorbic acid), UA (uric acid) and HVA (homovanillic acid), at a pH of 7.4 with a stearic acid electrode made from a mixture of 1.5 g carbon (graphite), 1.00 cc extra heavy Nujol, and 100 mg stearic acid.

FIG. 45 shows a semiderivative (semidifferential) voltammogram showing the in vitro detection of dopamine (20 uM) and serotonin (20 uM) in phosphate buffer, at a pH of 7.4 with the above-described stearic acid electrode.

EXAMPLE 22

The steps of Example 21 were repeated. However, the electrode was packed with 1.5 gms graphite, 1.24 cc Nujol (extra heavy), and 100 mg arachidic acid.

Figure 46:
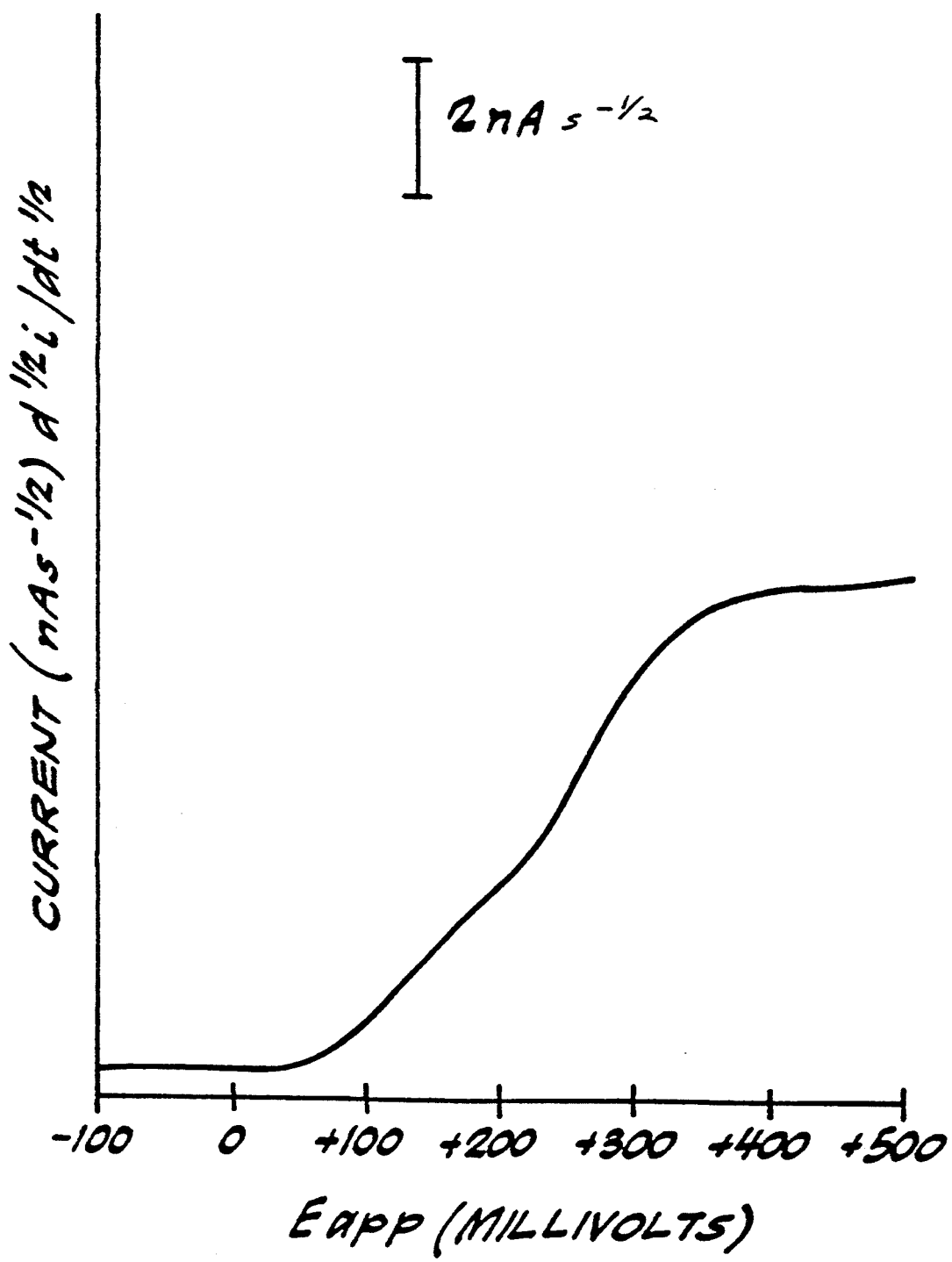
FIG. 46 is a semidifferential (semiderivative) voltammogram showing the in vitro detection of dopamine and serotonin (20 uM) in $PO_4$ buffer containing DA, 5-HT, DOPAC, 5-HIAA, AA, UA and HVA, pH 7.4 with an arachidic acid electrode made from a mixture of 1.5 g carbon (graphite), 1.24 cc extra heavy Nujol and 100 mg. arachidic acid.

FIG. 46 shows a semidifferential (semiderivative) voltammogram showing the in vitro detection of dopamine (20 uM) and serotonin (20 uM) in phosphate buffer at a pH of 7.4 with the above-described arachidic acid electrode.

A comparison of FIGS. 45 and 46 shows the arachidic acid electrode has greater sensitivity than the stearic acid electrode

EXAMPLE 23

The steps of Example 21 were repeated. However, the electrode was packed with 1 mg of paste made from a mixture of 0.075 gms graphite, 0.05 cc Nujol (extra heavy), and 0.5 mg stearoyl cerebroside.

Figure 47:
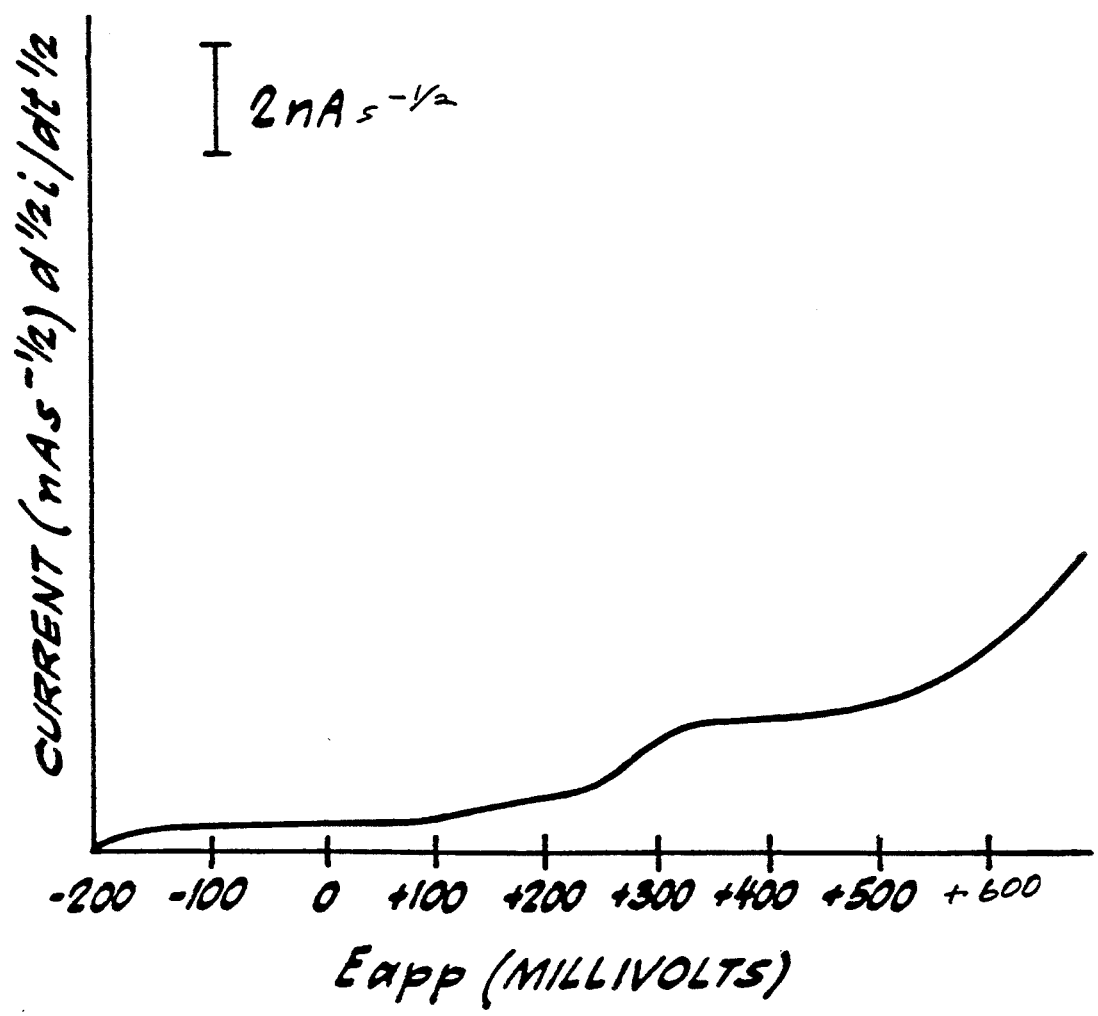
FIG. 47 is a semidifferential (semiderivative) voltammogram showing the in vitro detection of dopamine and serotonin (5 uM) in $PO_4$ Buffer containing DA and 5-HT, pH 7.4 with a stearoyl cerebroside electrode made from a mixture of 0.075 g carbon (graphite), 0.05 cc extra heavy Nujol and 0.5 mg stearoyl cerebroside.

FIG. 47 shows a semidifferential (semiderivative) voltammogram showing the in vitro detection of dopamine (5 uM) and serotonin (5 uM) in a PO4 buffer containing dopamine and serotonin with the above-described stearoyl cerebroside electrode.

A comparison of FIGS. 45 and 47 shows that the stearoyl cerebroside is more sensitive than the stearate (stearic acid) electrode for detecting dopamine and serotonin. The stearoyl cerebroside electrode was employed to detect dopamine and serotonin at one-fourth the concentration employed with the stearate electrode. However, the sensitivity of the stearoyl cerebroside electrode for serotonin is about fifteen to twenty fold that of the stearate electrode. The sensitivity of the stearoyl cerebroside electrode for dopamine is about three to six times that of the stearate electrode. Thus, in spite of the lower concentrations, FIG. 47 shows that the stearoyl cerebroside electrode results in significant peaks for serotonin and dopamine.

Also, on other days, this stearoyl cerebroside electrode was employed for detecting dopamine (DA) and serotonin (5-HT) in a PO4 buffer containing the chemicals DA, 5-HT, DOPAC, 5-HIAA, AA, UA and HVA at a pH of 7.4. 1, 5, 10, 15 and 20 uM concentrations of each chemical were employed in five respective tests. All the chemical are at the same concentration in a given test.

EXAMPLE 24

(Comparative Example)

Figure 48:
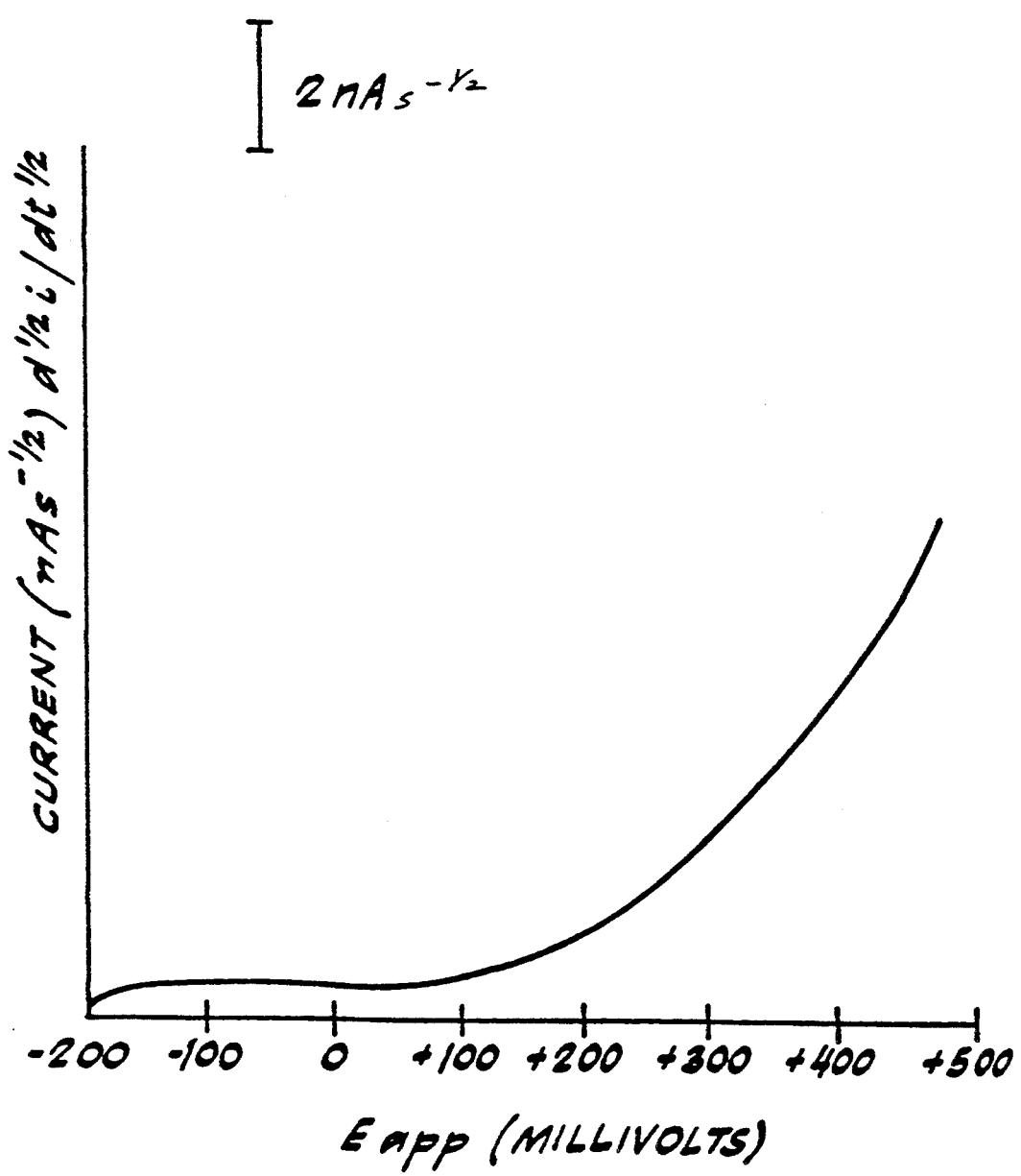
FIG. 48 is a semidifferential (semiderivative) voltammogram showing the in vitro detection of dopamine and serotonin (20 uM) in $PO_4$ buffer containing DA, 5-HT, DOPAC, 5-HIAA, AA, UA and HVA, pH 7.4 with a stearic acid electrode made from a mixture of 1.5 g carbon (graphite), 1.00 cc extra heavy Nujol and 100 mg stearic acid, with electrode conditioning taking place over a period of nine months. The typical period is 1 to 2 weeks.

The stearic acid electrode of Example 21 was reconditioned by repeating the conditioning steps of Example 21 at six and nine months after Example 21 was conducted. Then the electrode was employed for in vitro detection of dopamine (20 uM) and serotonin (20 uM) in phosphate buffer, at a pH of 7.4 by the steps described in Example 21. FIG. 48 shows a semiderivative (semidifferential) voltammogram of this invitro detection of dopamine (20 uM) and serotonin (20 uM). The terming of this example as a comparative example is not an admission that is is prior art.

EXAMPLE 25

Figure 49:
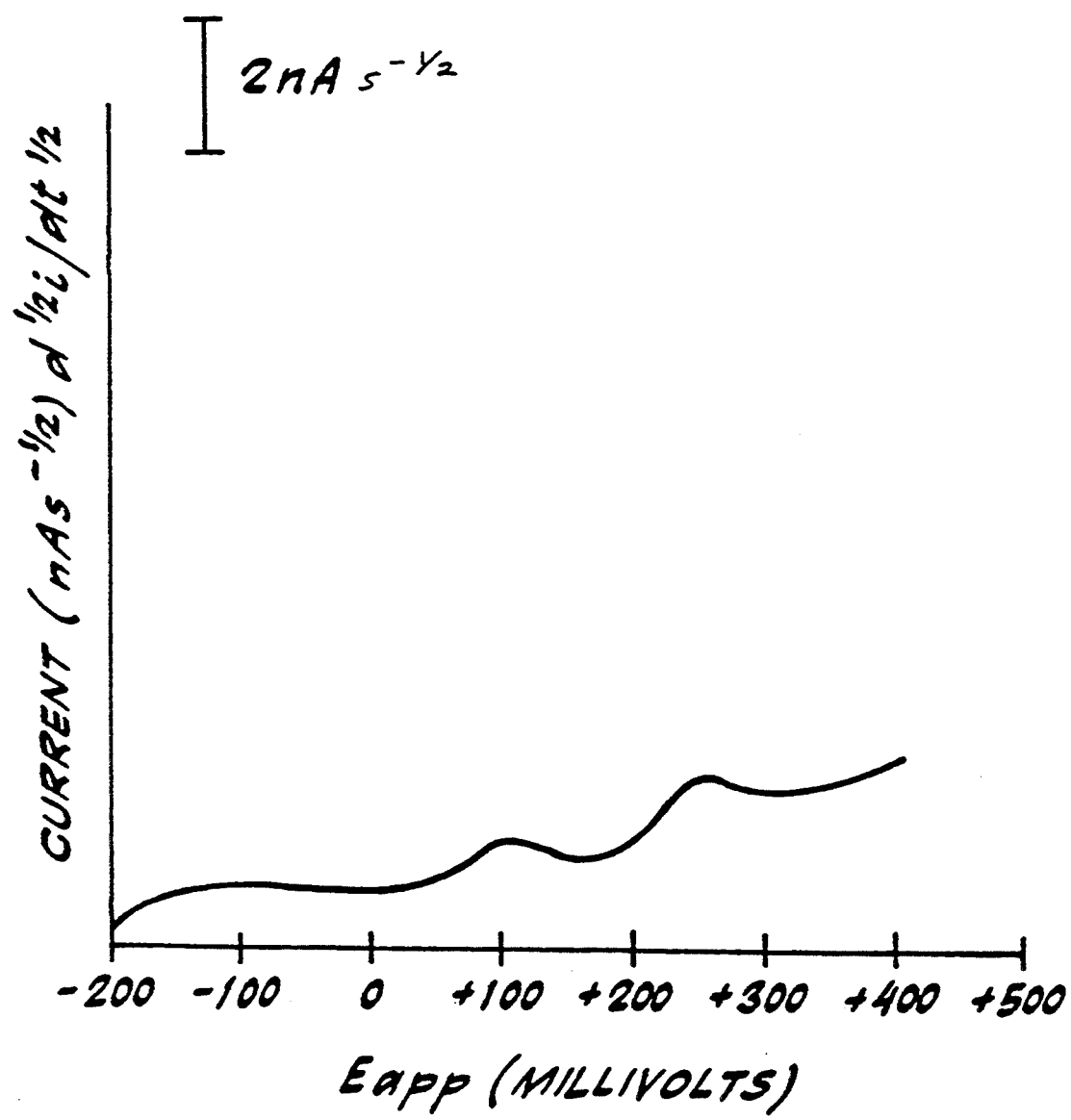
FIG. 49 is a semidifferential (semiderivative) voltammogram showing the in vitro detection of dopamine and serotonin (20 uM) in $PO_4$ buffer containing DA, 5-HT, DOPAC, 5-HIAA, AA, UA and HVA, pH 7.4 with an arachidic acid microelectrode made from a mixture of 1.5 g carbon (graphite), 1.24 cc extra heavy Nujol, and 100 mg arachidic acid, with the electrode conditioning taking place over a period of nine months. The typical period is 1-2 weeks.
Figure 50:
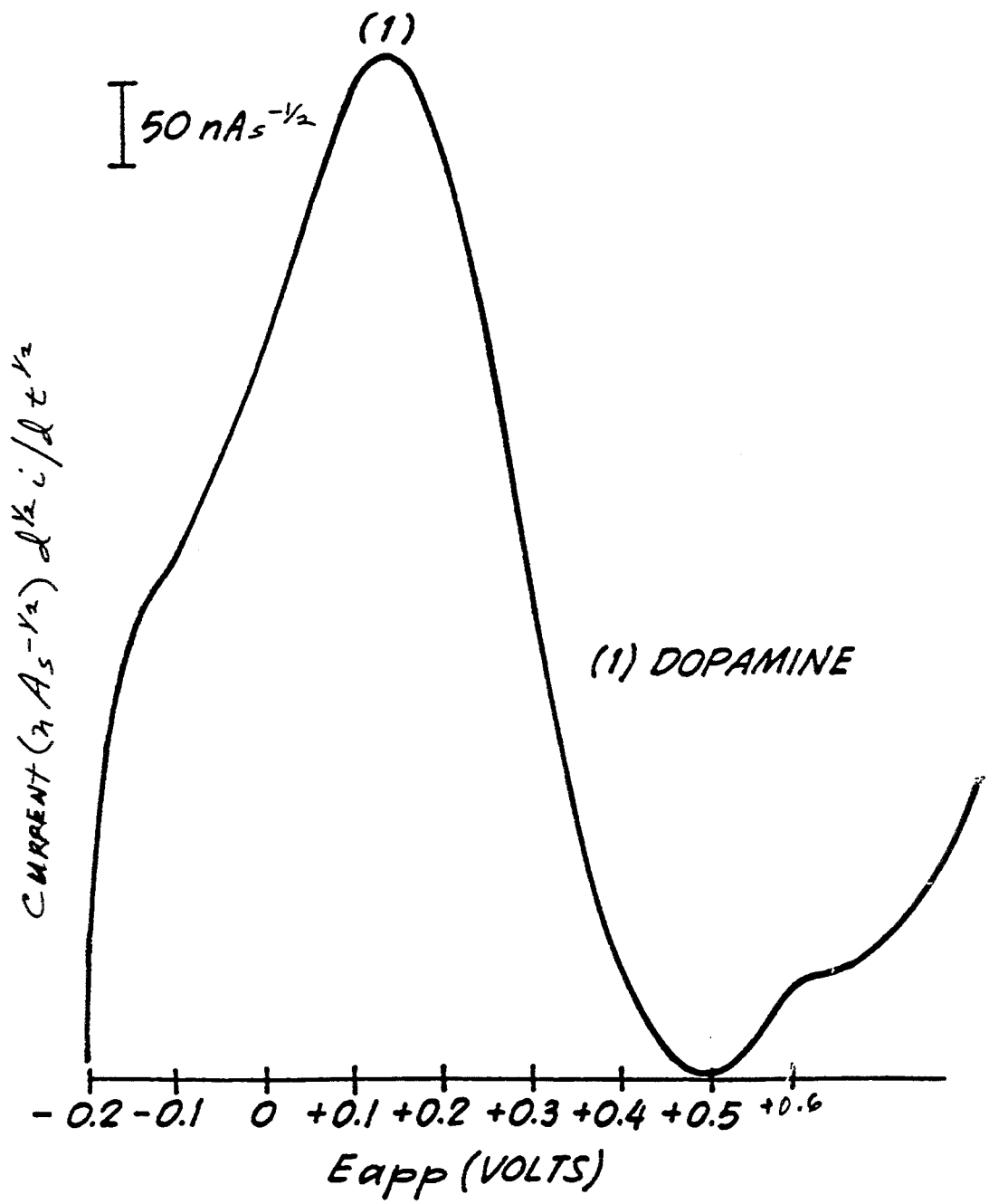
FIG. 50 is a semidifferential (semiderivative) voltammogram showing in vivo detection of dopamine (1), wherein the in vivo signal is enhanced by a palmitate vehicle. The electrode used to obtain this signal was implanted in the ventral tegmentum.

The arachidic acid electrode of Example 22 was reconditioned by repeating the conditioning steps of Example 22 at six and nine months after Example 22 was conducted. Then the electrode was employed for in vitro detection of dopamine (20 uM) and serotonin (20 uM) in phosphate buffer, at a pH of 7.4 by the steps described in Example 22. FIG. 49 shows a semiderivative (semidifferential) voltammogram showing this in vitro detection of dopamine (20 uM) and serotonin (20 uM).

Comparison of FIGS. 48 and 49 shows the arachidic acid electrode is more sensitive to serotonin and dopamine even when months separate the conditioning repetitions.

Additional examples of the results of the use of the method and apparatus of this invention are set forth in Patricia A. Broderick, "Rat Striatal Dopamine Release Mechanisms of Cocaine" *National Institute On Drug Abuse Research Monographs*, 1986; Patricia A. Broderick, "Delineation of Striatal Dopaminergic Autoreceptor Agonist Properties of -(−) Apomorphine with In Vivo Electrochemistry", *Annals of the New York Acad. Sc.*, Vol. No. 473, 1986; Patricia A. Broderick, "In Vivo Electrochemical Studies of Rat Striatal Dopamine and Serotonin Release after Morphine," *Life Sciences*, Vol. 36, p. 2269, 1985. Patricia A. Broderick, "Opiate Regulation of Mesolimbic Serotonin Release . . . ", *Neuropeptides* Vol. 5, p. 587, 1985; Patricia A. Broderick et al. "Decreased Release of Striatal Serotonin and Dopamine in the Diabetic Rat As Measured By In Vivo Voltammetry;" *The Endocrine Society*, 1985; Patricia A. Broderick, et al., "In Vivo Electrochemical and Behavioral Evidence for Specific Neural Substrates Modulated Differentially by Enkephalin in Rat Stimulant Stereotypy and Locomotion;" *Biological Psychiatry*, vol. 19, No. 1, p. 45, 1984; Patricia A. Broderick, et. al., "Similar Effects of an Enkephalin Analog on Mesolimbic Dopamine Release and Hyperactivity in Rats;" *Life Sci.* Vol. 33, p. 635, 1983; Patricia A. Broderick et al., "In Vivo Electrochemical Evidence for an Enkephalinergic Modulation Underlying Stereotyped Behaviour: Reversibility by Naloxone;" *Brain Res.* Vol. 269, p. 378, 1983. Patricia A. Broderick, "Striatal Neurochemistry of Dynorphin (1–13); In Vivo Electrochemical Semidifferential Analysis", *Neuropeptides*, Vol. 10/No. 4, p. 369, 1987; Patricia A. Broderick et al., Serotonergic Function in Diabetic Rats", *Biol. Psychiat.*, Vol. 24, No. 2, p. 234, 1988; Patricia A. Broderick, "Diabetes-Related Changes in L-Tryptophan-Induced Release of Striatal Biogenic Amines, *Diabetes*, Vol. 37, No. 7, p. 956, 1988; Patricia A. Broderick et al. "Dopamine and Serotonin in Rat Striatum During In Vivo Hypoxic Hypoxia, *Metab. Br. Diseases*, Vol. 4, No. 2, p. 143, 1989; Patricia A. Broderick, Distinguishing In Vitro Electrochemical Signatures for Norepinephrine and Dopamine, *Neurosci. Lett.*, Vol. 95, p. 275, 1988; Patricia A. Broderick et al, An In Vivo Voltammetric Analysis of Dopamine Release in Nucleus Accumbens: I. Morphine Effects. II. Cocaine Effects, *Adv. in the Biosciences*, Vol. 75, p. 209, 1989; Patricia A. Broderick, Characterizing Stearate Probes In Vitro for the Electrochemical Detection of Dopamine and Serotonin, *Brain Res.*, Vol. 495, No. 1 p. 115, 1989. Broderick, State-of-the Art Microelectrodes for In Vivo Voltammetry, 2 *Electroanalysis*, 241–251 (1990).

EXAMPLE 26
(Comparative Example)

A graphite microelectrode paste was made containing 1.5 g carbon (graphite), 1.00 cc extra heavy Nujol, and 100 mg stearic acid (ratio 1.5:1.0:0.1). The paste was prepared in accordance with the protocol described in Examples 2–12. A microelectrode containing this paste was made in accordance with the protocol described in Example 1. The in vitro voltammograms of Examples 26–43 are first trials of the microelectrode.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 $\mu$M DA and 10 $\mu$M 5-HT. The buffer was prepared according to the protocol set forth in Example 13, with the omission of AA, DOPAC, 5-HIAA and UA. In this voltammogram, DA had peak potential of 0.100 V, beginning and end potentials of 0.075 and 0.125 V, and a peak area of 2 mm$^2$. 5-HT had a peak potential of 0.315 V, beginning and end potentials of 0.285 and 0.375 V, and a peak area of 126 mm$^2$.

EXAMPLE 27

A graphite microelectrode paste was made containing 1.5 g carbon (graphite), 1.24 cc extra heavy Nujol, and 100 mg stearic acid (ratio 1.5:1.24:0.1). The paste was prepared in accordance with the protocol described in Examples 2–12. A microelectrode containing this paste was made in accordance with the protocol described in Example 1.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 $\mu$M DA and 10 $\mu$M 5-HT. The buffer was prepared according to the protocol set forth in Example 13, with the omission of AA, DOPAC, 5-HIAA and UA. In this voltammogram, DA had peak potential of 0.090 V, beginning and end potentials of 0.025 and 0.125 V, and a peak area of 9 mm$^2$. 5-HT had a peak potential of 0.300 V, beginning and end potentials of 0.250 and 0.350 V, and a peak area of 246 mm$^2$.

Comparison of the peak areas of voltammograms obtained with a 1.00 cc Nujol, stearic acid microelectrode of Example 26 and a 1.24 cc Nujol, stearic acid microelectrode indicated that a 1.24 cc Nujol, stearic acid microelectrode has greater sensitivity for detection of DA and 5-HT than does a 1.00 cc Nujol, stearic acid microelectrode. The DA peak had an area 4.5 times and the 5-HT peak had an area 1.95 times greater than the 1.00 cc Nujol, stearic acid DA and 5-HT peaks. In addition, the voltammogram obtained with 1.24 cc Nujol, stearic acid microelectrode had a well defined peak for 5-HT.

EXAMPLE 28

A graphite microelectrode paste was made containing 1.5 g carbon (graphite) 1.00 cc extra heavy Nujol and 100 mg arachidic acid (ratio 1.5:1.0:0.1). The paste was prepared in accordance with the protocol described in Examples 2–12. A microelectrode containing this paste was made in accordance with the protocol described in Example 1.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 $\mu$M DA and 10 $\mu$M 5-HT. The buffer was prepared according to the protocol set forth in Example 13, with the omission of AA, DOPAC, 5-HIAA and UA. In this voltammogram, DA had peak potential of 0.175 V, beginning and end potentials of 0.150 and 0.210 V, and a peak area of 2 mm$^2$. 5-HT had a peak potential of 0.305 V, beginning and end potentials of 0.240 and 0.340 V, and a peak area of 425 mm$^2$.

Comparison of the peak areas of voltammograms obtained with a 1.00 cc Nujol, stearic acid microelectrode of Example 26 and a 1.00 cc Nujol, arachidic acid microelectrode indicated that a 1.00 cc Nujol, arachidic acid microelectrode had greater sensitivity for detection of 5-HT than did a 1.00 cc Nujol, stearic acid microelectrode. The 5-HT peak had an area 3.37 times greater than the 1.00 cc Nujol, stearic acid peak area.

EXAMPLE 29

A graphite microelectrode paste was made containing 1.5 g carbon (graphite), 1.24 extra heavy Nujol and 100 mg arachidic acid (ratio 1.5:1.24:0.1). The paste was prepared in accordance with the protocol described in Examples 2–12. A microelectrode containing this paste was made in accordance with the protocol described in Example 1.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 $\mu$M DA and 10 $\mu$M 5-HT. The buffer was prepared according to the protocol set forth in Example 13, with the omission of AA, DOPAC, 5-HIAA and UA. In this voltammogram, DA had peak potential of 0.140 V, beginning and end potentials of 0.050 and 0.200 V, and a peak area of 16 mm$^2$. 5-HT had a peak potential of 0.275 V, beginning and end potentials of 0.215 and 0.350 V, and a peak area of 742.5 mm$^2$.

Comparison of the peak areas of voltammograms obtained with a 1.00 cc Nujol, stearic acid microelectrode of Example 26 and a 1.24 cc Nujol, arachidic acid microelectrode indicated that a 1.24 cc Nujol, arachidic acid microelectrode had greater sensitivity for detection of DA and 5-HT than did a 1.00 cc Nujol, stearic acid microelectrode. The DA peak had an area 8 times and the 5-HT peak had an area 5.9 times greater than the 1.00 cc Nujol, stearic acid peak areas, respectively.

EXAMPLE 30

A graphite microelectrode paste was made containing 1.5 g carbon (graphite), 1.24 cc extra heavy Nujol and 100 mg palmitic acid (ratio 1.5:1.24:0.1). The paste was prepared in accordance with the protocol described in Examples 2–12. A microelectrode containing this paste was made in accordance with the protocol described in Example 1.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 $\mu$M DA and 10 $\mu$M 5-HT. The buffer was prepared according to the protocol set forth in Example 13, with the omission of AA, DOPAC, 5-HIAA and UA. In this voltammogram, DA had peak potential of 0.120 V, beginning and end potentials of 0.050 and 0.175 V, and a peak area of 4 $mm^2$. 5-HT had a peak potential of 0.300 V, beginning and end potentials of 0.250 and 0.375 V, and a peak area of 282.75 $mm^2$.

Comparison of the peak areas of voltammograms obtained with a 1.00 cc Nujol, stearic acid microelectrode of Example 26 and a 1.24 cc Nujol, palmitic acid microelectrode indicated that 1.24 cc Nujol, palmitic acid microelectrode had greater sensitivity for detection of DA and 5-HT than did a 1.00 cc Nujol, stearic acid microelectrode. The DA peak had an area 2 times greater and the 5-HT peak had an area 2.2 times greater than the 1.00 cc Nujol, stearic acid peak areas, respectively.

EXAMPLE 31

A graphite microelectrode paste was made containing 1.5 g carbon (graphite), 1.24 cc extra heavy Nujol and 100 mg lauric acid (ratio 1.5:1.24:0.1). The paste was prepared in accordance with the protocol described in Examples 2–12. A microelectrode containing this paste was made in accordance with the protocol described in Example 1.

Figure 51:
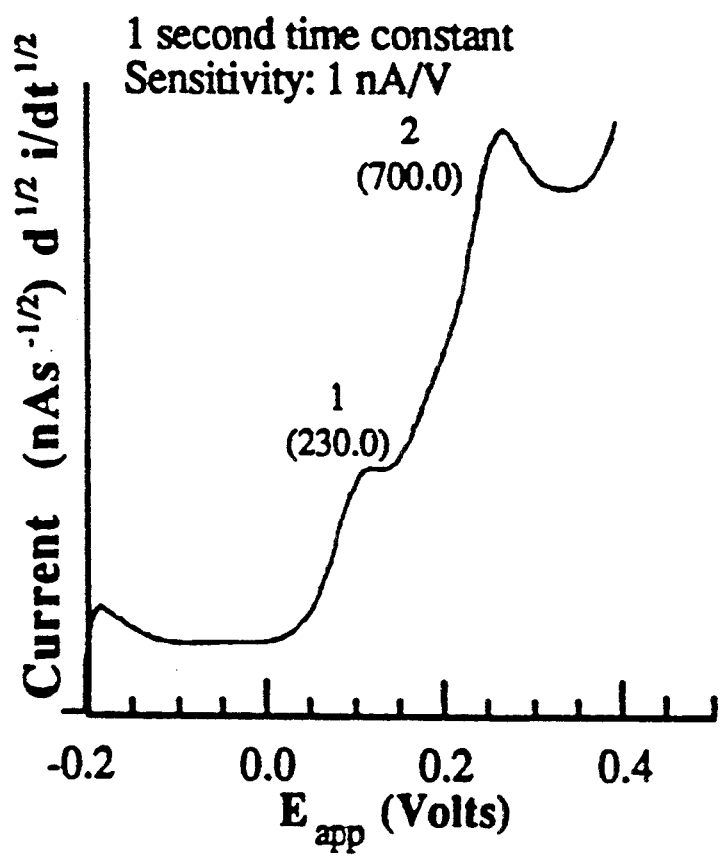
FIG. 51 is a semidifferential (semiderivative) voltammogram (1 second time constant; sensitivity 1 nA/V; room temperature) showing in vitro detection of dopamine and serotonin in a 0.01M physiological saline phosphate buffer, pH 7.4, 10 $\mu$M DA and 10 $\mu$M 5-HT, with a graphite microelectrode (150–200$\mu$ diameter; 500–750$\mu$ length) containing 1.5 g carbon (graphite), 1.24 cc extra heavy Nujol and 100 mg lauric acid.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 $\mu$M DA and 10 $\mu$M 5-HT. The buffer was prepared according to the protocol set forth in Example 13, with the omission of AA, DOPAC, 5-HIAA and UA. In this voltammogram, DA had peak potential of 0.115 V, beginning and end potentials of 0.050 and 0.175 V, and a peak area of 230 $mm^2$. 5-HT had a peak potential of 0.255 V, beginning and end potentials of 0.200 and 0.300 V, and a peak area of 700 $mm^2$. These data are shown in FIG. 51.

Comparison of the peak areas of voltammograms obtained with a 1.00 cc Nujol, stearic acid microelectrode of Example 26 and a 1.24 cc Nujol, lauric acid microelectrode indicated that a 1.24 cc Nujol, lauric acid microelectrode had greater sensitivity for detection of DA and 5-HT than did a 1.00 cc Nujol, stearic acid microelectrode. The DA peak had an area 115 times and the 5-HT peak had an area 5.6 times greater than the 1.00 cc Nujol, stearic acid 5-HT peak areas, respectively.

EXAMPLE 32

A graphite microelectrode paste was made containing 1.5 g carbon (graphite), 1.00 cc extra heavy Nujol, 50 mg arachidic acid and 50 mg stearic acid (ratio 1.5:1.00:0.1). The paste was prepared in accordance with the protocol described in Examples 2–12. A microelectrode containing this paste was made in accordance with the protocol described in Example 1.

Figure 52:
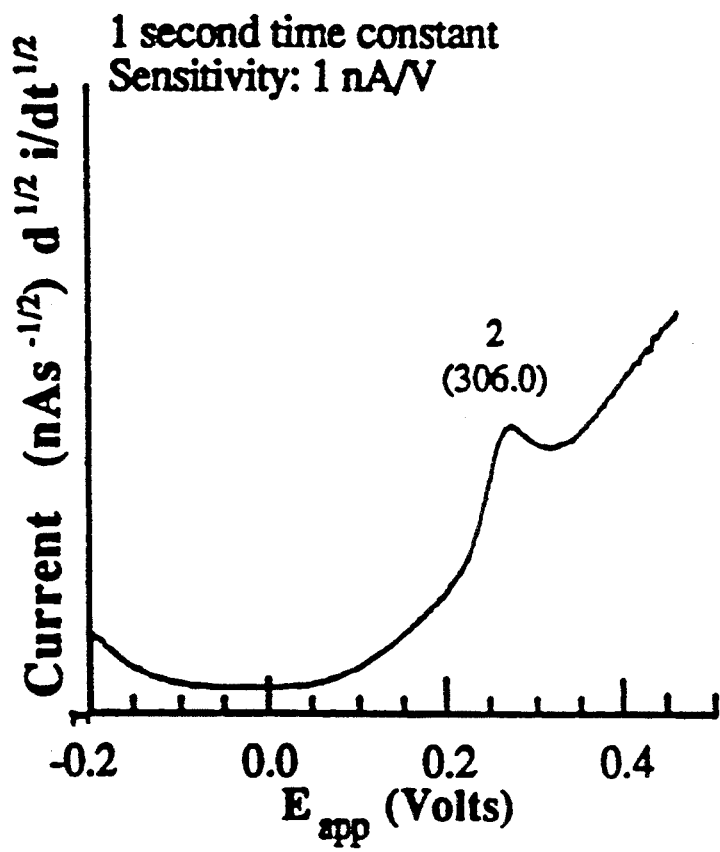
FIG. 52 is a semidifferential (semiderivative) voltammogram (1 second time constant; sensitivity 1 nA/V; room temperature) showing in Vitro detection of dopamine and serotonin in a 0.01M physiological saline phosphate buffer, pH 7.4, 10 $\mu$M DA and 10 $\mu$M 5-HT, with a graphite microelectrode (150–200$\mu$ diameter; 500–750$\mu$ length) containing 1.5 g carbon (graphite), 1.00 cc extra heavy Nujol, 50 mg arachidic and 50 mg stearic acid.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 $\mu$M DA and 10 $\mu$M 5-HT. The buffer was prepared according to the protocol set forth in Example 13, with the omission of AA, DOPAC, 5-HIAA and UA. In this voltammogram, there was no discernable detection of DA. 5-HT had a peak potential of 0.280 V, beginning and end potentials of 0.225 and 0.325 V, and a peak area of 306 $mm^2$. These data are shown in FIG. 52.

Comparison of the peak areas of voltammograms obtained with a 1.00 cc Nujol, stearic acid microelectrode of Example 26 and a 1.00 cc extra heavy Nujol, 50 mg arachidic acid and 50 mg stearic acid microelectrode indicated that a 1.00 cc Nujol, 50 mg arachidic acid, 50 mg stearic acid microelectrode had greater sensitivity for detection of 5-HT than did a 1.00 cc Nujol, stearic acid microelectrode. The 5-HT peak had an area 2.4 times greater than the 1.00 cc Nujol, stearic acid 5-HT peak and unexpectedly did not detect DA.

EXAMPLE 33

A graphite microelectrode paste was made containing 1.5 carbon (graphite), 1.24 cc extra heavy Nujol and 100 mg oleic acid (ratio 1.5:1.24:0.1). The paste was prepared in accordance with the protocol described in Examples 2–12. A microelectrode containing this paste was made in accordance with the protocol described in Example 1.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 $\mu$M DA and 10 $\mu$M 5-HT. The buffer was prepared according to the protocol set forth in Example 13, with the omission of AA, DOPAC, 5-HIAA and UA. In this voltammogram, DA had no discernable peak. 5-HT had a peak potential of 0.290 V, beginning and end potentials of 0.225 and 0.350 V, and a peak area of 196 $mm^2$.

Comparison of the peak areas of voltammograms obtained with a 1.00 cc Nujol, stearic acid microelectrode of Example 26 and a 1.24 cc Nujol, oleic acid microelectrode indicated that a 1.24 cc Nujol, oleic acid microelectrode had greater sensitivity for detection of 5-HT than did a 1.00 cc Nujol, stearic acid microelectrode. The 5-HT peak had an area 1.6 times greater than the 1.00 cc Nujol, stearic acid peak area.

EXAMPLE 34

A graphite microelectrode paste was made containing 1.5 g carbon (graphite), 1.24 cc extra heavy Nujol and 100 mg elaidic acid (ratio 1.5:1.24:0.1). The paste was prepared in accordance with the protocol described in Examples 2–12. A microelectrode containing this paste was made in accordance with the protocol described in Example 1.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 μM DA and 10 μM 5-HT. The buffer was prepared according to the protocol set forth in Example 13, with the omission of AA, DOPAC, 5-HIAA and UA. In this voltammogram, DA had peak potential of 0.100 V, beginning and end potentials of 0.040 and 0.150 V, and a peak area of 14 mm$^2$. 5-HT had a peak potential of 0.305 V, beginning and end potentials of 0.250 and 0.350 V, and a peak area of 408 mm$^2$.

Comparison of the peak areas of voltammograms obtained with a 1.00 cc Nujol, stearic acid microelectrode of Example 26 and a 1.24 cc Nujol, elaidic acid microelectrode indicated that a 1.24 cc Nujol, elaidic acid microelectrode had greater sensitivity for detection of DA and 5-HT than did a 1.00 cc Nujol, stearic acid microelectrode. The DA peak had an area 7 times and 5-HT peak had an area 3.2 times greater than the 1.00 cc Nujol, stearic acid peak areas, respectively.

EXAMPLE 35

A graphite microelectrode paste was made containing 1.5 g carbon (graphite), 1.24 cc extra heavy Nujol and 100 mg squalene (ratio 1.5:1.24:0.1). The paste was prepared in accordance with the protocol described in Examples 2–12. A microelectrode containing this paste was made in accordance with the protocol described in Example 1.

Figure 53:
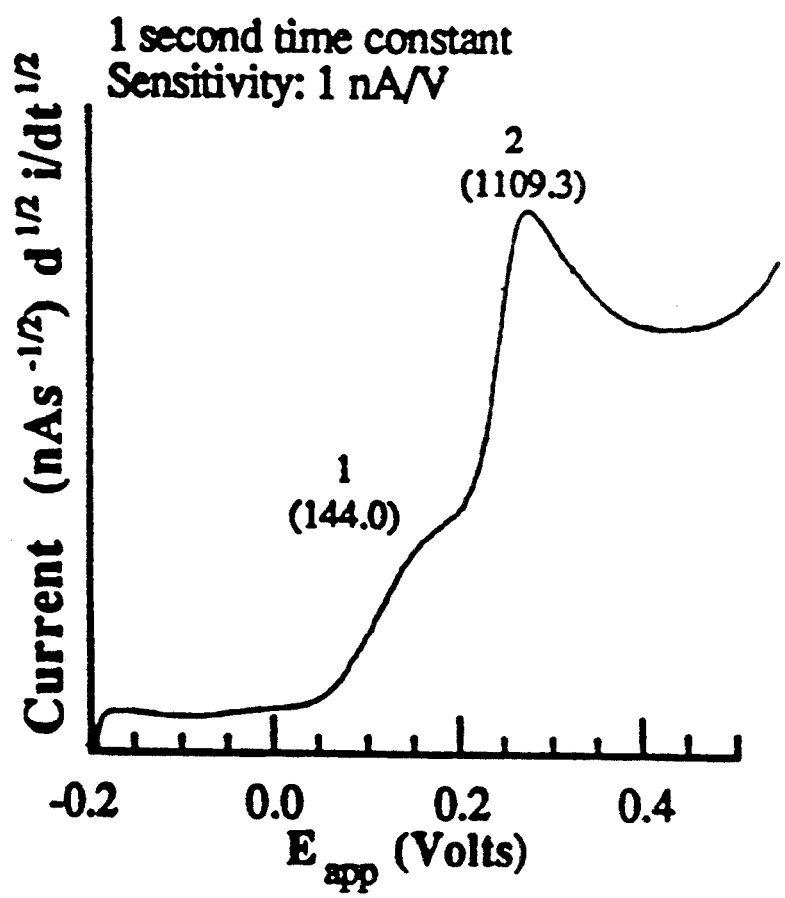
FIG. 53 is a semidifferential (semiderivative) voltammogram (1 second time constant; sensitivity 1 nA/V; room temperature) showing in vitro detection of dopamine and serotonin in a 0.01M physiological saline phosphate buffer, pH 7.4, 10 $\mu$M DA and 10 $\mu$M 5-HT, with a graphite microelectrode (150–200$\mu$ diameter; 500–750$\mu$ length) containing 1.5 g carbon (graphite), 1.24 cc extra heavy Nujol, and 100 mg squalene.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 μM DA and 10 μM 5-HT. The buffer was prepared according to the protocol set forth in Example 13, with the omission of AA, DOPAC, 5-HIAA and UA. In this voltammogram, DA had peak potential of 0.140 V, beginning and end potentials of 0.050 and 0.200 V, and a peak area of 144 mm$^2$. 5-HT had a peak potential of 0.280 V, beginning and end potentials of 0.215 and 0.365 V, and a peak area of 1109.25 mm$^2$. These data are shown in FIG. 53.

Comparison of the peak areas of voltammograms obtained with a 1.00 cc Nujol, stearic acid microelectrode of Example 26 and a 1.24 cc Nujol, squalene microelectrode indicated that a 1.24 cc Nujol, squalene microelectrode had greater sensitivity for detection of DA and 5-HT than did a 1.00 cc Nujol, stearic acid demicroelectrode. The DA peak had an area 72 times and the 5-HT peak had an area 8.8 times greater than the 1.00 cc Nujol, stearic acid peak areas, respectively.

EXAMPLE 36

A graphite microelectrode paste was made containing 1.5 g carbon (graphite), 1.00 cc extra heavy Nujol and 5 mg arachidic acid stearyl ester, a complex lipid, an acylglycerol (ratio 1.5:1.00:0.005). The paste was prepared in accordance with the protocol described in Examples 2–12. A microelectrode containing this paste was made in accordance with the protocol described in Example 1.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 μM DA and 10 μM 5-HT. The buffer was prepared according to the protocol set forth in Example 13, with the omission of AA, DOPAC, 5-HIAA and UA. In this voltammogram, DA had no discernable peak. 5-HT had a peak potential of 0.300 V, beginning and end potentials of 0.240 and 0.375 V, and a peak area of 650 mm$^2$.

Comparison of the peak areas of voltammograms obtained with a 1.00 cc Nujol, stearic acid microelectrode of Example 26 and a 1.00 cc Nujol, 5 mg arachidic acid stearyl ester microelectrode indicated that a 1.00 cc Nujol, 5 mg arachidic acid stearyl ester microelectrode had greater sensitivity for detection of 5-HT than did a 1.00 cc Nujol, stearic acid microelectrode. The 5-HT peak had an area 5.2 times greater than the 1.00 cc Nujol, stearic acid 5-HT peak area.

EXAMPLE 37

A graphite microelectrode paste was made containing 1.5 g carbon (graphite), 1.00 cc extra heavy Nujol and 10 mg arachidic acid stearyl ester (ratio 1.5:1.00:0.01). The paste was prepared in accordance with the protocol described in Examples 2–12. A microelectrode containing this paste was made in accordance with the protocol described in Example 1.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate: buffer, pH 7.4, 10 μM DA and 10 μM 5-HT. In this voltammogram, DA had no discernable peak and 5-HT had a peak potential of 0.310 V, beginning and end potentials of 0.250 and 0.390 V, and a peak area of 384 mm$^2$.

Comparison of the peak areas of voltammograms obtained with a 1.00 cc Nujol, stearic acid microelectrode of Example 26 and a 1.00 cc Nujol, 10 mg arachidic acid stearyl ester microelectrode indicated that a 1.00 cc Nujol, 10 mg arachidic acid stearyl ester microelectrode had greater sensitivity for detection of 5-HT than did a 1.24 cc Nujol, stearic acid microelectrode. The 5-HT peak had an area 3 times greater than the 1.00 cc Nujol, stearic acid 5-HT peak area.

EXAMPLE 38

A graphite microelectrode paste was made containing 1.5 g carbon (graphite), 1.24 cc extra heavy Nujol and 100 mg tripalmitin (ratio 1.5:1.24:0.1). The paste was prepared in accordance with the protocol described in Examples 2–12. A microelectrode containing this paste was made in accordance with the protocol described in Example 1.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 μM DA and 10 μM 5-HT. The buffer was prepared according to the protocol set forth in Example 13, with the omission of AA, DOPAC, 5-HIAA and UA. In this voltammogram, DA had no discernable peak. 5-HT had a peak potential of 0.305 V, beginning and end potentials of 0.240 and 0.340 V, and a peak area of 425 mm².

Comparison of the peak areas of voltammograms obtained with a 1.00 cc Nujol, stearic acid microelectrode of Example 26 and a 1.24 cc Nujol, tripalmitin microelectrode indicated that a 1.24 cc Nujol, tripalmitin microelectrode had greater sensitivity for detection of 5-HT than did a 1.00 cc Nujol, stearic acid microelectrode. The 5-HT peak had an area 3.4 times greater than the 1.00 cc Nujol, stearic acid 5-HT peak area.

EXAMPLE 39

A graphite microelectrode paste was made containing 1.5 g carbon (graphite), 1.24 cc extra heavy Nujol and 100 mg cardiolipin (ratio 1.5:1.24:0.1). The paste was prepared in accordance with the protocol described in Examples 2–12. A microelectrode containing this paste was made in accordance with the protocol described in Example 1.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 $\mu$M DA and 10 $\mu$M 5-HT. The buffer was prepared according to the protocol set forth in Example 13, with the omission of AA, DOPAC, 5-HIAA and UA. In this voltammogram, DA had peak potential of 0.165 V, beginning and end potentials of 0.100 and 0.225 V, and a peak area of 17 mm². 5-HT had a peak potential of 0.290 V, beginning and end potentials of 0.235 and 0.335 V, and a peak area of 588 mm².

Comparison of the peak areas of voltammograms obtained with a 1.00 cc Nujol, stearic acid microelectrode of Example 26 and a 1.24 cc Nujol, cardiolipin microelectrode indicated that a 1.24 cc Nujol, cardiolipin microelectrode had greater sensitivity for detection of DA and 5-HT than did a 1.00 cc Nujol, stearic acid microelectrode. The DA peak had an area 8.5 times and the 5-HT peak had an area 4.7 times greater than the 1.00 cc Nujol, stearic acid peak areas, respectively.

EXAMPLE 40

A graphite microelectrode paste was made containing 1.5 g carbon (graphite), 1.00 cc extra heavy Nujol, and 10 mg N-stearoyl-DL-dihydrosphingosine (ratio 1.5:1.00:0.01). The paste was prepared in accordance with the protocol described in Examples 2–12. A microelectrode containing this paste was made in accordance with the protocol described in Example 1.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 $\mu$M DA and 10 $\mu$M 5-HT. The buffer was prepared according to the protocol set forth in Example 13, with the omission of AA, DOPAC, 5-HIAA and UA. In this voltammogram, DA had peak potential of 0.150 V, beginning and end potentials of 0.075 and 0.200 V, and a peak area of 24 mm². 5-HT had a peak potential of 0.285 V, beginning and end potentials of 0.215 and 0.365 V, and a peak area of 825 mm².

Comparison of the peak areas of voltammograms obtained with a 1.00 cc Nujol, stearic acid microelectrode of Example 26 and a 1.00 cc Nujol, 10 mg N-stearoyl-DL-dihydrosphingosine microelectrode indicated that a 1.00 cc Nujol, 10 mg N-stearoyl-DL-dihydrosphingosine microelectrode had greater sensitivity for detection of DA and 5-HT than did a 1.00 cc Nujol, stearic acid microelectrode. The DA peak had an area 12 times and the 5-HT peak had an area 6.5 times greater than the 1.00 cc Nujol, stearic acid peak areas, respectively.

EXAMPLE 41

A graphite microelectrode paste was made containing 1.5 g carbon (graphite), 1.24 cc extra heavy Nujol, and 66 mg N-stearoyl-DL-dihydrosphingosine, a complex lipid, a sphingosine (ratio 1.5:1.24:0.066). The paste was prepared in accordance with the protocol described in Examples 2–12. A microelectrode containing this paste was made in accordance with the protocol described in Example 1.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 $\mu$M DA and 10 $\mu$M 5-HT. The buffer was prepared according to the protocol set forth in Example 13, with the omission of AA, DOPAC, 5-HIAA and UA. In this voltammogram, DA had peak potential of 0.140 V, beginning and end potentials of 0.065 and 0.200 V, and a peak area of 44 mm². 5-HT had a peak potential of 0.290 V, beginning and end potentials of 0.225 and 0.325 V, and a peak area of 522 mm².

Comparison of the peak areas of voltammograms obtained with a 1.00 cc Nujol, stearic acid microelectrode of Example 26 and a 1.24 cc Nujol, 66 mg N-stearoyl-DL-dihydrosphingosine microelectrode indicated that a 1.24 cc Nujol, 66 mg N-stearoyl-DL-dihydrosphingosine microelectrode had greater sensitivity for detection of DA and 5-HT than did a 1.00 cc Nujol, stearic acid microelectrode. The DA peak had an area 22 times and the 5-HT peak had an area 4.1 times greater than the 1.00 cc Nujol, stearic acid peak areas, respectively.

EXAMPLE 42

A graphite microelectrode paste was made containing 1.5 g carbon (graphite), 1.00 cc extra heavy Nujol, and 10 mg N-stearoyl cerebroside (ratio 1.5:1.00:0.01). The paste was prepared in accordance with the protocol described in Examples 2–12. A microelectrode containing this paste was made in accordance with the protocol described in Example 1.

Figure 54:
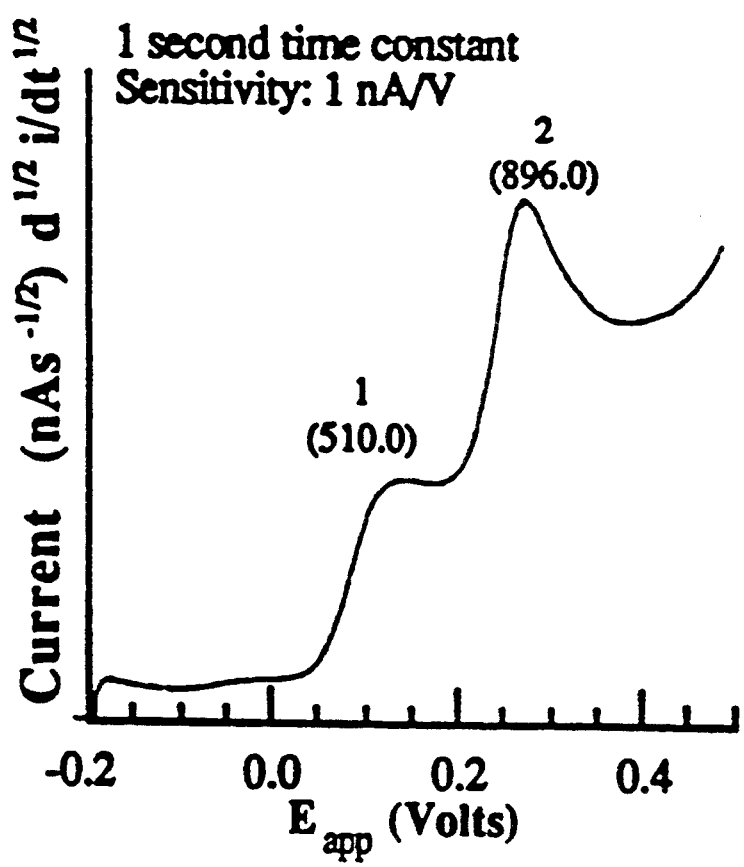
FIG. 54 is a semidifferential (semiderivative) voltammogram (1 second time constant; sensitivity 1 nA/V; room temperature) showing in vitro detection of dopamine and serotonin in a 0.01M physiological saline phosphate buffer, pH 7.4, 10 $\mu$M DA and 10 $\mu$M 5-HT, with a graphite microelectrode (150–200 $\mu$ diameter; 500–750$\mu$ length) containing 1.5 g carbon (graphite), 1.00 cc extra heavy Nujol, and 10 mg N-stearoyl cerebroside.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 $\mu$M DA and 10 $\mu$M 5-HT. The buffer was prepared according to the protocol set forth in Example 13, with the omission of AA, DOPAC, 5-HIAA and UA. In this voltammogram, DA had peak potential of 0.140 V, beginning and end potentials of 0.050 and 0.200 V, and a peak area of 510 mm². 5-HT had a peak potential of 0.275 V, beginning and end potentials of 0.225 and 0.325 V, and a peak area of 896 mm². These data are shown in FIG. 54.

Comparison of the peak areas of voltammograms obtained with a 1.00 cc Nujol, stearic acid microelectrode of Example 26 and a 1.00 cc Nujol, 10 mg N-stearoyl cerebroside microelectrode indicated that a 1.00 cc Nujol, 10 mg N-stearoyl cerebroside microelectrode had greater sensitivity for detection of DA and 5-HT than did a 1.00 cc Nujol, stearic acid microelectrode. The DA peak had an area 255 times and the 5-HT peak had an area 7.1 times greater than the 1.00 cc Nujol, stearic acid peak areas, respectively.

EXAMPLE 43

A graphite microelectrode paste was made containing 1.5 g carbon (graphite), 1.24 cc extra heavy Nujol, and 66 mg N-stearoyl cerebroside (ratio 1.5:1.24:0.066). The paste was prepared in accordance with the protocol described in Examples 2–12. A microelectrode containing this paste was made in accordance with the protocol described in Example 1.

This microelectrode was used in the electroanalytical technique described in Example 14 to obtain a semidifferential (semiderivative) voltammogram (1 second time constant; sensitivity 1 nA/V; room temperature) showing in vitro detection of DA and 5-HT in a 0.01M physiological saline phosphate buffer, pH 7.4, 10 $\mu$M DA and 10 $\mu$M 5-HT. The buffer was prepared according to the protocol set forth in Example 13, with the omission of AA, DOPAC, 5-HIAA and LIA. In this voltammogram, DA had peak potential of 0.155 V, beginning and end potentials of 0.065 and 0.215 V, and a peak area of 14 mm$^2$. 5-HT had a peak potential of 0.295 V, beginning and end potentials of 0.240 and 0.340 V, and a peak area of 432 mm$^2$.

Comparison of the peak areas of voltammograms obtained with a 1.00 cc Nujol, stearic acid microelectrode of Example 26 and a 1.24 cc Nujol, 66 mg N-stearoyl-cerebroside microelectrode indicated that a 1.24 cc Nujol, 66 mg N-stearoyl cerebroside microelectrode had greater sensitivity for detection of DA and 5-HT than did a 1.00 cc Nujol, stearic acid microelectrode. The DA peak had an area 7 times and 5-HT peak had an area 3.4 times greater than the 1.00 cc Nujol, stearic acid peak areas, respectively.

EXAMPLE 44

The microelectrode prepared as described in Example 26, containing 1.5 g carbon (graphite), 1.00 cc extra heavy Nujol, and 100 mg stearic acid (ratio 1.5:1.00:0.1) was used to obtain comparative data to show in vivo detection of DA and/or 5-HT and/or other biogenic amines with microelectrodes stereotaxically implanted in the nucleus accumbens of chloral hydrate anesthetized, virus free, male Sprague-Dawley laboratory rats, weighing 337–359 g. Twelve recordings (Scans Nos. 1–12) were obtained at ten minute intervals. Each biogenic chemical was detected in units of seconds. Each series of voltammograms show either the decrease in signal sensitivity until a reproducible baseline is achieved or the unexpected property of immediate, or earlier baseline or more stable baseline, in addition to showing the unexpected property of exhibiting a smaller decrease in signal sensitivity, as compared to a 1.00 cc Nujol, stearic acid microelectrode.

Peak areas were calculated by drawing a line from beginning potential to end potential and multiplying the peak height (mm) at peak potential of each electrochemical signal by the width (mm) of each electrochemical signal at ½ the peak height (mm). Each peak area was converted from a 5 second time constant to a 1 second time constant by multiplying by 2.

In Scans 1–12, Signal 1 (DA) had a peak potential at 0.140 V, beginning and end potentials at 0.050 and 0.200 V and had peak areas of 598 mm$^2$, 396 mm$^2$, 378 mm$^2$, 231 mm$^2$, 176 mm$^2$, 108 mm$^2$, 108 mm$^2$, 72 mm$^2$, 88 mm$^2$, 94.5 mm$^2$, 105 mm$^2$ and 105 mm$^2$, respectively. Signal 2 (5-HT) had a peak potential at 0.275 V, beginning and end potentials at 0.225 and 0.325 V, and had peak areas of 0 mm$^2$ (not yet measurable), 66 mm$^2$, 55 mm$^2$, 104 mm$^2$, 96 mm$^2$, 78 mm$^2$, 52 mm$^2$, 48 mm$^2$, 20 mm$^2$, 20 mm$^2$, 15 mm$^2$ and 16.50 mm$^2$, respectively. In addition, Signal 4, a putative biogenic chemical, tentatively tryptophan or tryptophan derivatives, a 0.610 V peak potential, beginning and end potentials of 0.540 and 0.675 V, first detected in Recording 3 (Scan 3), and had peak areas of 3478 mm$^2$, 2100 mm$^2$, 1320 mm$^2$, 1080 mm$^2$, 1020 mm$^2$, 870 mm$^2$, 480 mm$^2$, 546 mm$^2$, 475 mm$^2$ and 468 mm$^2$, respectively. Finally, Signal 5, a putative biogenic chemical, tentatively an amino acid or neuropeptide, had a 0.770 V peak potential, had beginning and end potentials of 0.700 and 0.810 V, first detected in Scan 4, had peak areas of 2024 mm$^2$, 1584 mm$^2$, 1216 mm$^2$, 1024 mm$^2$, 930 mm$^2$, 1020 mm$^2$, 1015 mm$^2$, 990 mm$^2$ and 957 mm$^2$, respectively.

A stable, reproducible baseline for DA was achieved after about 110–120 minutes. 5-HT was not clearly stabilized even at the 110–120 minute mark.

EXAMPLE 45

The microelectrode prepared as described in Example 27, containing 1.5 g carbon (graphite), 1.24 cc extra heavy Nujol, and 100 mg stearic acid (ratio 1.5:1.24:0.1) was used to obtain comparative data to show in vivo detection of DA and/or 5-HT and/or other biogenic amines with microelectrodes stereotaxically implanted in the nucleus accumbens of chloral hydrate anesthetized, virus free, male Sprague-Dawley laboratory rats, weighing 337–359 g. Twelve recordings (Scans Nos. 1–12) were obtained at ten minute intervals. Each biogenic chemical was detected in units of seconds. Each series of voltammograms show either the decrease in signal sensitivity until a reproducible baseline is achieved or the unexpected property of immediate, or earlier baseline or more stable baseline, in addition to showing the unexpected property of exhibiting a smaller decrease in signal sensitivity, as compared to a 1.00 cc Nujol, stearic acid microelectrode.

Peak areas were calculated by drawing a line from beginning potential to end potential and multiplying the peak height (mm) at peak potential of each electrochemical signal by the width (mm) of each electrochemical signal at ½ the peak height (mm). Each peak area was converted from a 5 second time constant to a 1 second time constant by multiplying by 2.

In Scans 1–12, Signal 1 (DA) had a peak potential at 0.140 V, beginning and end potentials at 0.050 and 0.200 V, and peak areas of 1116 mm$^2$, 400 mm$^2$, 299 mm$^2$, 198 mm$^2$, 168 mm$^2$, 168 mm$^2$, 168 mm$^2$, 168 mm$^2$, 172 mm$^2$, 178.0 mm$^2$, 168 mm$^2$ and 168 mm$^2$, respectively. Signal 2 (5-HT) had a peak potential at 0.275 V, beginning and end potentials at 0.210 and 0.310 V, and peak areas of 0 mm$^{2(not\ yet\ measurable)}$, 24 mm$^2$, 68 mm$^2$, 84 mm$^2$, 78 mm$^2$, 90 mm$^2$, 78 mm$^2$, 78 mm$^2$, 56 mm$^2$, 56 mm$^2$, 56 mm$^2$ and 56 mm$^2$, respectively. Signal 3, a putative biogenic chemical. (homovanillic acid (HVA)), first measurably detected in Scan No. 5, had a peak potential at 0.435 V, beginning and end potentials at 0.360 and 0.485, had peak areas of 16 mm$^2$, 22 mm$^2$, 24 mm$^2$, 22 mm$^2$, 76 mm$^2$, 75 mm$^2$, 88 mm$^2$ and 90 mm$^2$, respectively. Signal 4, a putative biogenic chemical (tentatively tryptophan or tryptophan derivatives), first measurably detected in Scan No. 2, had a peak potential at 0.605 V, beginning and end potentials at 0.50 and 0.670 V, and peak areas of 1517 mm$^2$, 1178 mm$^2$, 900 mm$^2$, 782 mm$^2$, 792 mm$^2$, 748 mm$^2$, 714 mm$^2$, 546 mm$^2$, 546 mm$^2$, 474.0 mm$^2$ and 499 mm$^2$, respectively. Signal 5, a putative biogenic chemical (tentatively an amino acid or neuropeptide), first measurably detected in Scan No. 2, had a peak potential at 0.760 V, beginning and end potentials at 0.675 and 0.800 V, and peak areas of 168 mm$^2$, 170 mm$^2$, 133 mm$^2$, 136 mm$^2$, 120 mm$^2$, 120 mm$^2$, 120 mm$^2$, 230 mm$^2$, 250 mm$^2$, 216 mm$^2$ and 216 mm$^2$, respectively.

Stable, reproducible baselines for DA and 5-HT were obtained after about 50 and 90 minutes, respectively.

Comparison of Scan 12 of the 1.00 cc Nujol, stearic acid microelectrode of Example 44 (FIG. 55) and 1.24 cc Nujol, stearic acid microelectrode (FIG. 56) indicated that a 1.24 cc Nujol, stearic acid microelectrode had greater sensitivity for detection of DA and 5-HT in vivo than did a 1.00 cc Nujol, stearic acid microelectrode. The DA peak had an area 1.6 times and the 5-HT peak had an area 3.4 times greater than the 1.00 cc Nujol, stearic acid peak areas, respectively. Additionally, a 1.24 cc Nujol, stearic acid microelectrode unexpectedly detected a biogenic chemical had a peak potential at 0.435 V (Signal 3; putative HVA), which a 1.00 cc Nujol, stearic acid microelectrode did not detect. Baseline for DA occurred in approximately 50 minutes. This was 60 to 70 minutes earlier than the stearic acid, 1.00 cc Nujol electrode. Baseline for 5-HT with the novel 1.24 cc Nujol, stearic acid microelectrode was achieved in 90 minutes, whereas baseline was not yet achieved in 110-120 minutes with the 1.00 cc Nujol, stearic acid microelectrode.

EXAMPLE 46

The microelectrode prepared as described in Example 28, containing 1.5 g carbon (graphite), 1.00 cc extra heavy Nujol, and 100 mg arachidic acid (ratio 1.5:1.00:0.1) was used to obtain comparative data to show in vivo detection of DA and/or 5-HT and/or other biogenic amines with microelectrodes stereotaxically implanted in the nucleus accumbens of chloral hydrate anesthetized, virus free, male Sprague-Dawley laboratory rats, weighing 337–359 g. Twelve recordings (Scans Nos. 1-12) were obtained at ten minute intervals. Each biogenic chemical was detected in units of seconds. Each series of voltammograms show either the decrease in signal sensitivity until a reproducible baseline was achieved or the unexpected property of immediate, or earlier baseline or more stable baseline, in addition to showing the unexpected property of exhibiting a smaller decrease in signal sensitivity, as compared to a 1.00 cc Nujol, stearic acid microelectrode.

Peak areas were calculated by drawing a line from beginning potential to end potential and multiplying the peak height (mm) at peak potential of each electrochemical signal by the width (mm) of each electrochemical signal at ½ the peak height (mm). Each peak area was converted from a 5 second time constant to a 1 second time constant by multiplying by 2.

In Scans 1-12, Signal 1 (DA) had a peak potential at 0.140 V, beginning and end potentials at 0.050 and 0.200 V, and peak areas of 616 mm$^2$, 352 mm$^2$, 273 mm$^2$, 276 mm$^2$, 242 mm$^2$, 210 mm$^2$, 147 mm$^2$, 150 mm$^2$, 150 mm$^2$, 140 mm$^2$, 140 mm$^2$ and 140 mm$^2$, respectively. Signal 2 (5-HT), first measurably detected in Scan 5, had a peak potential at 0.275 V, beginning and end potentials at 0.225 and 0.325 V, and peak areas of 7 mm$^2$, 7 mm$^2$, 10 mm$^2$, 11 mm$^2$, 10 mm$^2$, 10 mm$^2$, 15 mm$^2$ and 16.5 mm$^2$, respectively. Signal 3, a putative biogenic chemical (HVA), had a peak potential at 0.440 V, beginning and end potentials at 0.365 and 0.490 V, and peak areas of 60 mm$^2$, 60 mm$^2$, 75 mm$^2$, 75 mm$^2$, 56 mm$^2$, 52 mm$^2$, 105 mm$^2$, 90 mm$^2$, 85.5 mm$^2$, 90 mm$^2$, 95 mm$^2$ and 95 mm$^2$, respectively. Signal 4, a putative biogenic chemical (tentatively tryptophan or tryptophan derivatives), had a peak potential at 0.605 V, beginning and end potentials at 0.525 and 0.665 V, and peak areas of 1886 mm$^2$, 544 mm$^2$, 518 mm$^2$, 522 mm$^2$, 493 mm$^2$, 504 mm$^2$, 390 mm$^2$, 385 mm$^2$, 412.5 mm$^2$, 397.5 mm$^2$, 397.5 mm$^2$ and 403 mm$^2$, respectively. Signal 5, a putative biogenic chemical (tentatively an amino acid or neuropeptide), first measurably detected in Scan 2, had a peak potential at 0.760 V, had peak areas of 136 mm$^2$, 136 mm$^2$, 170 mm$^2$, 136 mm$^2$, 148 mm$^2$, 210 mm$^2$, 220 mm$^2$, 220 mm$^2$, 200 mm$^2$, 209 mm$^2$ and 210 mm$^2$, respectively.

A stable, reproducible, baseline for DA was obtained after about 60–70 minutes.

Figure 57:
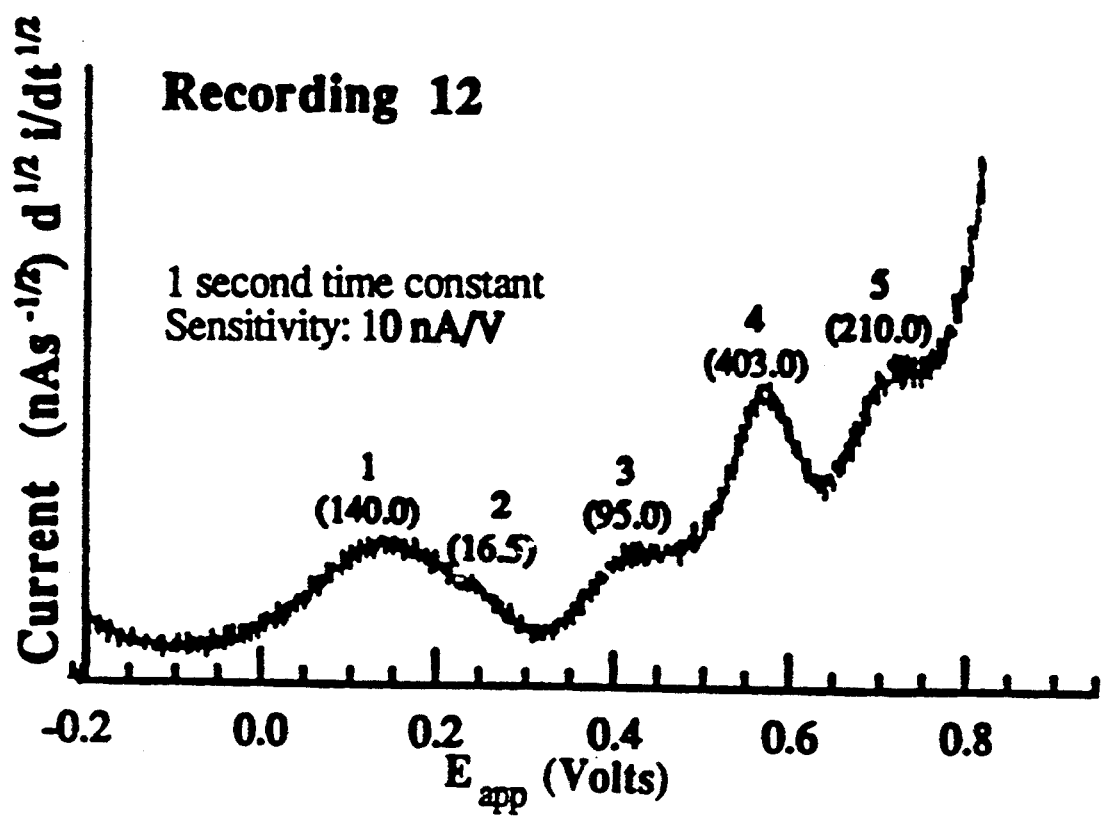
FIG. 57 is a semidifferential (semiderivative) voltammogram (1 second time constant; sensitivity 10 nA/V; body temperature) recording 12 of scans taken at ten minute intervals showing in vivo detection of dopamine, serotonin and other biogenic chemicals in a rat using a graphite microelectrode (diameter ranging between 150u-200u; 500-750μ length) containing 1.5 g carbon (graphite), 1.00 cc extra heavy Nujol and 100 mg arachidic acid.

Comparison of Scan 12 indicates that a 1.00 cc Nujol, arachidic acid microelectrode (FIG. 57) had greater sensitivity for detection of DA in vivo than does a 1.00 cc Nujol, stearic acid microelectrode. The DA peak had an area 1.3 times greater than the 1.00 cc Nujol, stearic acid DA peak area. With an 1.00 cc Nujol, arachidic acid microelectrode, the baseline for DA was achieved after approximately 70 minutes, approximately 40 minutes earlier than the 1.00 cc Nujol, stearic acid microelectrode. In addition, an arachidic acid microelectrode unexpectedly detects a putative biogenic chemical had a peak potential at 0.440 V (Signal 3; putative HVA), which the 1.00 cc Nujol, stearic acid microelectrode does not.

EXAMPLE 47

The microelectrode prepared as described in Example 29, 1.5 g carbon (graphite), 1.24 cc extra heavy Nujol, and 100 mg arachidic acid (ratio 1.5:1.24:0.1) was used to obtain comparative data to show in vivo detection of DA and/or 5-HT and/or other biogenic amines with microelectrodes stereotaxically implanted in the nucleus accumbens of chloral hydrate anesthetized, virus free, male Sprague-Dawley laboratory rats, weighing 337–359 g. Twelve recordings (Scans Nos. 1-12) were obtained at ten minute intervals. Each biogenic chemical was detected in units of seconds. Each series of voltammograms show either the decrease in signal sensitivity until a reproducible baseline was achieved or the unexpected property of immediate, or earlier baseline or more stable baseline, in addition to showing the unexpected property of exhibiting a smaller decrease in signal sensitivity, as compared to a 1.00 cc Nujol, stearic acid microelectrode.

Peak areas were calculated by drawing a line from beginning potential to end potential and multiplying the peak height (mm) at peak potential of each electrochemical signal by the width (mm) of each electrochemical signal at ½ the peak height (mm). Each peak area was converted from a 5 second time constant to a 1 second time constant by multiplying by 2.

In Scans 1-12 of the 1.24 cc Nujol, arachidic acid microelectrode, Signal 1 (DA) had a peak potential at 0.135 V, beginning and end potentials at 0.075 and 0.225 V, and peak areas of 672 mm$^2$, 462 mm$^2$, 360 mm$^2$, 294 mm$^2$, 273 mm$^2$, 231 mm$^2$, 220 mm$^2$, 210 mm$^2$, 180 mm$^2$, 180 mm$^2$, 204 mm$^2$ and 187 mm$^2$, respectively. Signal 2 (5-HT), first measurably detected at Scan 5, had a peak potential at 0.275 V, beginning and end potentials at 0.230 and 0.325 V, and peak areas of 4 mm$^2$, 0 mm$^2$, 4 mm$^2$, 8 mm$^2$, 9 mm$^2$, 10 mm$^2$, 9 mm$^2$ and 10 mm$^2$, respectively. Signal 3, a putative biogenic chemical (HVA), had a peak potential at 0.435 V, beginning and end potentials at 0.360 and 0.485 V, and peak areas of 195 mm$^2$, 228 mm$^2$, 136 mm$^2$, 90 mm$^2$, mm$^2$, 0 mm$^2$, 75 mm$^2$, 52 mm$^2$, 56 mm$^2$, 60 mm$^2$, 52 mm$^2$, 52 mm$^2$ and 80 mm$^2$, respectively Signal 4, a putative biogenic chemical (tentatively tryptophan or tryptophan derivatives), had a peak potential at 0.610 V, beginning and end potentials at 0.525 and 0.675 V, and peak areas of 2320 mm$^2$, 2760 mm$^2$, 1026 mm$^2$, 924 mm$^2$, 756 mm$^2$, 640 mm$^2$, 494 mm$^2$, 494 mm$^2$, 396 mm$^2$, 418 mm$^2$, 418 mm$^2$ and 378 mm$^2$, respectively. Signal 5, a putative biogenic chemical (tentatively an amino acid or neuropeptide), first detected at Scan 2, had a peak potential at 0.760 V, beginning and end potentials at 0.685 and 0.810 V, and peak areas of 435 mm$^2$, 74 mm$^2$, 609 mm$^2$, 456 mm$^2$, 360 mm$^2$, 324 mm$^2$, 224 mm$^2$, 192 mm$^2$, 165 mm$^2$, 155 mm$^2$, 80 mm$^2$, respectively.

Figure 58:
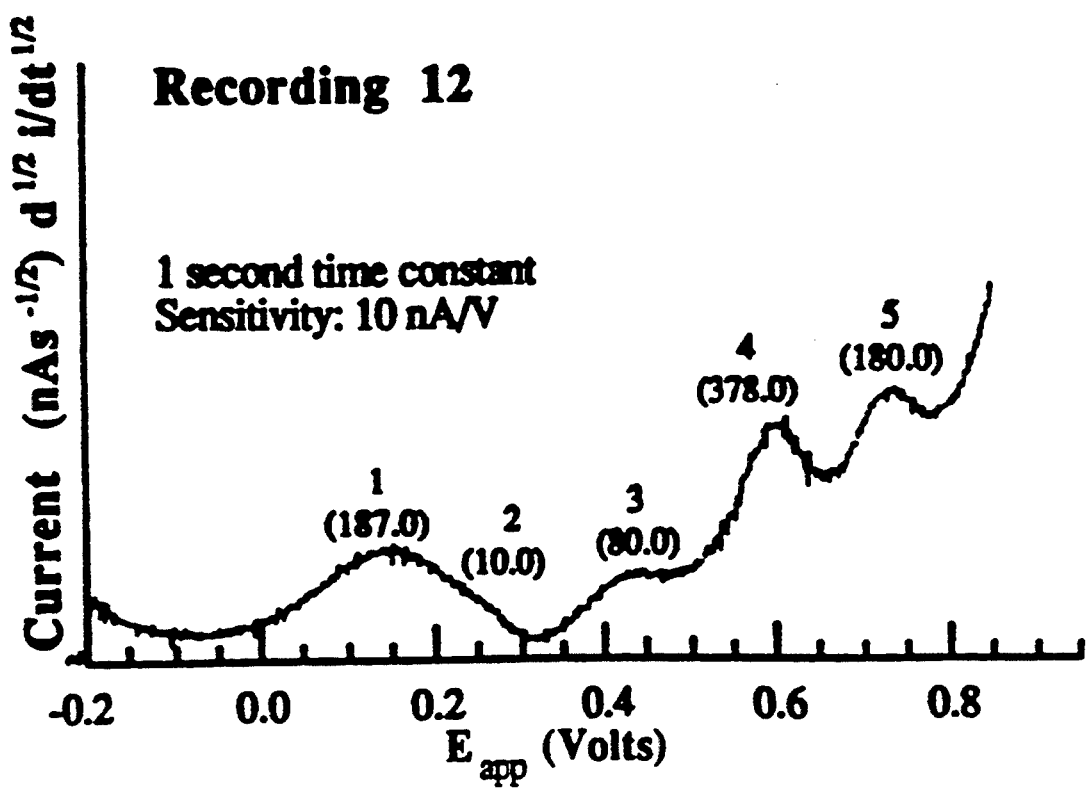
FIG. 58 is a semidifferential (semiderivative) voltammogram (1 second time constant; sensitivity 10 nA/V; body temperature) recording 12 of scans taken at ten minute intervals showing in vivo detection of dopamine, serotonin and other biogenic chemicals in a rat using a graphite microelectrode (diameter ranging between 150u-200u; 500-750μ length) containing 1.5 g carbon (graphite), 1.24 cc extra heavy Nujol and 100 mg arachidic acid.

Comparison of Scans 12 of 1.00 cc Nujol, stearic acid of Example 44 and 1.24 cc Nujol, arachidic acid microelectrodes indicated that a 1.24 cc Nujol, arachidic acid microelectrode (FIG. 58) had greater sensitivity for detection of DA and less sensitivity for detection of 5-HT in vivo than does a 1.00 cc Nujol, stearic acid microelectrode. The DA peak had an area 1.8 times greater than the 1.00 cc Nujol, stearic acid DA peak area. A 1.24 cc Nujol, arachidic acid microelectrode detected a putative biogenic chemical, had a peak potential at 0.435 V (Signal 3; putative HVA), which the 1.00 cc Nujol, stearic acid microelectrode does not detect. Baseline for DA was achieved in 90 minutes, 20 minutes earlier than the a 1.00 cc Nujol, stearic acid microelectrode. Baseline for the 5-HT signal was achieved in 80-90 minutes. Thus, the 1.24 cc Nujol, arachidic acid microelectrode shows more stability for the 5-HT signal than does the 1.00 cc, extra heavy Nujol, stearic acid electrode.

EXAMPLE 48

The microelectrode prepared as described in Example 30, 1.5 g carbon (graphite), 1.24 cc extra heavy Nujol, and 100 mg palmitic acid (ratio 1.5:1.24:0.1) was used to obtain comparative data to show in vivo detection of DA and/or 5-HT and/or other biogenic amines with microelectrodes stereotaxically implanted in the nucleus accumbens of chloral hydrate anesthetized, virus free, male Sprague-Dawley laboratory rats, weighing 337-359 g. Twelve recordings (Scans Nos. 1-12) were obtained at ten minute intervals. Each biogenic chemical was detected in units of seconds. Each series of voltammograms show either the decrease in signal sensitivity until a reproducible baseline was achieved or the unexpected property of immediate, or earlier baseline or more stable baseline, in addition to showing the unexpected property of exhibiting a smaller decrease in signal sensitivity, as compared to a 1.00 cc Nujol, stearic acid microelectrode.

Peak areas were calculated by drawing a line from beginning potential to end potential and multiplying the peak height (mm) at peak potential of each electrochemical signal by the width (mm) of each electrochemical signal at $\frac{1}{2}$ the peak height (mm). Each peak area was converted from a 5 second time constant to a 1 second time constant by multiplying by 2.

In Scans 1-12 of the 1.24 cc Nujol, palmitic acid microelectrode Signal 1 (DA) had a peak potential at 0.140 V, beginning and end potentials at 0.050 and 0.200 V, and peak areas of 356 mm$^2$, 308 mm$^2$, 264 mm$^2$, 152 mm$^2$, 114 mm$^2$, 120 mm$^2$, 114 mm$^2$, 120 mm$^2$, 125 mm$^2$, 99 mm$^2$, 99 mm$^2$ and 1.08 mm$^2$, respectively. Signal 2 (5-HT), first measurably detected in Scan 3, had a peak potential at 0.275 V, beginning and end potentials at 0.225 and 0.325 V, and peak areas of 14 mm$^2$, 48 mm$^2$, 40 mm$^2$, 24 mm$^2$, 14 mm$^2$, 10 mm$^2$, 12 mm$^2$, 10 mm$^2$, 18 mm$^2$, and 19.5 mm$^2$, respectively. Signal 3, a putative biogenic chemical (HVA), first detected in Scan 8, had a peak potential at 0.440 V, beginning and end potentials at 0.375 and 0.500 V, and had peak areas of 17 mm$^2$, 17 mm$^2$, 17 mm$^2$, 19 mm$^2$ and 22.5 mm$^2$, respectively. Signal 4, a putative biogenic chemical (tentatively tryptophan or tryptophan derivatives) first measurably detected in Scan 3, had a peak potential at 0.610 V, beginning and end potentials at 0.525 and 0.665 V, and peak areas of 1680 mm$^2$, 1352 mm$^2$, 1150 mm$^2$, 1100 mm$^2$, 11300 mm$^2$, 460 mm$^2$, 561 mm$^2$, 527 mm$^2$, 464 mm$^2$ and 493 mm$^2$, respectively. Signal 5, a putative biogenic chemical, (tentatively an amino acid or neuropeptide), first measurably detected in Scan 5, had a peak potential at 0.760 V, beginning and end potentials at 0.675 and 0.810 V, and peak areas of 1066 mm$^2$, 1020 mm$^2$, 1088 mm$^2$, 1320 mm$^2$, 1290 mm$^2$, 1280 mm$^2$, 1190 mm$^2$ and 1190 mm$^2$, respectively.

Figure 59:
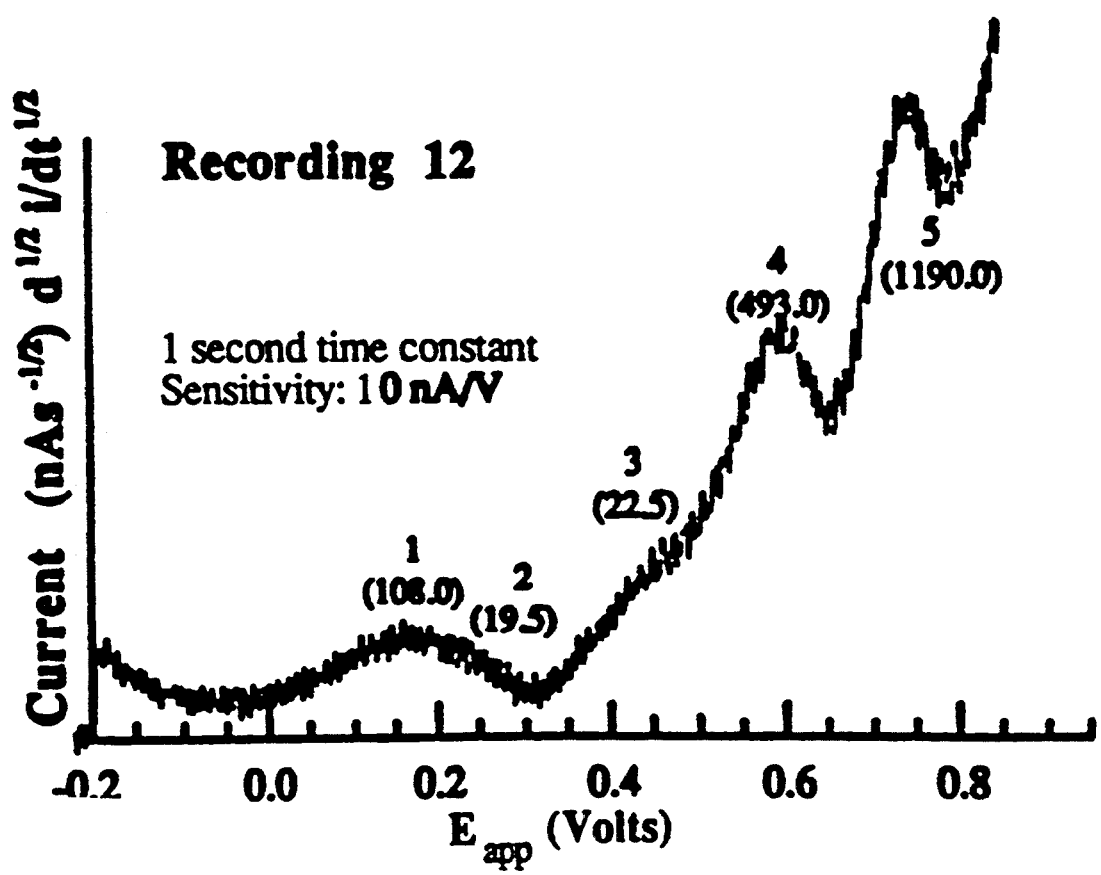
FIG. 59 is a semidifferential (semiderivative) voltammogram (1 second time constant; sensitivity 10 nA/V; body temperature) recording 12 of scans taken at ten minute intervals showing in vivo detection of dopamine, serotonin and other biogenic chemicals in a rat using a graphite microelectrode (diameter ranging between 150u-200u; 500-750μ length) containing 1.5 g carbon (graphite), 1.24 cc extra heavy Nujol and 100 mg palmitic acid.

Comparison of Scan 12 of the 1.00 cc Nujol, stearic acid microelectrode of Example 4 and the 1.24 cc Nujol, palmitic acid microelectrode (FIG. 59) indicated that a 1.24 cc Nujol, palmitic acid microelectrode had similar sensitivity for detection of DA and 5-HT, but had unexpectedly significantly better detection for Signal 5 than a 1.130 cc Nujol, stearic acid microelectrode. In addition, a 1.24 cc Nujol, palmitic acid microelectrode unexpectedly detected a putative biogenic chemical with a peak potential at 0.440 V (Signal 3; putative HVA) after approximately 70 minutes, which the 1.00 cc Nujol, stearic acid microelectrode did not detect.

EXAMPLE 49

The microelectrode prepared as described in Example 31, containing 1.5 g carbon (graphite), 1.24 cc extra heavy Nujol, and 100 mg lauric acid (ratio 1.5:1.24:0.1) was used to obtain comparative data to show in vivo detection of DA and/or 5-HT and/or other biogenic amines with microelectrodes stereotaxically implanted in the nucleus accumbens of chloral hydrate anesthetized, virus free, male Sprague-Dawley laboratory rats, weighing 337-359 g. Twelve recordings (Scans Nos. 1-12) were obtained at ten minute intervals. Each biogenic chemical was detected in units of seconds. Each series of voltammograms show either the decrease in signal sensitivity until a reproducible baseline was achieved or the unexpected property of immediate, or earlier baseline or more stable baseline, in addition to showing the unexpected property of exhibiting a smaller decrease in signal sensitivity, as compared to a 1.00 cc Nujol, stearic acid microelectrode.

In Scans 1-12 of the 1.24 cc Nujol, lauric acid microelectrode, Signal 1 (DA) had a peak potential at 0.100 V, beginning and end potentials at 0.015 and 0.190 V, and peak areas of 943 mm$^2$, 1056 mm$^2$, 1034 mm$^2$, 1034 mm$^2$, 1034 mm$^2$, 1034 mm$^2$, 1034 mm$^2$, 1034 mm$^2$ 1034 mm$^2$, 1034 mm$^2$, 1034 mm$^2$ and 1032 mm$^2$, respectively. Signal 2 (5-HT) had a peak potential at 0.260 V, beginning and end potentials at 0.210 and 0.310 V, and peak areas of 35 mm$^2$, 30 mm$^2$, 37.5 mm$^2$, 40 mm$^2$, 35 mm$^2$, 35 mm$^2$, 43.75 mm$^2$, 50 mm$^2$, 50 mm$^2$, 50mm$^2$, 50 mm$^2$ and 50 mm$^2$, respectively. Signal 3, a putative biogenic chemical (HVA), had a peak potential at 0.410 V, beginning and end potentials at 0.340 and 0.465 V, and peak areas of 90 mm$^2$, 40 mm$^2$, 48 mm$^2$, 56 mm$^2$, 60 mm$^2$, 90 mm$^2$, 90 mm$^2$, 90 mm$^2$, 96 mm$^2$, 90 mm$^2$, and 97.5 mm$^2$, respectively. Signal 4, a putative biogenic chemical (tentatively tryptophan or tryptophan derivatives), had a peak potential at 0.585 V, beginning and end potentials at 0.515 and 0.650 V, and peak areas of 1311 mm$^2$, 600 mm$^2$, 400 mm$^2$, 442 mm$^2$, 459 mm$^2$, 400 mm$^2$, 416 mm$^2$, 432 mm$^2$, 448 mm$^2$, 432 mm$^2$, 442 mm$^2$ and 442 mm$^2$, respectively. Signal 5 was out of range at this sensitivity.

Figure 60:
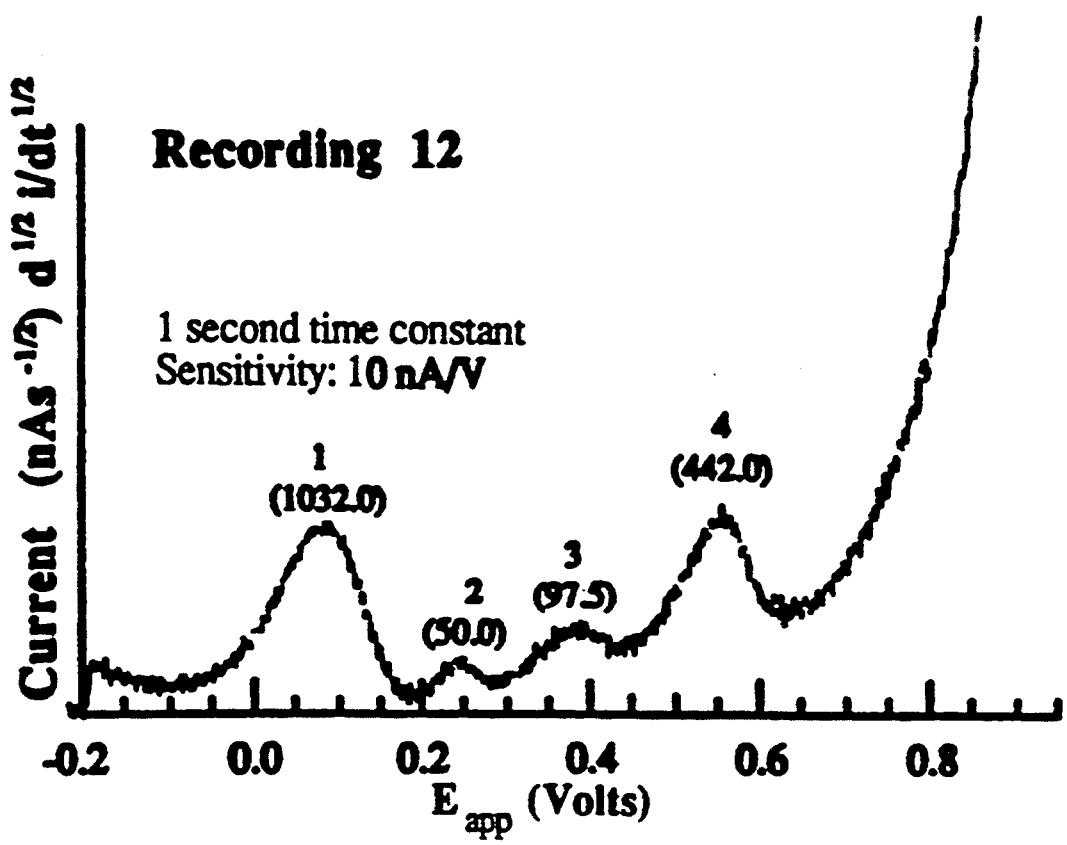
FIG. 60 is a semidifferential (semiderivative) voltammogram (1 second time constant; sensitivity 10 nA/V; body temperature) recording 12 of scans taken at ten minute intervals showing in vivo detection of dopamine, serotonin and other biogenic chemicals in a rat using a graphite microelectrode (diameter ranging between 150u-200u; 500-750μ length) containing 1.5 g carbon (graphite), 1.24 cc extra heavy Nujol and 100 mg lauric acid.

Comparison of Scans 12 of the 1.00 cc Nujol, stearic acid microelectrode of Example 44 and the 1.24 cc Nujol, lauric acid microelectrode (FIG. 60) indicated that a 1.24 cc Nujol, lauric acid microelectrode had greater sensitivity for detection of DA and 5-HT in vivo than did a 1.00 cc Nujol, stearic acid microelectrode. The DA peak had an area 9.8 times and the 5-HT peak had an area 3 times greater than the 1.00 cc Nujol, stearic acid areas. In addition, a lauric acid microelectrode achieves a baseline for DA, 5-HT and other putative biogenic chemicals with approximate peak potentials at 0.410 V (Signal 3; putative HVA) and 0.585 V (Signal 4; tentatively tryptophan or tryptophan derivatives) almost immediately upon first use. There was little or no decrease in signal sensitivity for each of the signals of biogenic chemicals, which was another advantage of the 1.24 cc Nujol, lauric acid microelectrode over a 1.00 cc, stearic acid microelectrode. This property would enable studies of brain disease to take place much faster than was allowed by a 1.00 cc Nujol, stearic acid microelectrode. The 5-HT signal was clearly demarcated from DA and from the putative HVA signal (Signal 3; putative HVA). This is a definite advantage for in vivo electrochemical studies.

EXAMPLE 50

Figure 61:
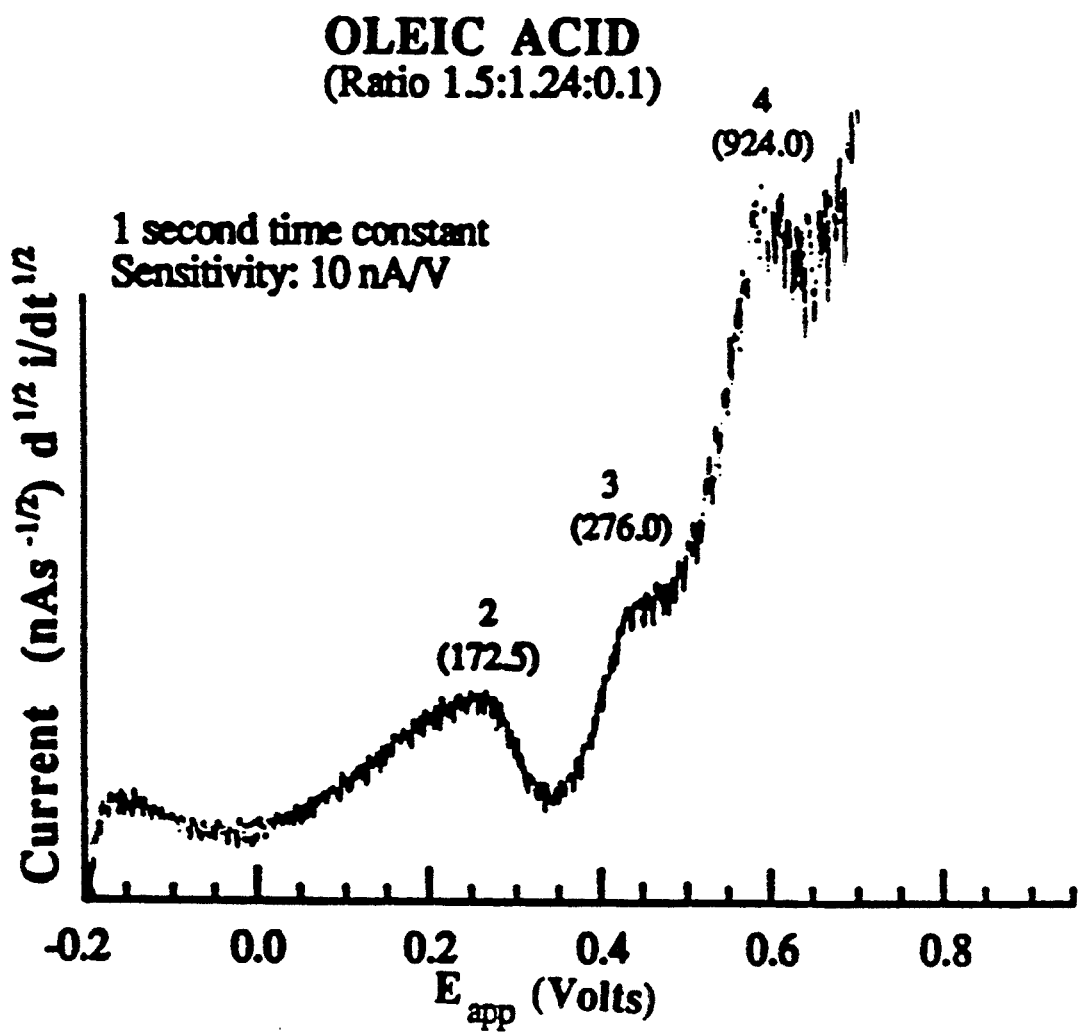
FIG. 61 is a semidifferential (semiderivative) voltammogram (1 second time constant; sensitivity 10 nA/V; body temperature) recording 12 of scans taken at ten minute intervals showing in vivo detection of dopamine, serotonin and other biogenic chemicals in a rat using a graphite microelectrode (diameter ranging between 150u-200u; 500-750μ length) containing 1.5 g carbon (graphite), 1.24 cc extra heavy Nujol and 100 mg oleic acid.

The microelectrode prepared as described in Example 33, containing 1.5 g carbon (graphite), 1.24 cc extra heavy Nujol, and 100 mg oleic acid (ratio 1.5:1.24:0.1) was used to obtain comparative data to show in vivo detection of DA and/or 5-HT and/or other biogenic amines with microelectrodes stereotaxically implanted in the nucleus accumbens of chloral hydrate anesthetized, virus free, male Sprague-Dawley laboratory rats, weighing 337–359 g. Twelve recordings (Scans Nos, 1–12) were obtained at ten minute intervals. FIG. 61 is Scan 12. Each biogenic chemical was detected in units of seconds. Each series of voltammograms show either the decrease in signal sensitivity until a reproducible baseline was achieved or the unexpected property of immediate, or earlier baseline or more stable baseline, in addition to showing the unexpected property of exhibiting a smaller decrease in signal sensitivity, as compared to a 1.00 cc Nujol, stearic acid microelectrode.

In FIG. 61, Signal 1 (DA) was not detectable. Signal 2 (5-HT) had a peak potential at 0.275 V, beginning and end potentials at 0.225 and 0.325 V, and a peak area of 172.5 mm$^2$. Signal 3, a putative biogenic chemical (HVA), had a peak potential at 0.425 V, beginning and end potentials at 0.350 and 0.475 V, and a peak area of 276 mm$^2$. Signal 4, a putative biogenic chemical (tentatively tryptophan or tryptophan derivatives) had a peak potential at 0.600 V, beginning and end potentials at 0.525 and 0.650 V, and peak areas of 924 mm$^2$. Signal 5 was Comparison of Scans 12 of the 1.00 out of range at this sensitivity. Nujol, stearic acid microelectrode of Example 44 and the 1.24 cc Nujol, oleic acid microelectrode indicated that a 1.24 cc Nujol, oleic acid microelectrode had greater sensitivity for detection of 5-HT in Vivo than does a 1.00 cc Nujol, stearic acid microelectrode, and unexpectedly, did not detect DA. The 5-HT peak had an area 10.5 times greater than the 1.00 cc Nujol, stearic acid 5-HT peak area.

EXAMPLE 51

The microelectrode prepared as described in Example 34, containing 1.5 g carbon (graphite), 1.24 cc extra heavy Nujol and 100 mg elaidic acid (ratio 1.5:1.24:0.1) was used to obtain comparative data to show in vivo detection of DA and/or 5-HT and/or other biogenic amines with microelectrodes stereotaxically implanted in the nucleus accumbens of chloral hydrate anesthetized, virus free, male Sprague-Dawley laboratory rats, weighing 337–359 g. Twelve recordings (Scans Nos. 1–12) were obtained at ten minute intervals. Each biogenic chemical was detected in units of seconds. Each series of voltammograms show either the decrease in signal sensitivity until a reproducible baseline was achieved or the unexpected property of immediate, or earlier baseline or more stable baseline, in addition to showing the unexpected property of exhibiting a smaller decrease in signal sensitivity, as compared to a 1.00 cc Nujol, stearic acid microelectrode of the references cited.

In a voltammogram obtained with this microelectrode, Signals 1 (DA) and 2 (5-HT) were not detected. Signal 3, a putative biogenic chemical (HVA), had a peak potential at 0.450 V, beginning and end potentials at 0.375 and 0.525 V, and a peak area of 120 mm$^2$. Signals 4 (tentatively tryptophan or tryptophan derivatives) and 5 (tentatively an amino acid or neuropeptide) were out of range at this sensitivity.

Comparison of Scans 12 of the 100 Nujol, stearic acid microelectrode of Example 44 and the 1.24 cc Nujol, elaidic acid microelectrode indicated that a 100 cc Nujol, stearic acid, a saturated eighteen carbon fatty acid microelectrode detects both DA and 5-HT whereas unexpectedly the trans-conformation eighteen carbon unsaturated fatty acid does not. Furthermore, comparison of the data generated by the 1.00 cc Nujol, stearic acid microelectrode of Example 44, the 1.24 cc Nujol, oleic acid microelectrode of Example 50 and the 1.24 cc Nujol, elaidic acid microelectrode indicated that the detection of DA and/or 5-HT, as well as other biogenic chemicals, was partially dependent on whether the fatty acid was saturated or unsaturated and, if unsaturated, the conformation of the double bond.

EXAMPLE 52

The microelectrode prepared as described in Example 35, containing 1.5 g carbon (graphite), 1.24 cc extra heavy Nujol, and 100 mg squalene (ratio 1.5:1.24:0.1) was used to obtain comparative data to show in vivo detection of DA and/or 5-HT and/or other biogenic amines with microelectrodes stereotaxically implanted in the nucleus accumbens of chloral hydrate anesthetized, virus free, male Sprague-Dawley laboratory rats, weighing 337-359 g. Twelve recordings (Scans Nos. 1-12 were obtained at ten minute intervals. Each biogenic chemical was detected in units of seconds. Each series of voltammograms show either the decrease in signal sensitivity until a reproducible baseline was achieved or the unexpected property of immediate, or earlier baseline or more stable baseline, in addition to showing the unexpected property of exhibiting a smaller decrease in signal sensitivity, as compared to a 100 cc Nujol, stearic acid microelectrode.

Peak areas were calculated by drawing a line from beginning potential to end potential and multiplying the peak height (mm) at peak potential of each electrochemical signal by the width (mm) of each electrochemical signal at ½ the peak height (mm). Each peak area was converted from a 5 second time constant to a 1 second time constant by multiplying by 2.

In the twelfth voltammogram (Scan 12) obtained with a 1.24 cc Nujol, squalene microelectrode, Signal 1 (DA) had a peak potential at 0.150 V, beginning and end potentials of 0.050 and 0.200 V, a peak area of 220 mm$^2$. Signal 2 (5-HT) a peak at 0.265 V, beginning and end potentials at 0.225 and 0.32:5 V and a peak area of 8 mm$^2$. In addition, Signal 3, a putative biogenic chemical (HVA), had a peak potential at 0.440 V, beginning and end potentials of 0.375 and 0.500 V and a peak area of 11 mm$^2$. Signal 4, a putative biogenic chemical (tentatively tryptophan or tryptophan derivatives) had a peak potential at 0.585 V, beginning and end potentials at 0.525 and 0.655 V, and a peak area of 180 mm$^2$. Signal 5 was out of range at this sensitivity.

Comparison of Scan 12 indicated that a 1.24 cc Nujol, squalene microelectrode had greater sensitivity for detection of DA in vivo than does a 1.00 cc Nujol, stearic acid microelectrode. The DA peak had an area 2.1 times greater than the 1.00 cc Nujol, stearic acid DA peak area.

EXAMPLE 53

The microelectrode prepared as described in Example 37, containing 1.5 g carbon (graphite), 1.00 cc extra heavy Nujol, and 10 mg arachidic acid stearyl ester (ratio 1.5:1.00:0.01) was used to obtain comparative data to show in vivo detection of DA and/or 5-HT and/or other biogenic amines with microelectrodes stereotaxically implanted in the nucleus accumbens of chloral hydrate anesthetized, virus free, male Sprague-Dawley laboratory rats, weighing 337-359 g. Twelve recordings (Scans Nos. 1-12) were obtained at ten minute intervals. Each biogenic chemical was detected in units of seconds. Each series of voltammograms show either the decrease in signal sensitivity until a reproducible baseline was achieved or the unexpected property of immediate, or earlier baseline or more stable baseline, in addition to showing the unexpected property of exhibiting a smaller decrease in signal sensitivity, as compared to a 100 cc Nujol, stearic acid microelectrode.

In the twelfth voltammogram obtained with this microelectrode, Signal 1 (DA) had a peak potential at 0.175 V, beginning and end potentials at 0.065 and 0.240 V, and a peak area of 207 mm$^2$. Signal 2 (5-HT) had a peak potential at 0.300 V, beginning and end potentials at 0.250 and 0.350 V, and a peak area of 3.5 mm$^2$. Signal 3, a putative biogenic chemical (HVA), had a peak potential at 0.450 V, beginning and end potentials at 0.375 and 0.500 V, and a peak area of 26.5 mm$^2$. Signal 4, a putative biogenic chemical (tentatively tryptophan or tryptophan derivatives) had a peak potential at 0.625 V, beginning and end potentials at 0.540 and 0.690 V, and a peak area of 153.13 mm$^2$. Signal 5 was out of range at this sensitivity. Another unexpected advantage was the clear definition of peaks, including those for DA and 5-HT.

Comparison of Scan 12 indicated that a 1.00 cc Nujol, 10 mg arachidic acid stearyl ester microelectrode had greater sensitivity for detection of DA in vivo than does 1.00 cc Nujol, stearic acid microelectrode. The DA peak had an area 2 times greater than the 1.00 cc Nujol, stearic acid DA peak area.

EXAMPLE 54

Figure 62:
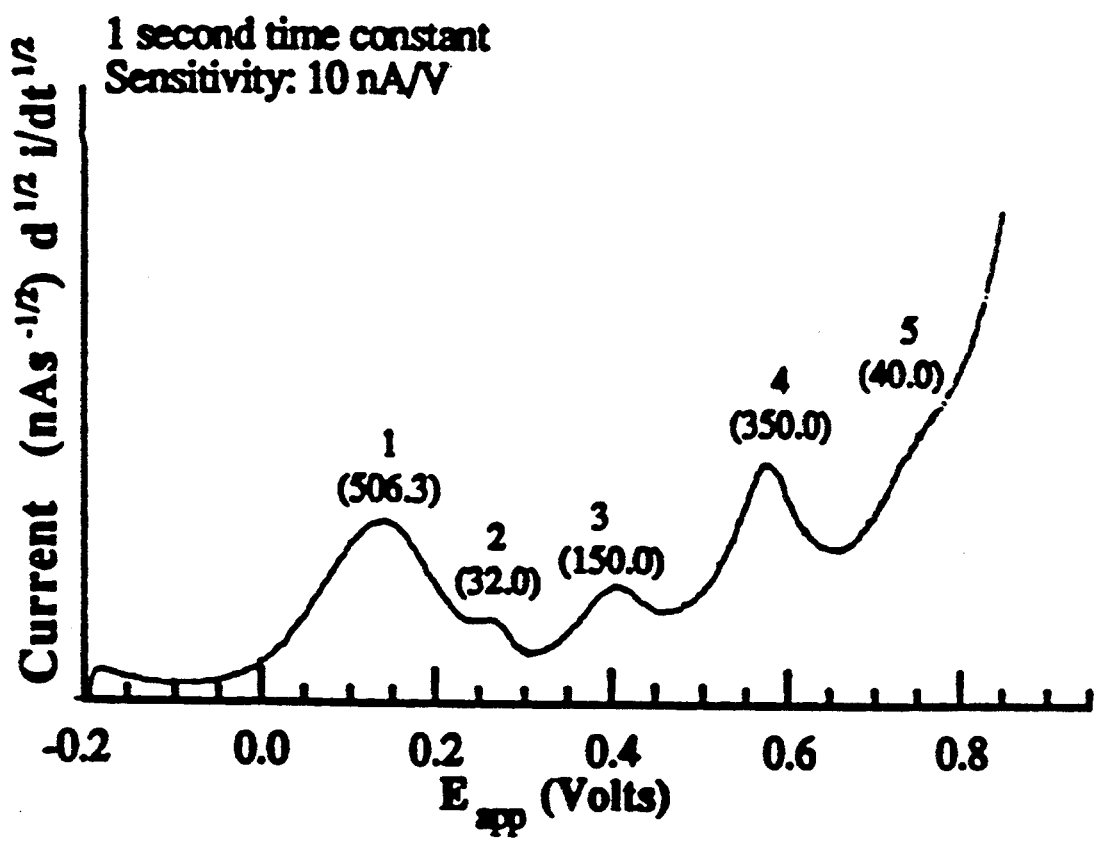
FIG. 62 is a semidifferential (semiderivative) voltammogram (1 second time constant; sensitivity 10 nA/V; body temperature) recording 12 of scans taken at ten minute intervals showing in vivo detection of dopamine, serotonin and other biogenic chemicals in a rat using a graphite microelectrode (diameter ranging between 150u-200u; 500-750μ length) containing 1.5 g carbon (graphite), 1.24 cc extra heavy Nujol and 100 mg cardiolipin.

The microelectrode prepared as described in Example 39, containing 1.5 g carbon (graphite), 1.24 cc extra heavy Nujol, and 100 mg cardiolipin (ratio 1.5:1.24:0.1) was used to obtain comparative data to show in vivo detection of DA and/or 5-HT and/or other biogenic amines with microelectrodes stereotaxically implanted in the nucleus accumbens of chloral hydrate anesthetized, virus fie, male Sprague-Dawley laboratory rats, weighing 337-359 g. Twelve recordings (Scans Nos. 1-12) were obtained at ten minute intervals, but only Scan 12 data was presented herein (FIG. 62). Each biogenic chemical was detected in units of seconds. Each series of voltammograms show either the decrease in signal sensitivity until a reproducible baseline was achieved or the unexpected property of immediate, or earlier baseline or more stable baseline, in addition to showing the unexpected property of exhibiting a smaller decrease in signal sensitivity, as compared to a 1.00 cc Nujol, stearic acid microelectrode.

Peak areas were calculated by drawing a line from beginning potential to end potential and multiplying the peak height (mm) at peak potential of each electrochemical signal by the width (mm) of each electrochemical signal at ½ the peak height (mm). Each peak area was converted from a 5 second time constant to a 1 second time constant by multiplying by 2.

In FIG. 62, Signal 1 (DA) had a peak potential at 0.130 V, beginning and end potentials at 0.040 and 0.215 V, and a peak area of 506.25 mm$^2$. Signal 2 (5-HT) had a peak potential at 0.260 V, beginning and end potentials at 0.225 and 0.300 V, and a peak area of 32 mm$^2$. Signal 3, a putative biogenic chemical (HVA), had a peak potential at 0.400 V, beginning and end potentials at 0.325 and 0.450 V, and a peak area of 150 mm$^2$. Signal 4, a putative biogenic chemical (tentatively tryptophan or tryptophan derivatives) had a peak potential at 0.565 V, beginning and end potentials at 0.525 and 0.665 V, and a peak area of 350 mm$^2$. Signal 5, a putative biogenic chemical (tentatively an amino acid or neuropeptide), had a peak potential at 0.750 V, beginning and end potentials at 0.675 and 0.800 V, and a peak area 40 mm$^2$.

Figure 55:
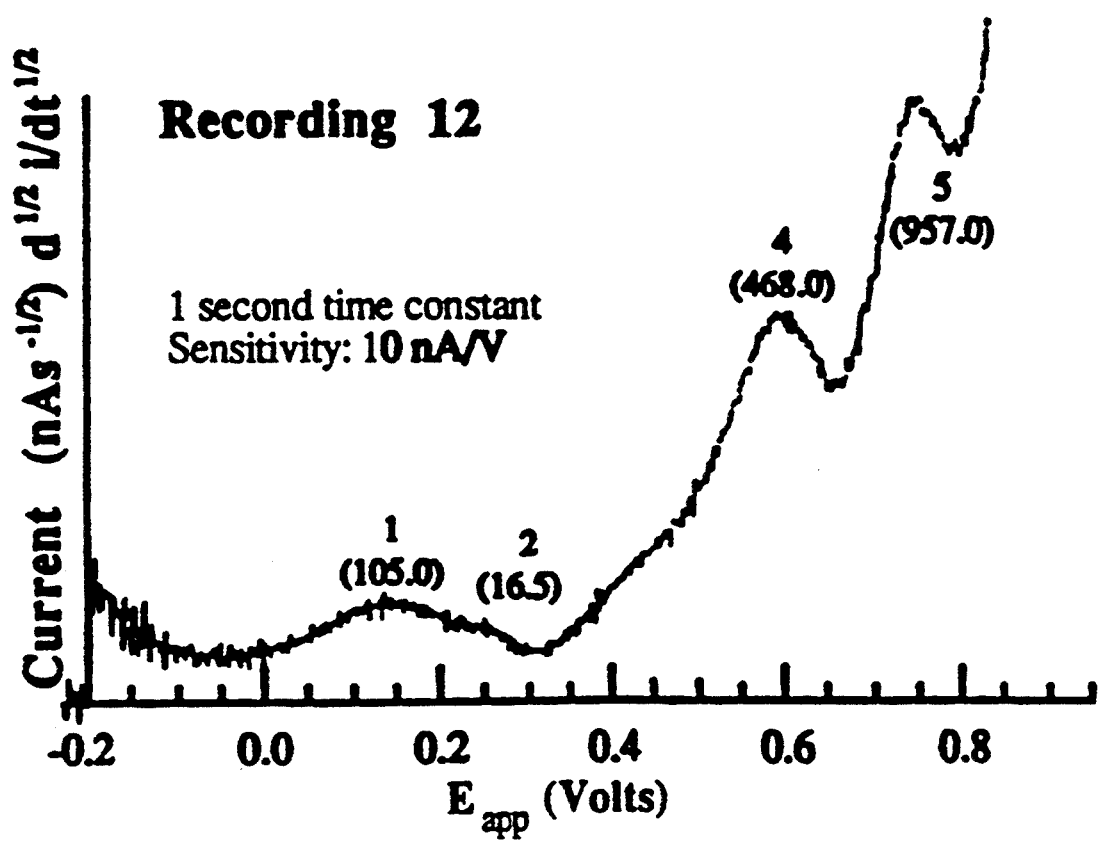
FIG. 55 is a semidifferential (semiderivative) voltammogram (1 second time constant; sensitivity 10 nA/V; body temperature) recording 12 of scans taken at ten minute intervals showing in vivo detection of dopamine, serotonin and other biogenic chemicals in rats using a graphite microelectrode (diameter ranging between 150u–200u; 500–750$\mu$ length) containing 1.5 g carbon (graphite), 1.00 cc extra heavy Nujol and 100 mg stearic acid.
Figure 56:
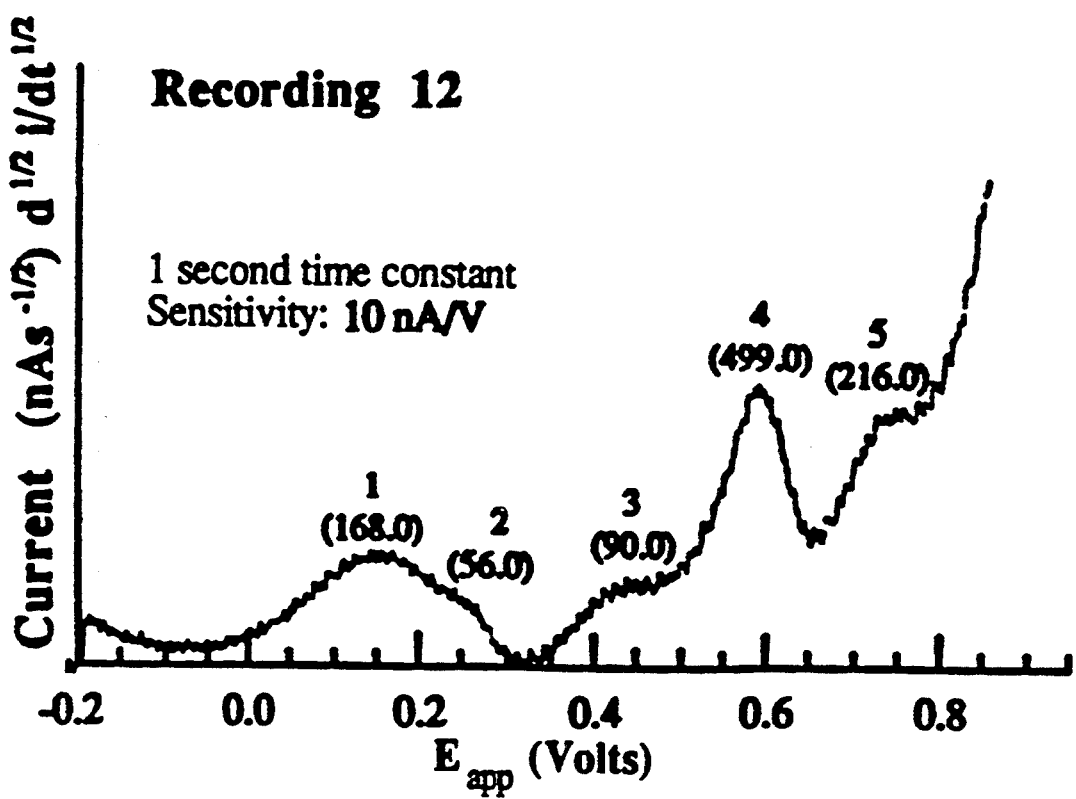
FIG. 56 is a semidifferential (semiderivative) voltammogram (1 second time constant; sensitivity 10 nA/V; body temperature) recording 12 of scans taken at ten minute intervals showing in vivo detection of dopamine, serotonin and other biogenic chemicals in a rat using a graphite microelectrode (diameter ranging between 150u–200u; 500–750$\mu$ length) containing 1.5 g carbon (graphite), 1.24 cc extra heavy Nujol and 100 mg stearic acid.

Comparison of Scan 12 of FIGS. 55 and 62 indicates that a 1.24 cc Nujol, cardiolipin microelectrode had greater sensitivity for detection of DA and 5-HT in vivo than does a 1.00 cc Nujol, stearic acid microelectrode. The DA peak had an area 4.8 times and the 5-HT peak: had an area 1.9 times greater than the 1.00 cc Nujol, stearic acid areas, respectively. Another unexpected advantage of the cardiolipin microelectrode was that each of the detected signals was clearly defined. There was a very clear demarcation between the DA and 5-HT signals.

EXAMPLE 55

The microelectrode prepared as described in Example 41, containing 1.5 g carbon (graphite), 1.24 cc extra heavy Nujol, and 66 mg N-stearoyl-DL-dihydrosphingosine (ratio 1.5:1.24:0.066) was used to obtain comparative data to show in vivo detection of DA and/or 5-HT and/or other biogenic amines with microelectrodes stereotaxically implanted in the nucleus accumbens of chloral hydrate anesthetized, virus free, male Sprague-Dawley laboratory rats, weighing 337–359 g. Twelve recordings (Scans Nos. 1–12) were obtained at ten minute intervals. Each biogenic chemical was detected in units of seconds. Each series of voltammograms show either the decrease in signal sensitivity until a reproducible baseline was achieved or the unexpected property of immediate, or earlier baseline or more stable baseline, in addition to showing the unexpected property of exhibiting a smaller decrease in signal sensitivity, as compared to a 1.00 cc Nujol, stearic acid microelectrode.

Peak areas were calculated by drawing a line from beginning potential to end potential and multiplying the peak height (mm) at peak potential of each electrochemical signal by the width (mm) of each electrochemical signal at ½ the peak height (mm). Each peak area was converted from a 5 second time constant to a 1 second time constant by multiplying by 2.

In the twelfth voltammogram obtained with this microelectrode, Signal 1 (DA) had a peak potential at 0.160 V, beginning and end potentials at 0.065 and 0.240 V, and a peak area of 360 mm$^2$. Signal 2 (5-HT) had a peak potential at 0.300 V, beginning and end potentials at 0.250 and 0.350 V, and a peak area of 15 mm$^2$. Signal 3, a putative biogenic chemical (HVA), had a peak potential at 0.445 V, beginning and end potentials at 0.370 and 0.515 V, and a peak: area of 52.5 mm$^2$. Signal 4, a putative biogenic chemical (tentatively tryptophan or tryptophan derivatives), had a peak potential at 0.625 V, beginning and end potentials at 0.545 and 0.705 V, and a peak areas of 268.25 mm$^2$. The N-stearoyl-DL-dihydrosphingosine unexpectedly detects putative HVA (Signal 3) with a clearly defined signal, whereas a 1.00 cc Nujol, stearic acid microelectrode does not.

Comparison of Scan 12 data indicated that a 1.24 cc Nujol, 66 mg N-stearoyl-DL-dihydrosphingosine microelectrode had greater sensitivity for detection of DA in vivo than does a 1.00 cc Nujol, stearic acid microelectrode. The DA peak had an area 3.4 times greater than the 1.00 cc Nujol, stearic acid DA peak area.

EXAMPLE 56

The microelectrode prepared as described in Example 42, containing 1.5 g carbon (graphite), 1.00 cc extra heavy Nujol, and 10 mg N-stearoyl cerebroside (ratio 1.5:1.00:0.01) was used to obtain comparative data to show in vivo detection of DA and/or 5-HT and/or other biogenic amines with microelectrodes stereotaxically implanted in the nucleus accumbens of chloral hydrate anesthetized, virus free, male Sprague-Dawley laboratory rats, weighing 337–359 g. Twelve recordings (Scans Nos. 1–12) were obtained at ten minute intervals. Each biogenic chemical was detected in units of seconds. Each series of voltammograms show either the decrease in signal sensitivity until a reproducible baseline was achieved or the unexpected property of immediate, or earlier baseline or more stable baseline, in addition to showing the unexpected property of exhibiting a smaller decrease in signal sensitivity, as compared to a 100 cc Nujol, stearic acid microelectrode.

Peak areas were calculated by drawing a line from beginning potential to end potential and multiplying the peak height (mm) at peak potential of each electrochemical signal by the width (mm) of each electrochemical signal at ½ the peak height (mm). Each peak area was converted from a 5 second time constant to a 1 second time constant by multiplying by 2.

In the twelfth voltammogram obtained with this microelectrode, Signal 1 (DA) had a peak potential at 0.120 V, beginning and end potentials at 0.035 and 0.185 V, and a peak area. of 279.5 mm$^2$. Signal 2 (5-HT) had a peak potential at 255 V, beginning and end potentials at 0.200 and 0.300 V, and a peak area of 30 mm$^2$. Signal 3, a putative biogenic chemical (HVA), had a peak potential at 0.405 V, beginning and end potentials at 0.335 and 0.465 V, and a peak area of 34.5 mm$^2$. Signal 4, a putative biogenic chemical (tentatively tryptophan or tryptophan derivatives), had a peak potential at 0.575 V, beginning and end potentials at 0.505 and 0.650 V, and a peak area of 192 mm$^2$.

Comparison of Scan 12 data indicated that a 1.00 cc Nujol, 10 mg N-stearoyl cerebroside microelectrode had greater sensitivity for detection of DA and 5-HT in vivo than does a 1.00 cc Nujol, stearic acid microelectrode. The DA peak had an area 2.7 times and the 5-HT peak had an area 1.8 times greater than the 1.00 cc Nujol, stearic acid peak areas, respectively. An unexpected result, showing a clear demarcation between the DA and 5-HT signals, provides the N-stearoyl cerebroside microelectrode with a decided advantage over a 100 cc Nujol, stearic acid microelectrode.

While specific embodiments of the invention have been shown and described, it should be apparent that many modifications can be made thereto without departing from the spirit and scope of the invention. Accordingly, the invention is not limited by the foregoing description, but is only limited by the claims appended hereto.

What is claimed is:

1. A microelectrode for inserting in vivo, in situ or in vitro into a warm-blooded or cold-blooded animal brain or body, or extra-corporeally of said animal brain or body and measuring, in vivo, in situ, or in vitro, intracellular and/or extracellular concentrations and/or release and/or reuptake inhibition of one or more biogenic chemicals, comprising, a mixture of graphite, oil and at least one compound selected from the group consisting of complex lipids and simple lipids and salts thereof and wherein the complex lipid is selected from the group consisting of acylglycerols, phosphoglycerides, sphingolipids, glycolipids, lipoproteins and waxes and the simple lipid is selected from the group consisting of terpenes, steroids and prostaglandins, said graphite, said oil, and the compound being present in said microelectrode in a ratio of graphite, in weight in grams, oil, in volume, in cubic centimeters, and compound, in weight in grams, of 0.15 to 7.5:0.1 to 5.0:0.01 to 0.5, respectively, the diameter of the microelectrode ranging from about 0.001 μm to about 10 mm, and said oil has a specific gravity from 0.5 to 2.

2. The microelectrode according to claim 1, wherein the biogenic chemical is selected from the group consisting of amines, amine metabolites, ascorbic acid, amino acids, neurotransmitters, putative neurotransmitters, neuromodulators, and neuropeptides.

3. The microelectrode according to claim 2, wherein the biogenic chemical is selected from the group consisting of dopamine, norepinephrine, serotonin and ascorbic acid.

4. The microelectrode according to claim 1, wherein the graphite, oil and compound is present in a ratio of graphite, in weight in grams, oil, in volume in cubic centimeters, and compound, in weight in grams of 1.0 to 2.0:0.1 to 2.0:0.01 to 0.5.

5. The microelectrode according to claim 1, wherein the compound is an acyglycerol, phosphoglyceride, sphingolipid, wax, or salt thereof.

6. The microelectrode according to claim 5, wherein the compound is an acylglycerol or salt thereof.

7. The microelectrode according to claim 6, wherein the compound is arachidic acid stearyl ester.

8. The microelectrode according to claim 5, wherein the compound is a phosphoglyceride or salt thereof.

9. The microelectrode according to claim 5, wherein the compound is a sphingolipid or salt thereof.

10. The microelectrode according to claim 9, wherein the compound is a sphingosine, cerebroside, ceramide, dihexoside, trihexoside, tetrahexoside or salt thereof.

11. The microelectrode according to claim 10, wherein the compound is a sphingosine or salt thereof.

12. The microelectrode according to claim 11, wherein the compound is N-stearoyl-DL-dihydrosphingosine.

13. The microelectrode according to claim 10, wherein the compound is a ceramide or salt thereof.

14. The microelectrode according to claim 10, wherein the compound is a cerebroside or salt thereof.

15. The microelectrode according to claim 14, wherein the compound is a galactocerebroside or salt thereof.

16. The microelectrode according to claim 15, wherein the compound is N-stearoylcerebroside.

17. The microelectrode according to claim 15, wherein the compound is a sulfatide or salt thereof.

18. The microelectrode according to claim 14, wherein the compound is a psychosine or salt thereof.

19. The microelectrode according to claim 10, wherein the compound is a dihexoside, trihexoside, tetrahexoside or salt thereof.

20. The microelectrode according to claim 5, wherein the compound is a wax or salt thereof.

21. The microelectrode according to claim 11, having a diameter ranging from about 2 $\mu$m to about 500 $\mu$m.

22. The microelectrode according to claim 21, having a diameter ranging from about 150 $\mu$m to about 200 $\mu$m.

23. The microelectrode according to claim 11, having a diameter ranging from about 50 $\mu$m to about 1 mm.

24. The microelectrode according to claim 1, wherein the graphite, oil and compound is present in a ratio of graphite, in weight in grams, oil, in volume in cubic centimeters, and compound, in weight in grams, of 1.0 to 1.5:1.14 to 1.34:0.01 to 0.5.

25. The microelectrode according to claim 1, wherein the compound is a prostaglandin or salt thereof.

26. The microelectrode according to claim 1, wherein the compound is a steroid or salt thereof.

27. The microelectrode according to claim 1, wherein the compound is a terpene or salt thereof.

28. A microelectrode for inserting in vivo, in situ and in vitro into a warm-blooded or cold-blooded animal brain or body, or extra-corporeally of said animal brain or body and measuring, in vivo, in situ, or in vitro intracellular and/or extracellular concentrations and/or release and/or reuptake inhibition of one or more biogenic chemicals, comprising, a mixture of graphite, oil and at least two compounds, the first being arachidic acid and the second being stearic acid, said at least two compounds being employed in a 1:1 weight ratio with respect to each other, said mixture having a ratio of graphite, in weight in grams, oil, in volume in cubic centimeters, and combined compound weight in grams of 1.0 to 2.0:0.1 to 5.0:0.01 to 0.5, respectively, and the diameter of said microelectrode ranging from about 2 $\mu$m to about 1 mm.

29. The microelectrode according to claim 28, having a diameter ranging from about 2 $\mu$m to about 500 $\mu$m.

30. The microelectrode according to claim 28 having a diameter ranging from about 50 $\mu$m to about 1 mm.

31. A device capable of analyzing the concentration of one or more biogenic chemicals in vivo, in vitro, or in situ comprising:

an auxiliary microelectrode for placing in contact with an outer layer of an in vivo organ, in vivo sub-organ, in situ specimen or in vitro specimen to be analyzed;

a reference microelectrode for placing in contact with the outer layer of the organ, sub-organ, in situ specimen or in vitro specimen to be analyzed;

an indicator microelectrode comprising, a mixture of graphite, oil and at least one compound selected from the group consisting of complex lipids and simple lipids and salts thereof and wherein the complex lipid is selected from the group consisting of acylglycerols, phosphoglycerides, sphingolipids, glycolipids, lipoproteins and waxes and the simple lipid is selected from the group consisting of terpenes, steroids and prostaglandins, for inserting into the organ or sub-organ interior, said graphite, said oil and the compound being in a ratio of graphites in weight in grams, oil, in volume, in cubic centimeters, and compound, in weight in grams, of 0.15 to 7.5:0.1 to 5.0:0.01 to 0.5, respectively, said indicator microelectrode having a diameter ranging from about 0.001 $\mu$m to about 10 mm and said oil has a specific gravity from 0.5 to 2; and means for electrochemically measuring said concentration of said one or more biogenic chemicals by a technique selected from the group consisting of square wave measurement, amperometric measurement, semidifferential voltammetry measurement, linear scanning measurement, differential pulse measurement, chronoamperometry measurement and double differential pulse measurement, and wherein said auxiliary microelectrode, said reference microelectrode, and said indicator microelectrode are functionally connected to said means for electrochemically measuring.

32. A device capable of analyzing the concentration of one or more biogenic chemicals in vivo, in vitro, or in situ comprising:

an auxiliary microelectrode for placing in contact with an outer layer of an in vivo organ, in vivo sub-organ, in situ specimen or in vitro specimen to be analyzed;

a reference microelectrode for placing in contact with an outer layer of an in vivo organ, in vivo sub-organ, in situ specimen or in vitro specimen to be analyzed;

an indicator microelectrode comprising, a mixture of graphite, oil and at least one compound selected from the group consisting of unsaturated fatty acids, derivatives of unsaturated fatty acids and salts thereof, for inserting into the organ or sub-organ interior, said graphite, said oil and the compound being in a ratio of graphite, in weight in grams, oil, in volume, in cubic centimeters, and compound, in weight in grams, of 0.15 to 7.5:0.1 to 5.0:0.01 to 0.5, respectively, said indicator microelectrode having a diameter ranging from about 0.001 μm to about 10 mm; said oil having a specific gravity from 0.5 to 2; and means for electrochemically measuring said concentration of said one or more biogenic chemicals by a technique selected from the group consisting of square wave measurement, amperometric measurement, semidifferential voltammetry measurement, linear scanning measurement, differential pulse measurement, chronoamperometry measurement and double differential pulse measurement, and wherein said auxiliary microelectrode, said reference microelectrode, and said indicator microelectrode are functionally connected to said means for electrochemically measuring.

* * * * *